US007312026B2

(12) United States Patent
Kruh et al.

(10) Patent No.: US 7,312,026 B2
(45) Date of Patent: Dec. 25, 2007

(54) MRP-RELATED ABC TRANSPORTER ENCODING NUCLEIC ACIDS AND METHODS OF USE THEREOF

(75) Inventors: Gary Kruh, Philadelphia, PA (US); Kun Lee, Cranbury, NJ (US); Martin Belinsky, Warminster, PA (US); Lisa Bain, Townville, SC (US)

(73) Assignee: Fox Chase Cancer Center, Philadelphia, PA (US)

( * ) Notice: Subject to any disclaimer, the term of this patent is extended or adjusted under 35 U.S.C. 154(b) by 306 days.

(21) Appl. No.: 10/889,503

(22) Filed: Jul. 12, 2004

(65) Prior Publication Data

US 2005/0063968 A1    Mar. 24, 2005

Related U.S. Application Data

(62) Division of application No. 09/647,140, filed as application No. PCT/US99/06644 on Mar. 26, 1999, now Pat. No. 6,803,184.

(60) Provisional application No. 60/095,153, filed on Aug. 3, 1998, provisional application No. 60/079,759, filed on Mar. 27, 1998.

(51) Int. Cl.
*C12Q 1/00* (2006.01)
*C12N 15/00* (2006.01)
*C12N 15/63* (2006.01)
*C07H 21/04* (2006.01)
*A01N 63/00* (2006.01)

(52) U.S. Cl. .................... 435/4; 435/320.1; 435/325; 435/455; 536/23.1; 536/23.5; 424/93.21

(58) Field of Classification Search ............... 424/93.2, 424/93.21, 93.5, 93.7; 435/320.1, 455, 4, 435/325; 536/23.5, 24.1, 23.1
See application file for complete search history.

(56) References Cited

U.S. PATENT DOCUMENTS 5,766,880 A * 6/1998 Deeley et al. ............. 435/69.1

OTHER PUBLICATIONS

Rudinger, 1976, Peptide Hormones, Parsons, University Park Press, Baltimore, p. 1-7.*
Kaye et al., 1990, Proc. Natl. Acad. Sci. USA, vol. 87, pp. 6922-6926.*
Skolnick et al., 2000, Trends in Biotech, vol. 18, p. 34-39.*
Deonarain, 1998, Expert Opin. Ther. Pat., vol. 8, pp. 53-69.*
Verma, Sep. 1997, Nature, vol. 389, pp. 239-242.*
Eck et al., 1996, Goodman & Gilman's The Pharmacological Basis of Therapeutics, McGraw-Hill, New York, p. 77-101.*
Gorecki, 2001, Expert Opin. Emerging Drugs, 6(2): 187-198.*
Marcel Kool et al., "Analysis of Expression of cMOAT (MRP2), MRP3, MRP4, and MRP5, Homologues of the Multidrug Resistance-associated Protein Gene (MRP1), in Human Cancer Cell Lines"; Cancer Research 57:3537-3547, Aug. 15, 1997.
Toshihiro Suzuki et al., "cDNA Cloning of a Short Type of Multidrug Resistance Protein Homologue, SMRP, from a Human Lung Cancer Cell Line"; Biochemical and Biophysical Research Communications, 238: 790-794 (1997).
Rando Allikmets et al., "Characterization of the human ABC superfamily: isolation and mapping of 21 new genes using the Expressed Sequence Tags database"; Human Molecular Genetics, vol. 5, No. 10, 1649-1655 (1996).

* cited by examiner

*Primary Examiner*—Shin-Lin Chen
(74) *Attorney, Agent, or Firm*—Dann, Dorfman, Herrell & Skillman, P.C.; Robert C. Netter; Kathleen D. Rigaut

(57) ABSTRACT

Novel human MOAT genes and their encoded proteins are provided herein. The MRP-related ABC transporters encoded by the disclosed nucleic acid sequences play a pivotal role in the efflux of pharmacologically beneficial reagents from tumor cells. MOAT genes and their encoded proteins provide valuable therapeutic targets for the design of anti-cancer agents which inhibit the aberrant growth of malignant cells.

15 Claims, 57 Drawing Sheets

Fig. 1A

```
MOAT-B   646 ........................TPTLRNRTFSESSVWSQQSSRPSLKDGALESQDY..ENVPVTLSEENRSEGKVGFQAYKNYFRAGAHMIVFIFLILLNTAAQVAYVLQ  731
                                     .::  .:.:: ||  :.::: || ::: .|.: .|.:|::: :.| |::: ::|:.  ::.|.
MRP      894 KQMENGMLVTDSAGKQLQRQLSSSSYSGDISRHHNSTAELQKAEAKKEETWKLMEADKAQTGQVKLSVYMDYMKAIGLFISFLSIFLF.MCNHVSALAS   992

MOAT-B   732 DWWLSYWANKQSMLNVTVNGGGNVTEKLDLNWYLGIYSGLTVATVLFGIARSLLVFYVLVNSSQTLHNRMFESILKAPVLFFDRNPIGRILNRFSKDIGH  831
             ::|||.|.:       |:|:|:: |:    |:::|: ::     :::  ::|   ||:|| .:.:|.   ::::|::  ||:|||  ::|||
MRP      993 NYMLSLWTD......DPIVNGTQEHTKVR.....LSVYGALGISQGIAVFGYSMAVSIGILASRCLRVDLLHSILRSPMSFFERTPSGNLVNRFSKELDT 1082

MOAT-B   832 LDDLLPLTFLDFIQTLLQVVGVVSVAVAVIPMIAIPLVPLGIIFIFLRRYFLETSRDVKRLESTTRSPVFSHLSSSLQGLWTIRAYKAEERCQELFDAHQ  931
             :|.::| ||::|:||.:.::|    |.::|:: :.| :||:|::|.||||:||:.|::.:|.   ||:|||||.|..|
MRP     1083 VDSMIPEVIKMFMGSLFNVIGACIVILLATPIAAIIIPPLGLIYFFVQRFYVASSRQLKRLESVSRSPVYSHFNETLLGVSVIRAFEEQERFIHQSDLKV 1182

MOAT-B   932 DLHSEAWFLFLTSRMFAVRLDAICAMFVIVAFGSLILAKTLDAGQVGLALSYALTLMGMFQWCVRQSAEVENMAISVERVIEYTDLEKEAPWEYQK.R  1030
             :|..:|.|| ||:|:.:::| |.||.|  :.:|:|.:. .::: ::|   :|.|:| ::::|::|     |:.:::|:|::|.::|::| |.:
MRP     1183 DENQKAYYPSIVANRWLAVRLECVGNCIVLFAALFAVISRHSLSAGLVGLSVSYSLQVTTYLNWLVRMSSEMETNIVAVERLKEYSETEKEAPWQIQETR 1282

MOAT-B  1031 PPPAWPHEGVIIFDNVNFMYSPGGPLVLKHLTALIKSQEKVGIVGRTGAGKSSLISALFRLSE.PEGKIWIDKILTEIGLHDLRKQMSIIPQEPVLFTG  1129
             ||.:| | : :|:|||:|:|| |: |:| |:|::::::| ||||||||||||||.:|||:|: ||||.||| :||||||||:||||||||||||| ||
MRP     1283 PPSSWPQVGRVEFRNYCLRYREDLDFVLRHINVTINGGEKVGIVGRTGAGKSSLTLGLFRINESAEGEIIIDGINIAKIGLHDLRFKITIIPQDPVLFSG 1382
                                                         ─→ NBF2

MOAT-B  1130 TMRKNLDPFKEHTDEELWNALQEVQLKETIEDLPGKMDTELAESGSNFSVGQRQLVCLARAILRKNQILIIDEATANVDPRTDELIQKKIREKFAHCTVL 1229
             ::|:|||||.:.::..:..|.:::.|.|:::|||::|:.|.|   |||||||||||||||:||||:||||||||||||||||||||:|||||:||.||
MRP     1383 SLRMNLDPFSQYSDEEVWTSLELAHLKDFVSALPDKLDHECAEGGENLSVGQRQLVCLARALLRKTKILVLDEATAAVDLETDDLIQSTIRTQFEDCTVL 1482

MOAT-B  1230 TIAHRLNTIIDSDKIMVLDSGRLKEYDEPYVLLQNKESLFYKMVQQLGKAEAAALTETAKQVYFKRNYHIGHTDHMVTNTSNGQPSTLTIFETAL 1325
             ||||||||||:|:::|.|||||::.::.|.|:.::.::|:||:::|.|||: :|.   |
MRP     1483 TIAHRLNTIMDYTRVIVLDKGEIQEYGAPSDLLQQR.GLFYSMAKDAGLV 1531
```

```
   1  MKDIDIGKEY IIPSPGYRSV RERTSTSGTH RDREDSKFRR TRPLECQDAL ETAARAEGLS
  61  LDASMHSQLR ILDEEHPKGK YHHGLSALKP IRTTSKHQHP VDNAGLFSCH TFSWLSSLAR
 121  VAHKKGELSM EDVWSLSKHE SSDVNCRRLE RLWQEELNEV GPDAASLRRV VWIFCRTRLI
                    TM1                          ─────────      TM2  ───
 181  LSIVCLMITQ LAGFSGPAFM VKHLLEYTQA TESNLQYSLL LVLGLLLTEI VRSWSLALTW
      ──                                                          TM3
 241  ALNYRTGVRL RGAILTHAFK KILKLKNIKE KSLGELINIC SNDGQRMFEA AAVGSLLAGG
      ──────              TM4
 301  PVVAILGMIY NVIILGPTGF LGSAVFILFY PAHMFASRLT AYFRRKCVAA TDERVQKMNE
                                                                 TM5
 361  VLTYIKFIKH YAWVKAFSQS VQKIREEERR ILEKAGYFQG ITVGVAPIVV VIASVVTFSV
      ─          TM6       ──────────
 421  HMTLGFDLTA AQAFTVVTVF NSMTFALKVT PFSVKSLSEA SVAVDRFKSL FLMEEVHMIK
 481  NKPASPHIKI EMKNATLAWD SSHSSIQNSP KLTPKHKKDK RASRGKKEKV RQLQRTEHQA
                                                  ▶NBF1
 541  VLAEQKGHLL LDSDERPSPE EEEGKHIHLG HLRLQRTLHS IDLEIQEGKL VGICGSVGSG
                                                                 ───────
                                                                    A
 601  KTSLISAILG QMTLLEGSIA ISGTFAYVAQ QAWILNATLR DNILFGKEYD EERYNSVLNS
      ──
 661  CCLRPDLAIL PSSDLTEIGE RGANLSGGQR QRISLARALY SDRSIYILDD PLSALDAHVG
      NBF1◀              ──────          ──────
                              C                      B
 721  HHIFNSAIRK HLKSKTVLFV THQLQYLVDC DEVIFMKEGC ITERGTHEEL HNLNGDYATI
 781  FNNLLLGETP PVEINSKKET SGSQKKSQDK GPKTGSVKKE KAVKPEEGQL VQLEEKGQGS
                                                                 TM7
 841  VPWSVYGVYI QAAGGPLAFL VIMALFHLNV GSTAFSTWWL SYWIKQGSGN TTVTRGNETS
                             ──                  TM8
 901  VSDSMKDNPH MQYYASIYAL SMAVMLILKA IRGVVFVKGT LRASSRLHDE LFRRILRSPM
                                                                 TM9
 961  KFFDTTPTGR ILNRFSKDMD EVDVRLPFQA EHFIQNVILV FFCVGHIAGV FPWFLVAVGP
                TM10
1021  LVILFSVLHI VSRVLIRELK RLDNITQSPF LSHITSSIQG LATIHAYNKG QEFLHRYQEL
                                TM11                                TM12
1081  LDDNQAPFFL FTCAMRWLAV RLDLISIALI TTTGLMIVLM HGQIPPAYAG LAISYAVQLT
1141  GLFQFTVRLA SETEARFTSV ERINHYIKTL SLEAPARIKN KAPSPDWPQE GEVTFENAEM
      ──────────            ▶NBF2
1201  RYRENLPLVL KKVSFTIKPK EKIGIVGRTG SGKSSLGMAL FRLVELSGGC IKIDGVRISD
                                ──────────
                                     A
1261  IGLADLRSKL SIIPQEPVLF SGTVRSNLDP FNQYTEDQIW DALERTHMKE CIAQLPLKLE
                                                                NBF2◀
1321  SEVMENGDNF SVGERQLLCI ARALLRHCKI LILDEATAAM DTETDLLIQE TIREAFADCT
                 ──────────           ──
                     C                   B
1381  MLTIAHRLHT VLGSDRIMVL AQGQVVEFDT PSVLLSNDSS RFYAMFAAAE NKVAVKG
```

Fig. 5B

```
                                           •                          TM1
   1  MGPMDALCGS  GELGSKFWDS  NLSVHTENPD  LTPCFQNSLL  AWVPCIYLWV  ALPCYLLYLR
                              TM2
  61  HHCRGYIILS  HLSKLKMVLG  VLLWCVSWAD  LFYSFHGLVH  GRAPAPVFFV  TPLVVGVTML
      TM3                     TM4
 121  LATLLIQYER  LQGVQSSGVL  IIFWFLCVVC  AIVPFRSKIL  LAKAEGEISD  PFRFTTFYIH
                  TM5
 181  FALVLSALIL  ACFREKPPFF  SAKNVDPNPY  PETSVGFLSR  LFFWWFTKMA  IYGYRHPLEE

241  KDLWSLKEED  RSQMVVQQLL  EAWRKQEKQT  ARHKASAAPG  KNASGEDEVL  LGARPRPRKP
                              TM6
 301  SFLKALLATF  GSSFLISACF  KLIQDLLSFI  NPQLLSILIR  FISNPMAPSW  WGFLVAGLMF
                  TM7
 361  LCSMMQSLIL  QHYYHYIFVT  GVKFRTGIMG  VIYRKALVIT  NSVKRASTVG  EIVNLMSVDA
                              TM8                                  TM9
 421  QRFMDLAPFL  NLLWSAPLQI  ILAIYFLWQN  LGPSVLAGVA  FHVLLIPLNG  AVAVKMRAFQ

481  VKQMKLKDSR  IKLMSEILNG  IKVLKLYAWE  PSFLKQVEGI  RQGELQLLRT  AAYLHTTTTF
                              TM10                                 TM11
 541  TWMCSPFLVT  LITLWVYVYV  DPNNVLDAEK  AFVSVSLFNI  LRLPLNMLPQ  LISNLTQASV
                                                           NBF1
 601  SLKRIQQFLS  QEELDPQSVE  RKTISPGYAI  TIHSGTFTWA  QDLPPTLHSL  DIQVPKGALV

661  AVVGPVGCGK  SSLVSALLGE  MEKLEGKVHM  KGSVAYVPQQ  AWIQNCTLQE  NVLFGKALNP
           A
 721  KRYQQTLEAC  ALLADLEMLP  GGDQTEIGEK  GINLSGGQRQ  RVSLARAVYS  DADIFLLDDP
             NBF1                              C                       B
 781  LSAVDSHVAK  HIFDHVIGPE  GVLAGKTRVL  VTHGISFLPQ  TDFIIVLADG  QVSEMGPYPA

841  LLQRNGSFAN  FLCNYAPDED  QGHLEDSWTA  LEGAEDKEAL  LIEDTLSNHT  DLTDNDPVTY
       .
 901  VVQKQFMRQL  SALSSDGEGQ  GRPVPRRHLG  PSEKVQVTEA  KADGALTQEE  KAAIGTVELS
                              TM12                         ••
 961  VFWDYAKAVG  LCTTLAICLL  YVGQSAAAIG  AHVWLSAWTN  DAMADSRQNN  TSLRLGVYAA
                              TM13
1021  LGILQGFLVH  LAAMAMAAGG  IQAARVLHQA  LLHNKIRSPQ  SFFDTTPSGR  ILNCFSKDIY
                              TM14                                 TM15
1081  VVDEVLAPVI  LMLLNSFFKA  ISTLVVIMAS  TPLFTVVILP  LAVLYTLVQR  FYAATSRQLK
                                                                        •
1141  RLESVSRSPI  YSHFSETVTG  ASVIRAYNRS  RDFEIISDTK  VDANQRSCYP  YIISNRWLSI
      TM16                                           TM17
1201  GVEFVGNCVV  LFAALFAVIG  RSSLNPGLVG  LSVSYSLQVT  FALNWMIRMM  SDLESNIVAV
                                                           NBF2
1261  ERVKEYSKTE  TEAPWVVEGS  RPPEGWPPRG  EVEFRNYSVR  YRPGLDLVLR  DLSLHVHGGE

1321  KVGIVGRTGA  GKSSMTLCLF  RILEAAKGEI  RIDGLNVADI  GLHDLRSQLT  IIPQDPILFS
                A
1381  GTLRMNLDPF  GSYSEEDIWW  ALELSHLHTF  VSSQPAGLDF  QCSEGGENLS  VGQRQLVCLA
                                                 NBF2                C
1441  RALLRKSRIL  VLDEATAAID  LETDNLIQAT  IRTQFDTCTV  LTIAHRLNTI  MDYTRVLVLD
            B
1501  KGVVAEFDSP  AHLIAARGIF  YGMARDAGLA
```

Nucleotide Binding Fold I

```
MOAT-D  HSLDIQVPK GAEVAVVGPV GCGKSSIVSA LLAEEEKLEG KI.......  ........  ........HM KESVAYVPQG AWIQCCGLCE 707
MRP     NGETFSEPE GALVAVVGQV GCGKSSLLSA LLAEMDKVEG HV.......  ........  ........AI KESVAYVPQG AWIQCGDSLRG 724
cMOAT   VRDVNLDIMA GQLVAVIGPV GSGKSSLISA MLGEMENVHG HI.......  ........  ........TI KGTTAYVPQG AWIQNGSIKD 717
MOAT-C  HSDDLEQE SKSEGICRSL SSTTSLISA ILKQETLLEG SI.......  ........  ........AI SETFAYVAQG AWILAMLRD 641
MOAT-B  QGLSFTVRP GELLAVVGPV GCGBLAPSHG LL.......  ........  ........SV HGRIAYVSGK PWVFSGILRS 491
CFTR    KDINFKIER QCLLAVAGST ASHTLLMM IMSILEPSEG KI.......  ........  ........KH SERISFCSTF STMPGIIKE 504
SUR     SNETIREPR SGTTMIVGQV GCGKSSILLQ ABLEEHQKVSE AEFWSSLPDS EIGEDPSPER ETATDLDIRK RPVQAEIK PLLLAIVEM 785
MDR1    KGLNLKVQS GQTVALVGNS GCGKSTTVQL MQRLYDPTEG MISVDGQDIR TINVRFLREI  ........  ...IGVVSQE PVLFATTIAI 486
                         A

MOAT-D  VLFGKA.LN PKENQQTLER CATLADIEMK GGIQFEIGE KGINLSGGQR QFVSLARAVY SDADIFLLDD PLSAVESHTA KHIFDHV 793
MRP     NILFGCQ.LE EPYPRSVEQM CATLPDIEI ISETREEIGE KGVNLSGGQR QFVSLARAVY SNADIYEFDD PLSAVDAHVG KHIFENV 810
cMOAT   NILFGTE.FN EKNMQCVLEA CATLPDIEML GGELABETGE KGANLSGGQR QRISLARAVY QNADIYLLDD PLSAVDAHVG KHIFNKV 803
MOAT-C  NILFGKE.YD ERNSOLNS CGCRDAI SSSBLEIGS KGANLSGGQR QRISLARAVL SGRSVYLDDE PLSALDAHVG NHIHNSA 727
MOAT-B  NILFGKK.YE KERVEKVJIKK CALKKDIOLE EDDLEVIGD EGTFISGGQR AEVNLARAVY QDADIYLLDD PLSAVDAEMS RELPELC 577
CFTR    NIIFGVS.YD EYRYRSVIKA CQEEEFISKF AEKDNIVLGE HGITLSGGQR ARISLARAVY KDAILYLLDS PFGYLVLTE ERESC 590
SUR     NIIESP.FN KCCEKMIEEE RSICEHIDIN FHSEOQEGG RGINLSGGQF RISVARALE QHENVVELDD FSALEILS DELMQAG 871
MDR1    RYBRENVT MDEIEKAVKE ANAYDFIMKL HKFDELVD LGAQLSGGQK QRIAIARALV RNPKILLIDE ATSALTESE AVVQVAL 573
                         C               B
```

Nucleotide Binding Fold II

```
MOAT-D  RDLELHVHG GEKVGIVGRT GAGKSSMTLC LFRILEAAKG EERIDGLNVA DIGLHDLRSQ FTIIPQDIL FSGSLEMNL. ..DPFGSYAE 1392
MRP     RHINVTING GEKVGIVGRT GAGKSSLTLG LFRINESABG EITIDGININ KEGLHDLREZ ITIIPQDPVL FSGSLEMNL. ..DPFSQYSD 1396
cMOAT   RGITCDIGS METEVVGRT GAGKSSTNC LFRILAAAGG QFIIDGVDA SEGLHDLFEE ETIIPQDDIL FSGSLEMNL. ..DPNNYSL 1403
MOAT-C  KKVSFTIKP KEFISIVGRT SGKKSSLGMA LFRLVFLSGG CIKDGVRIS DEGIADLRSE IPCEPVL FSGTVSSHL. ..DPFNQBTE 1296
MOAT-B  KHLTALIKS QEKVGIVGRT GAGKSSIISA LFRLSE.FEG KIWID ILTT EEGLHDLKE MSEIPCEVL HETTMSKHL. ..DPEKEHTG 1143
SUR     KHVNALISP CEILCECRT SEKSSFSLA FEPMVDTFEG HCIDIDEA KLPITTIRSR HSLSIDDPVL FSGIRFH. ..DIERKCSD 1447
CFTR    ENIESFSP CEFTGLLIRS SEKSTILSA FLLLNT.EG EIOIDGVSWD SETMQQWRKA FGVFQKVFI FSCFEK. ..DIYEQWSB 1312
MDR1    QGLELEVKK GQTLALEGSS CGRSGTVVQL LERFYDPLAG KVLLDKEBK RLNVQWMAAH GEVSIEGIF DCSIAEEIA YGENSRVVSQ 1142
                         A

MOAT-D  EDEVWEALS HLHTFVSSCE AGLEFQCSEG EBNLSVGORQ VCLARALLE SRIVGDEA TAAIBLETIN LIG 1465
MRP     EEVTSEELE HLKDFSAEE DSLSHECABG EBNLSVGQRQ VCLARALLR THIVDDEA TAAVBLETIN LIG 1469
cMOAT   EEITKALEL HLSEEASQ LGESHVTBA GRESIEBRC LBTARALLR SKIVEDEA TAAVELETIN LIG 1476
MOAT-C  DCFDALERT EMECIACSH LRLESEVMEN DIFSVGBRQ LGIARALLR HCELIGDEA TAGMETELTL LIG 1369
MOAT-B  EETNAREV QLEETIEDEL GEMETHLABS SRFSVGORQ VCLARAIL BNORIIDEA ENVEPREIE LIS 1216
SUR     STLEEIE CELLVEKALL GGLEAIITEG EECRESCEG LERARFFVE ETSEFIMEEE ASICMAEEN ILE 1385
CFTR    QEFKVADEEV GERSVIEQFR GALEFVLVDE CVBSHEHKF MCLASSVES BAEILELDEP SEHLEPVVYQ IER 1520
MDR1    EEVREAKEF NIHAEIESE NEYSTKVGDK TQGSGIKH RIAIERALV QPHILLLEE ESLGTESEK VVS 1215
                         C               B
```

Fig. 6A

```
   1 MAAPAEPCAG QGVWNQTEPE PAATSLLSLC FLRTAGVWVP PMYLWVLGPI YLLFIHHHGR
  61 GYLRMSPLFK AKMVLGFALI VLCTSSVAVA LWKIQQGTPE APEFLIHPTV WLTTMSFAVF
 121 LIHTERKKGV QSSGVLFGYW LLCFVLPATN AAQQASGAGF QSDPVRHLST YLCLSLVVAQ
 181 FVLSCLADQP PFFPEDPQQS NPCPETGAAF PSKATFWWVS GLVWRGYRRP LRPKDLWSLG
 241 RENSSEELVS RLEKEWMRNR SAARRHNKAI AFKRKGGSGM KAPETEPFLR QEGSQWRPLL
 301 KAIWQVFHST FLLGTLSLII SDVFRFTVPK LLSLFLEFIG DPKPPAWKGY LLAVLMFLSA
 361 CLQTLFEQQN MYRLKVPQMR LRSAITGLVY RKVLALSSGS RKASAVGDVV NLVSVDVQRL
 421 TESVLYLNGL WLPLVWIVVC FVYLWQLLGP SALTAIAVFL SLLPLNFFIS KKRNHHQEEQ
 481 MRQKDSRARL TSSILRNSKT IKFHGWEGAF LDRVLGIRGQ ELGALRTSGL LFSVSLVSFQ
 541 VSTFLVALVV FAVHTLVAEN AMNAEKAFVT LTVLNILNKA QAFLPFSIHS LVQARVSFDR
                                                           ┌─NBF1
 601 LVTFLCLEEV DPGVVDSSSS GSAAGKDCIT IHSATFAWSQ ESPPCLHRIN LTVPQGCLLA
 661 VVGPVGAGKS SLLSALLGEL SKVEGFVSIE GAVAYVPQEA WVQNTSVVEN VCFGQELDPP
            A
 721 WLERVLEACA LQPDVDSFPE GIHTSIGEQG MNLSGGQKQR LSLARAVYRK AAVYLLDDPL
           NBF1─┐                        C                        B
 781 AALDAHVGQH VFNQVIGPGG LLQGTTRILV THALHILPQA DWIIVLANGA IAEMGSYQEL
 841 LQRKGALVCL LDQARQPGDR GEGETEPGTS TKDPRGTSAG RRPELRRERS IKSVPEKDRT
 901 TSEAQTEVPL DDPDRAGWPA GKDSIQYGRV KATVHLAYLR AVGTPLCLYA LFLFLCQQVA
 961 SFCRGYWLSL WADDPAVGGQ QTQAALRGGI FGLLGCLQAI GLFASMAAVL LGGARASRLL
1021 FQRLLWDVVR SPISFFERTP IGHLLNRFSK ETDTVDVDIP DKLRSLLMYA FGLLEVSLVV
1081 AVATPLATVA ILPLFLLYAG FQSLYVVSSC QLRRLESASY SSVCSHMAET FQGSTVVRAF
1141 RTQAPFVAQN NARVDESQRI SFPRLVADRW LAANVELLGN GLVFAAATCA VLSKAHLSAG
1201 LVGFSVSAAL QVTQALQWVV RNWTDLENSI VSVERMQDYA WTPKEAPWRL PTCAAQPPWP
                                   ┌─NBF2
1261 QGGQIEFRDF GLRYRPELPL AVQGVSLKIH AGEKVGIVGR TGAGKSSLAS GLLRLQEAAE
                                                        A
1321 GGIWIDGVPI AHVGLHTLRS RISIIPQDPI LFPGSLRMNL DLLQEHSDEA IWAALETVQL
                                                                  NBF2─┐
1381 KALVASLPGQ LQYKCADRGE DLSVGQKQLL CLARALLRKT QILILDEATA AVDPGTELQM
                                  C                        B
1441 QAMLGSWFAQ CTVLLIAHRL RSVMDCARVL VMDKGQVAES GSPAQLLAQK GLFYRLAQES
1501 GLV
```

Figure 9

MOAT B cDNA AND AMINO ACID SEQUENCE ENCODED THEREBY

```
    ATGCTGCCCGTGTACCAGGAGGTGAAGCCCAACCCGCTGCAGGACGCGAACATCTGCTCA
1   ------+--------+--------+--------+--------+--------+   60
    TACGACGGGCACATGGTCCTCCACTTCGGGTTGGGCGACGTCCTGCGCTTGTAGACGAGT a   M  L  P  V  Y  Q  E  V  K  P  N  P  L  Q  D  A  N  I  C  S  -

CGCGTGTTCTTCTGGTGGCTCAATCCCTTGTTTAAAATTGGCCATAAACGGAGATTAGAG
61  ------+--------+--------+--------+--------+--------+   120
    GCGCACAAGAAGACCACCGAGTTAGGGAACAAATTTTAACCGGTATTTGCCTCTAATCTC a   R  V  F  F  W  W  L  N  P  L  F  K  I  G  H  K  R  R  L  E  -

GAAGATGATATGTATTCAGTGCTGCCAGAAGACCGCTCACAGCACCTTGGAGAGGAGTTG
121 ------+--------+--------+--------+--------+--------+   180
    CTTCTACTATACATAAGTCACGACGGTCTTCTGGCGAGTGTCGTGGAACCTCTCCTCAAC a   E  D  D  M  Y  S  V  L  P  E  D  R  S  Q  H  L  G  E  E  L  -

CAAGGGTTCTGGGATAAAGAAGTTTTAAGAGCTGAGAATGACGCACAGAAGCCTTCTTTA
181 ------+--------+--------+--------+--------+--------+   240
    GTTCCCAAGACCCTATTTCTTCAAAATTCTCGACTCTTACTGCGTGTCTTCGGAAGAAAT a   Q  G  F  W  D  K  E  V  L  R  A  E  N  D  A  Q  K  P  S  L  -

ACAAGAGCAATCATAAAGTGTTACTGGAAATCTTATTTAGTTTTGGGAATTTTTACGTTA
241 ------+--------+--------+--------+--------+--------+   300
    TGTTCTCGTTAGTATTTCACAATGACCTTTAGAATAAATCAAAACCCTTAAAAATGCAAT a   T  R  A  I  I  K  C  Y  W  K  S  Y  L  V  L  G  I  F  T  L  -

ATTGAGGAAAGTGCCAAAGTAATCCAGCCCATATTTTTGGGAAAAATTATTAATTATTTT
301 ------+--------+--------+--------+--------+--------+   360
    TAACTCCTTTCACGGTTTCATTAGGTCGGGTATAAAAACCCTTTTTAATAATTAATAAAA a   I  E  E  S  A  K  V  I  Q  P  I  F  L  G  K  I  I  N  Y  F  -

GAAAATTATGATCCCATGGATTCTGTGGCTTTGAACACAGCGTACGCCTATGCCACGGTG
```

Figure 12A

```
                                                             420
361 ---------+---------+---------+---------+---------+---------+
    CTTTTAATACTAGGGTACCTAAGACACCGAAACTTGTGTCGCATGCGGATACGGTGCCAC a   E N Y D P M D S V A L N T A Y A Y A T V -

CTGACTTTTTGCACGCTCATTTTGGCTATACTGCATCACTTATATTTTTATCACGTTCAG
421 ---------+---------+---------+---------+---------+---------+  480
    GACTGAAAAACGTGCGAGTAAAACCGATATGACGTAGTGAATATAAAAATAGTGCAAGTC a   L T F C T L I L A I L H H L Y F Y H V Q -

TGTGCTGGGATGAGGTTACGAGTAGCCATGTGCCATATGATTTATCGGAAGGCACTTCGT
481 ------+--------+--------+--------+---------+---------+  540
    ACACGACCCTACTCCAATGCTCATCGGTACACGGTATACTAAATAGCCTTCCGTGAAGCA a   C A G M R L R V A M C H M I Y R K A L R -

CTTAGTAACATGGCCATGGGGAAGACAACCACAGGCCAGATAGTCAATCTGCTGTCCAAT
541 -------+--------+--------+---------+----------+---------+  600
    GAATCATTGTACCGGTACCCCTTCTGTTGGTGTCCGGTCTATCAGTTAGACGACAGGTTA a   L S N M A M G K T T T G Q I V N L L S N -

GATGTGAACAAGTTTGATCAGGTGACAGTGTTCTTACACTTCCTGTGGGCAGGACCACTG
601 -------+--------+--------+----------+---------+------+  660
    CTACACTTGTTCAAACTAGTCCACTGTCACAAGAATGTGAAGGACACCCGTCCTGGTGAC a   D V N K F D Q V T V F L H F L W A G P L -

CAGGCGATCGCAGTGACTGCCCTACTCTGGATGGAGATAGGAATATCGTGCCTTGCTGGG
661 ---------+--------+--------+---------+----------+-------+  720
    GTCCGCTAGCGTCACTGACGGGATGAGACCTACCTCTATCCTTATAGCACGGAACGACCC a   Q A I A V T A L L W M E I G I S C L A G -

ATGGCAGTTCTAATCATTCTCCTGCCCTTGCAAAGCTGTTTTGGGAAGTTGTTCTCATCA
721 --------+--------+---------+---------+-------+---------+  780
    TACCGTCAAGATTAGTAAGAGGACGGGAACGTTTCGACAAAACCCTTCAACAAGAGTAGT a   M A V L I I L L P L Q S C F G K L F S S -

CTGAGGAGTAAAACTGCAACTTTCACGGATGCCAGGATCAGGACCATGAATGAAGTTATA
781 --------+---------+---------+---------+---------+-------+  840
```

Figure 12B

```
            GACTCCTCATTTTGACGTTGAAAGTGCCTACGGTCCTAGTCCTGGTACTTACTTCAATAT a      L  R  S  K  T  A  T  F  T  D  A  R  I  R  T  M  N  E  V  I  -

ACTGGTATAAGGATAATAAAAATGTACGCCTGGGAAAAGTCATTTTCAAATCTTATTACC
841    --------+---------+---------+---------+---------+---------+    900
       TGACCATATTCCTATTATTTTTACATGCGGACCCTTTTCAGTAAAAGTTTAGAATAATGG a      T  G  I  R  I  I  K  M  Y  A  W  E  K  S  F  S  N  L  I  T  -

AATTTGAGAAAGAAGGAGATTTCCAAGATTCTGAGAAGTTCCTGCCTCAGGGGGATGAAT
901    --------+---------+---------+---------+---------+---------+    960
       TTAAACTCTTTCTTCCTCTAAAGGTTCTAAGACTCTTCAAGGACGGAGTCCCCCTACTTA a      N  L  R  K  K  E  I  S  K  I  L  R  S  S  C  L  R  G  M  N  -

TTGGCTTCGTTTTTCAGTGCAAGCAAAATCATCGTGTTTGTGACCTTCACCACCTACGTG
961    --------+---------+---------+---------+---------+---------+    1020
       AACCGAAGCAAAAAGTCACGTTCGTTTTAGTAGCACAAACACTGGAAGTGGTGGATGCAC a      L  A  S  F  F  S  A  S  K  I  I  V  F  V  T  F  T  T  Y  V  -

CTCCTCGGCAGTGTGATCACAGCCAGCCGCGTGTTCGTGGCAGTGACGCTGTATGGGGCT
1021   --------+---------+---------+---------+---------+---------+    1080
       GAGGAGCCGTCACACTAGTGTCGGTCGGCGCACAAGCACCGTCACTGCGACATACCCCGA a      L  L  G  S  V  I  T  A  S  R  V  F  V  A  V  T  L  Y  G  A  -

GTGCGGCTGACGGTTACCCTCTTCTTCCCCTCAGCCATTGAGAGGGTGTCAGAGGCAATC
1081   --------+---------+---------+---------+---------+---------+    1140
       CACGCCGACTGCCAATGGGAGAAGAAGGGGAGTCGGTAACTCTCCCACAGTCTCCGTTAG a      V  R  L  T  V  T  L  F  F  P  S  A  I  E  R  V  S  E  A  I  -

GTCAGCATCCGAAGAATCCAGACCTTTTTGCTACTTGATGAGATATCACAGCGCAACCGT
1141   --------+---------+---------+---------+---------+---------+    1200
       CAGTCGTAGGCTTCTTAGGTCTGGAAAAACGATGAACTACTCTATAGTGTCGCGTTGGCA a      V  S  I  R  R  I  Q  T  F  L  L  L  D  E  I  S  Q  R  N  R  -

CAGCTGCCGTCAGATGGTAAAAAGATGGTGCATGTGCAGGATTTTACTGCTTTTTGGGAT
1201   --------+---------+---------+---------+---------+---------+    1260
       GTCGACGGCAGTCTACCATTTTTCTACCACGTACACGTCCTAAAATGACGAAAAACCCTA
```

AAGGCATCAGAGACCCCAACTCTACAAGGCCTTTCCTTTACTGTCAGACCTGGCGAATTG
1261 --------+--------+--------+--------+--------+--------+  1320
     TTCCGTAGTCTCTGGGGTTGAGATGTTCCGGAAAGGAAATGACAGTCTGGACCGCTTAAC a    K A S E T P T L Q G L S F T V R P G E L -

TTAGCTGTGGTCGGCCCCGTGGGAGCAGGGAAGTCATCACTGTTAAGTGCCGTGCTCGGG
1321 --------+--------+--------+--------+--------+--------+  1380
     AATCGACACCAGCCGGGGCACCCTCGTCCCTTCAGTAGTGACAATTCACGGCACGAGCCC a    L A V V G P V G A G K S S L L S A V L G -

GAATTGGCCCCAAGTCACGGGCTGGTCAGCGTGCATGGAAGAATTGCCTATGTGTCTCAG
1381 --------+--------+--------+--------+--------+--------+  1440
     CTTAACCGGGGTTCAGTGCCCGACCAGTCGCACGTACCTTCTTAACGGATACACAGAGTC a    E L A P S H G L V S V H G R I A Y V S Q -

CAGCCCTGGGTGTTCTCGGGAACTCTGAGGAGTAATATTTTATTTGGGAAGAAATATGAA
1441 --------+--------+--------+--------+--------+--------+  1500
     GTCGGGACCCACAAGAGCCCTTGAGACTCCTCATTATAAAATAAACCCTTCTTTATACTT a    Q P W V F S G T L R S N I L F G K K Y E -

AAGGAACGATATGAAAAAGTCATAAAGGCTTGTGCTCTGAAAAAGGATTTACAGCTGTTG
1501 --------+--------+--------+--------+--------+--------+  1560
     TTCCTTGCTATACTTTTTCAGTATTTCCGAACACGAGACTTTTTCCTAAATGTCGACAAC a    K E R Y E K V I K A C A L K K D L Q L L -

GAGGATGGTGATCTGACTGTGATAGGAGATCGGGGAACCACGCTGAGTGGAGGGCAGAAA
1561 --------+--------+--------+--------+--------+--------+  1620
     CTCCTACCACTAGACTGACACTATCCTCTAGCCCCTTGGTGCGACTCACCTCCCGTCTTT a    E D G D L T V I G D R G T T L S G G Q K -

GCACGGGTAAACCTTGCAAGAGCAGTGTATCAAGATGCTGACATCTATCTCCTGGACGAT
1621 --------+--------+--------+--------+--------+--------+  1680
     CGTGCCCATTTGGAACGTTCTCGTCACATAGTTCTACGACTGTAGATAGAGGACCTGCTA
```

CCTCTCAGTGCAGTAGATGCGGAAGTTAGCAGACACTTGTTCGAACTGTGTATTTGTCAA
1681 ------+--------+--------+--------+--------+--------+ 1740
    GGAGAGTCACGTCATCTACGCCTTCAATCGTCTGTGAACAAGCTTGACACATAAACAGTT a   P L S A V D A E V S R H L F E L C I C Q  -

ATTTTGCATGAGAAGATCACAATTTTAGTGACTCATCAGTTGCAGTACCTCAAAGCTGCA
1741 ------+--------+--------+--------+--------+--------+ 1800
    TAAAACGTACTCTTCTAGTGTTAAAATCACTGAGTAGTCAACGTCATGGAGTTTCGACGT a   I L H E K I T I L V T H Q L Q Y L K A A  -

AGTCAGATTCTGATATTGAAAGATGGTAAAATGGTGCAGAAGGGGACTTACACTGAGTTC
1801 ------+--------+--------+--------+--------+--------+ 1860
    TCAGTCTAAGACTATAACTTTCTACCATTTTACCACGTCTTCCCCTGAATGTGACTCAAG a   S Q I L I L K D G K M V Q K G T Y T E F  -

CTAAAATCTGGTATAGATTTTGGCTCCCTTTTAAAGAAGGATAATGAGGAAAGTGAACAA
1861 ------+--------+--------+--------+--------+--------+ 1920
    GATTTTAGACCATATCTAAAACCGAGGGAAAATTTCTTCCTATTACTCCTTTCACTTGTT a   L K S G I D F G S L L K K D N E E S E Q  -

CCTCCAGTTCCAGGAACTCCCACACTAAGGAATCGTACCTTCTCAGAGTCTTCGGTTTGG
1921 ------+--------+--------+--------+--------+--------+ 1980
    GGAGGTCAAGGTCCTTGAGGGTGTGATTCCTTAGCATGGAAGAGTCTCAGAAGCCAAACC a   P P V P G T P T L R N R T F S E S S V W  -

TCTCAACAATCTTCTAGACCCTCCTTGAAAGATGGTGCTCTGGAGAGCCAAGATACAGAG
1981 ------+--------+--------+--------+--------+--------+ 2040
    AGAGTTGTTAGAAGATCTGGGAGGAACTTTCTACCACGAGACCTCTCGGTTCTATGTCTC a   S Q Q S S R P S L K D G A L E S Q D T E  -

AATGTCCCAGTTACACTATCAGAGGAGAACCGTTCTGAAGGAAAAGTTGGTTTTCAGGCC
2041 ------+--------+--------+--------+--------+--------+ 2100
    TTACAGGGTCAATGTGATAGTCTCCTCTTGGCAAGACTTCCTTTTCAACCAAAAGTCCGG a   N V P V T L S E E N R S E G K V G F Q A
```

Figure 12E

```
        TATAAGAATTACTTCAGAGCTGGTGCTCACTGGATTGTCTTCATTTTCCTTATTCTCCTA
2101 --------+---------+---------+---------+---------+---------+ 2160
        ATATTCTTAATGAAGTCTCGACCACGAGTGACCTAACAGAAGTAAAAGGAATAAGAGGAT a       Y  K  N  Y  F  R  A  G  A  H  W  I  V  F  I  F  L  I  L  L   -

AACACTGCAGCTCAGGTTGCCTATGTGCTTCAAGATTGGTGGCTTTCATACTGGGCAAAC
2161 --------+---------+---------+---------+---------+---------+ 2220
        TTGTGACGTCGAGTCCAACGGATACACGAAGTTCTAACCACCGAAAGTATGACCCGTTTG a       N  T  A  A  Q  V  A  Y  V  L  Q  D  W  W  L  S  Y  W  A  N   -

AAACAAAGTATGCTAAATGTCACTGTAAATGGAGGAGGAAATGTAACCGAGAAGCTAGAT
2221 --------+---------+---------+---------+---------+---------+ 2280
        TTTGTTTCATACGATTTACAGTGACATTTACCTCCTCCTTTACATTGGCTCTTCGATCTA a       K  Q  S  M  L  N  V  T  V  N  G  G  G  N  V  T  E  K  L  D   -

CTTAACTGGTACTTAGGAATTTATTCAGGTTTAACTGTAGCTACCGTTCTTTTTGGCATA
2281 --------+---------+---------+---------+---------+---------+ 2340
        GAATTGACCATGAATCCTTAAATAAGTCCAAATTGACATCGATGGCAAGAAAAACCGTAT a       L  N  W  Y  L  G  I  Y  S  G  L  T  V  A  T  V  L  F  G  I   -

GCAAGATCTCTATTGGTATTCTACGTCCTTGTTAACTCTTCACAAACTTTGCACAACAAA
2341 --------+---------+---------+---------+---------+---------+ 2400
        CGTTCTAGAGATAACCATAAGATGCAGGAACAATTGAGAAGTGTTTGAAACGTGTTGTTT a       A  R  S  L  L  V  F  Y  V  L  V  N  S  S  Q  T  L  H  N  K   -

ATGTTTGAGTCAATTCTGAAAGCTCCGGTATTATTCTTTGATAGAAATCCAATAGGAAGA
2401 --------+---------+---------+---------+---------+---------+ 2460
        TACAAACTCAGTTAAGACTTTCGAGGCCATAATAAGAAACTATCTTTAGGTTATCCTTCT a       M  F  E  S  I  L  K  A  P  V  L  F  F  D  R  N  P  I  G  R   -

ATTTTAAATCGTTTCTCCAAAGACATTGGACACTTGGATGATTTGCTGCCGCTGACGTTT
2461 --------+---------+---------+---------+---------+---------+ 2520
        TAAAATTTAGCAAAGAGGTTTCTGTAACCTGTGAACCTACTAAACGACGGCGACTGCAAA a       I  L  N  R  F  S  K  D  I  G  H  L  D  D  L  L  P  L  T  F   -
```

Figure 12F

```
     TTAGATTTCATCCAGACATTGCTACAAGTGGTTGGTGTGGTCTCTGTGGCTGTGGCCGTG
2521 ---------+---------+---------+---------+---------+---------+ 2580
     AATCTAAAGTAGGTCTGTAACGATGTTCACCAACCACACCAGAGACACCGACACCGGCAC
``` a    L D F I Q T L L Q V V G V V S V A V A V  -

```
     ATTCCTTGGATCGCAATACCCTTGGTTCCCCTTGGAATCATTTTCATTTTTCTTCGGCGA
2581 ---------+---------+---------+---------+---------+---------+ 2640
     TAAGGAACCTAGCGTTATGGGAACCAAGGGGAACCTTAGTAAAAGTAAAAAGAAGCCGCT
``` a    I P W I A I P L V P L G I I F I F L R R  -

```
     TATTTTTTGGAAACGTCAAGAGATGTGAAGCGCCTGGAATCTACAACTCGGAGTCCAGTG
2641 ---------+---------+---------+---------+---------+---------+ 2700
     ATAAAAAACCTTTGCAGTTCTCTACACTTCGCGGACCTTAGATGTTGAGCCTCAGGTCAC
``` a    Y F L E T S R D V K R L E S T T R S P V  -

```
     TTTTCCCACTTGTCATCTTCTCCAGGGGCTCTGGACCATCCGGGCATACAAAGCAGAA
2701 ---------+---------+---------+---------+---------+---------+ 2760
     AAAAGGGTGAACAGTAGAAGAGAGGTCCCCGAGACCTGGTAGGCCCGTATGTTTCGTCTT
``` a    F S H L S S S L Q G L W T I R A Y K A E  -

```
     GAGAGGTGTCAGGAACTGTTTGATGCACACCAGGATTTACATTCAGAGGCTTGGTTCTTG
2761 ---------+---------+---------+---------+---------+---------+ 2820
     CTCTCCACAGTCCTTGACAAACTACGTGTGGTCCTAAATGTAAGTCTCCGAACCAAGAAC
``` a    E R C Q E L F D A H Q D L H S E A W F L  -

```
     TTTTTGACAACGTCCCGCTGGTTCGCCGTCCGTCTGGATGCCATCTGTGCCATGTTTGTC
2821 ---------+---------+---------+---------+---------+---------+ 2880
     AAAAACTGTTGCAGGGCGACCAAGCGGCAGGCAGACCTACGGTAGACACGGTACAAACAG
``` a    F L T T S R W F A V R L D A I C A M F V  -

```
     ATCATCGTTGCCTTTGGGTCCCTGATTCTGGCAAAAACTCTGGATGCCGGGCAGGTTGGT
2881 ---------+---------+---------+---------+---------+---------+ 2940
     TAGTAGCAACGGAAACCCAGGGACTAAGACCGTTTTTGAGACCTACGGCCCGTCCAACCA
``` a    I I V A F G S L I L A K T L D A G Q V G  -

```
     TTGGCACTGTCCTATGCCCTCACGCTCATGGGGATGTTTCAGTGGTGTGTTCGACAAAGT
```

Figure 12G

```
                   2941 ---------+---------+---------+---------+---------+---------+  3000
                       AACCGTGACAGGATACGGGAGTGCGAGTACCCCTACAAAGTCACCACACAAGCTGTTTCA a       L A L S Y A L T L M G M F Q W C V R Q S -

GCTGAAGTTGAGAATATGATGATCTCAGTAGAAAGGGTCATTGAATACACAGACCTTGAA
                   3001 ---------+---------+---------+---------+---------+---------+  3060
                       CGACTTCAACTCTTATACTACTAGAGTCATCTTTCCCAGTAACTTATGTGTCTGGAACTT a       A E V E N M M I S V E R V I E Y T D L E -

AAAGAAGCACCTTGGGAATATCAGAAACGCCCACCACCAGCCTGGCCCCATGAAGGAGTG
                   3061 ---------+---------+---------+---------+---------+---------+  3120
                       TTTCTTCGTGGAACCCTTATAGTCTTTGCGGGTGGTGGTCGGACCGGGGTACTTCCTCAC a       K E A P W E Y Q K R P P P A W P H E G V -

ATAATCTTTGACAATGTGAACTTCATGTACAGTCCAGGTGGGCCTCTGGTACTGAAGCAT
                   3121 ---------+---------+---------+---------+---------+---------+  3180
                       TATTAGAAACTGTTACACTTGAAGTACATGTCAGGTCCACCCGGAGACCATGACTTCGTA a       I I F D N V N F M Y S P G G P L V L K H -

CTGACAGCACTCATTAAATCACAAGAAAAGGTTGGCATTGTGGGAAGAACCGGAGCTGGA
                   3181 ---------+---------+---------+---------+---------+---------+  3240
                       GACTGTCGTGAGTAATTTAGTGTTCTTTTCCAACCGTAACACCCTTCTTGGCCTCGACCT a       L T A L I K S Q E K V G I V G R T G A G -

AAAAGTTCCCTCATCTCAGCCCTTTTTAGATTGTCAGAACCCGAAGGTAAAATTTGGATT
                   3241 ---------+---------+---------+---------+---------+---------+  3300
                       TTTTCAAGGGAGTAGAGTCGGGAAAAATCTAACAGTCTTGGGCTTCCATTTTAAACCTAA a       K S S L I S A L F R L S E P E G K I W I -

GATAAGATCTTGACAACTGAAATTGGACTTCACGATTTAAGGAAGAAAATGTCAATCATA
                   3301 ---------+---------+---------+---------+---------+---------+  3360
                       CTATTCTAGAACTGTTGACTTTAACCTGAAGTGCTAAATTCCTTCTTTTACAGTTAGTAT a       D K I L T T E I G L H D L R K K M S I I -

CCTCAGGAACCTGTTTTGTTCACTGGAACAATGAGGAAAAACCTGGATCCCTTTAAGGAG
                   3361 ---------+---------+---------+---------+---------+---------+  3420
```

Figure 12H

```
                GGAGTCCTTGGACAAAACAAGTGACCTTGTTACTCCTTTTTGGACCTAGGGAAATTCCTC a    P  Q  E  P  V  L  F  T  G  T  M  R  K  N  L  D  P  F  K  E  -

CACACGGATGAGGAACTGTGGAATGCCTTACAAGAGGTACAACTTAAAGAAACCATTGAA
        3421 --------+--------+---------+---------+---------+---------+   3480
                GTGTGCCTACTCCTTGACACCTTACGGAATGTTCTCCATGTTGAATTTCTTTGGTAACTT a    H  T  D  E  E  L  W  N  A  L  Q  E  V  Q  L  K  E  T  I  E  -

GATCTTCCTGGTAAAATGGATACTGAATTAGCAGAATCAGGATCCAATTTTAGTGTTGGA
        3481 --------+---------+---------+----------+----------+---------+   3540
                CTAGAAGGACCATTTTACCTATGACTTAATCGTCTTAGTCCTAGGTTAAAATCACAACCT a    D  L  P  G  K  M  D  T  E  L  A  E  S  G  S  N  F  S  V  G  -

CAAAGACAACTGGTGTGCCTTGCCAGGGCAATTCTCAGGAAAAATCAGATATTGATTATT
        3541 ---------+---------+---------+----------+---------+---------+   3600
                GTTTCTGTTGACCACACGGAACGGTCCCGTTAAGAGTCCTTTTTAGTCTATAACTAATAA a    Q  R  Q  L  V  C  L  A  R  A  I  L  R  K  N  Q  I  L  I  I  -

GATGAAGCGACGGCAAATGTGGATCCAAGAACTGATGAGTTAATACAAAAAAAAATCCGG
        3601 ---------+---------+----------+----------+----------+---------+   3660
                CTACTTCGCTGCCGTTTACACCTAGGTTCTTGACTACTCAATTATGTTTTTTTTTAGGCC a    D  E  A  T  A  N  V  D  P  R  T  D  E  L  I  Q  K  K  I  R  -

GAGAAATTTGCCCACTGCACCGTGCTAACCATTGCACACAGATTGAACACCATTATTGAC
        3661 ---------+---------+----------+----------+---------+--------+   3720
                CTCTTTAAACGGGTGACGTGGCACGATTGGTAACGTGTGTCTAACTTGTGGTAATAACTG a    E  K  F  A  H  C  T  V  L  T  I  A  H  R  L  N  T  I  I  D  -

AGCGACAAGATAATGGTTTTAGATTCAGGAAGACTGAAAGAATATGATGAGCCGTATGTT
        3721 --------+---------+---------+----------+----------+---------+   3780
                TCGCTGTTCTATTACCAAAATCTAAGTCCTTCTGACTTTCTTATACTACTCGGCATACAA a    S  D  K  I  M  V  L  D  S  G  R  L  K  E  Y  D  E  P  Y  V  -

TTGCTGCAAAATAAAGAGAGCCTATTTTACAAGATGGTGCAACAACTGGGCAAGGCAGAA
        3781 --------+---------+---------+----------+----------+---------+   3840
                AACGACGTTTTATTTCTCTCGGATAAAATGTTCTACCACGTTGTTGACCCGTTCCGTCTT
```

Figure 12I a   L L Q N K E S L F Y K M V Q Q L G K A E -

```
    GCCGCTGCCCTCACTGAAACAGCAAAACAGGTATACTTCAAAAGAAATTATCCACATATT
3841 ——————+———————+———————+———————+—————————+—————————+   3900
    CGGCGACGGGAGTGACTTTGTCGTTTTGTCCATATGAAGTTTTCTTTAATAGGTGTATAA
``` a   A A A L T E T A K Q V Y F K R N Y P H I -

```
    GGTCACACTGACCACATGGTTACAAACACTTCCAATGGACAGCCCTCGACCTTAACTATT
3901 ——————+———————+———————+———————+—————————+—————————+   3960
    CCAGTGTGACTGGTGTACCAATGTTTGTGAAGGTTACCTGTCGGGAGCTGGAATTGATAA
``` a   G H T D H M V T N T S N G Q P S T L T I -

```
    TTCGAGACAGCACTG
3961 ———————+——— 3975
    AAGCTCTGTCGTGAC
``` a   F E T A L -

Figure 12J

MOAT C cDNA AND AMINO ACID SEQUENCE ENCODED THEREBY

```
    ATGAAGGATATCGACATAGGAAAAGAGTATATCATCCCCAGTCCTGGGTATAGAAGTGTG
1   ---------+---------+---------+---------+---------+---------+   60
    TACTTCCTATAGCTGTATCCTTTTCTCATATAGTAGGGGTCAGGACCCATATCTTCACAC
``` a    M K D I D I G K E Y I I P S P G Y R S V -

```
    AGGGAGAGAACCAGCACTTCTGGGACGCACAGAGACCGTGAAGATTCCAAGTTCAGGAGA
61  ---------+---------+---------+---------+---------+---------+  120
    TCCCTCTCTTGGTCGTGAAGACCCTGCGTGTCTCTGGCACTTCTAAGGTTCAAGTCCTCT
``` a    R E R T S T S G T H R D R E D S K F R R -

```
    ACTCGACCGTTGGAATGCCAAGATGCCTTGGAAACAGCAGCCCGAGCCGAGGGCCTCTCT
121 ---------+---------+---------+---------+---------+---------+  180
    TGAGCTGGCAACCTTACGGTTCTACGGAACCTTTGTCGTCGGGCTCGGCTCCCGGAGAGA
``` a    T R P L E C Q D A L E T A A R A E G L S -

```
    CTTGATGCCTCCATGCATTCTCAGCTCAGAATCCTGGATGAGGAGCATCCCAAGGGAAAG
181 ---------+---------+---------+---------+---------+---------+  240
    GAACTACGGAGGTACGTAAGAGTCGAGTCTTAGGACCTACTCCTCGTAGGGTTCCCTTTC
``` a    L D A S M H S Q L R I L D E E H P K G K -

```
    TACCATCATGGCTTGAGTGCTCTGAAGCCCATCCGGACTACTTCCAAACACCAGCACCCA
241 ---------+---------+---------+---------+---------+---------+  300
    ATGGTAGTACCGAACTCACGAGACTTCGGGTAGGCCTGATGAAGGTTTGTGGTCGTGGGT
``` a    Y H H G L S A L K P I R T T S K H Q H P -

```
    GTGGACAATGCTGGGCTTTTTTCCTGTATGACTTTTTCGTGGCTTTCTTCTCTGGCCCGT
301 ---------+---------+---------+---------+---------+---------+  360
    CACCTGTTACGACCCGAAAAAAGGACATACTGAAAAAGCACCGAAAGAAGAGACCGGGCA
``` a    V D N A G L F S C M T F S W L S S L A R -

```
    GTGGCCCACAAGAAGGGGGAGCTCTCAATGGAAGACGTGTGGTCTCTGTCCAAGCACGAG
```

Figure 13A

```
361 ---------+---------+---------+---------+---------+---------+ 420
    CACCGGGTGTTCTTCCCCCTCGAGAGTTACCTTCTGCACACCAGAGACAGGTTCGTGCTC
``` a    V  A  H  K  K  G  E  L  S  M  E  D  V  W  S  L  S  K  H  E  -

```
    TCTTCTGACGTGAACTGCAGAAGACTAGAGAGACTGTGGCAAGAAGAGCTGAATGAAGTT
421 ---------+---------+---------+---------+---------+---------+ 480
    AGAAGACTGCACTTGACGTCTTCTGATCTCTCTGACACCGTTCTTCTCGACTTACTTCAA
``` a    S  S  D  V  N  C  R  R  L  E  R  L  W  Q  E  E  L  N  E  V  -

```
    GGGCCAGACGCTGCTTCCCTGCGAAGGGTTGTGTGGATCTTCTGCCGCACCAGGCTCATC
481 ---------+---------+---------+---------+---------+---------+ 540
    CCCGGTCTGCGACGAAGGGACGCTTCCCAACACACCTAGAAGACGGCGTGGTCCGAGTAG
``` a    G  P  D  A  A  S  L  R  R  V  V  W  I  F  C  R  T  R  L  I  -

```
    CTGTCCATCGTGTGCCTGATGATCACGCAGCTGGCTGGCTTCAGTGGACCAGCCTTCATG
541 ---------+---------+---------+---------+---------+---------+ 600
    GACAGGTAGCACACGGACTACTAGTGCGTCGACCGACCGAAGTCACCTGGTCGGAAGTAC
``` a    L  S  I  V  C  L  M  I  T  Q  L  A  G  F  S  G  P  A  F  M  -

```
    GTGAAACACCTCTTGGAGTATACCCAGGCAACAGAGTCTAACCTGCAGTACAGCTTGTTG
601 ---------+---------+---------+---------+---------+---------+ 660
    CACTTTGTGGAGAACCTCATATGGGTCCGTTGTCTCAGATTGGACGTCATGTCGAACAAC
``` a    V  K  H  L  L  E  Y  T  Q  A  T  E  S  N  L  Q  Y  S  L  L  -

```
    TTAGTGCTGGGCCTCCTCCTGACGGAAATCGTGCGGTCTTGGTCGCTTGCACTGACTTGG
661 ---------+---------+---------+---------+---------+---------+ 720
    AATCACGACCCGGAGGAGGACTGCCTTTAGCACGCCAGAACCAGCGAACGTGACTGAACC
``` a    L  V  L  G  L  L  L  T  E  I  V  R  S  W  S  L  A  L  T  W  -

```
    GCATTGAATTACCGAACCGGTGTCCGCTTGCGGGGGGCCATCCTAACCATGGCATTTAAG
721 ---------+---------+---------+---------+---------+---------+ 780
    CGTAACTTAATGGCTTGGCCACAGGCGAACGCCCCCCGGTAGGATTGGTACCGTAAATTC
``` a    A  L  N  Y  R  T  G  V  R  L  R  G  A  I  L  T  M  A  F  K  -

```
    AAGATCCTTAAGTTAAAGAACATTAAAGAGAAATCCCTGGGTGAGCTCATCAACATTTGC
781 ---------+---------+---------+---------+---------+---------+ 840
```

Figure 13B

```
                TTCTAGGAATTCAATTTCTTGTAATTTCTCTTTAGGGACCCACTCGAGTAGTTGTAAACG a        K  I  L  K  L  K  N  I  K  E  K  S  L  G  E  L  I  N  I  C  -

TCCAACGATGGGCAGAGAATGTTTGAGGCAGCAGCCGTTGGCAGCCTGCTGGCTGGAGGA
841  --------+---------+---------+---------+---------+---------+   900
         AGGTTGCTACCCGTCTCTTACAAACTCCGTCGTCGGCAACCGTCGGACGACCGACCTCCT a        S  N  D  G  Q  R  M  F  E  A  A  A  V  G  S  L  L  A  G  G  -

CCCGTTGTTGCCATCTTAGGCATGATTTATAATGTAATTATTCTGGGACCAACAGGCTTC
901  --------+---------+---------+---------+---------+---------+   960
         GGGCAACAACGGTAGAATCCGTACTAAATATTACATTAATAAGACCCTGGTTGTCCGAAG a        P  V  V  A  I  L  G  M  I  Y  N  V  I  I  L  G  P  T  G  F  -

CTGGGATCAGCTGTTTTTATCCTCTTTTACCCAGCAATGATGTTTGCATCACGGCTCACA
961  --------+---------+---------+---------+---------+---------+   1020
         GACCCTAGTCGACAAAAATAGGAGAAAATGGGTCGTTACTACAAACGTAGTGCCGAGTGT a        L  G  S  A  V  F  I  L  F  Y  P  A  M  M  F  A  S  R  L  T  -

GCATATTTCAGGAGAAAATGCGTGGCCGCCACGGATGAACGTGTCCAGAAGATGAATGAA
1021 --------+---------+---------+---------+---------+---------+   1080
         CGTATAAAGTCCTCTTTTACGCACCGGCGGTGCCTACTTGCACAGGTCTTCTACTTACTT a        A  Y  F  R  R  K  C  V  A  A  T  D  E  R  V  Q  K  M  N  E  -

GTTCTTACTTACATTAAATTTATCAAAATGTATGCCTGGGTCAAAGCATTTTCTCAGAGT
1081 --------+---------+---------+---------+---------+---------+   1140
         CAAGAATGAATGTAATTTAAATAGTTTTACATACGGACCCAGTTTCGTAAAAGAGTCTCA a        V  L  T  Y  I  K  F  I  K  M  Y  A  W  V  K  A  F  S  Q  S  -

GTTCAGAAAATCCGCGAGGAGGAGCGTCGGATATTGGAAAAAGCCGGGTACTTCCAGGGT
1141 --------+---------+---------+---------+---------+---------+   1200
         CAAGTCTTTTAGGCGCTCCTCCTCGCAGCCTATAACCTTTTTCGGCCCATGAAGGTCCCA a        V  Q  K  I  R  E  E  E  R  R  I  L  E  K  A  G  Y  F  Q  G  -

ATCACTGTGGGTGTGGCTCCCATTGTGGTGGTGATTGCCAGCGTGGTGACCTTCTCTGTT
1201 --------+---------+---------+---------+---------+---------+   1260
         TAGTGACACCCACACCGAGGGTAACACCACCACTAACGGTCGCACCACTGGAAGAGACAA
```

Figure 13C a  I T V G V A P I V V V I A S V V T F S V -

```
     CATATGACCCTGGGCTTCGATCTGACAGCAGCACAGGCTTTCACAGTGGTGACAGTCTTC
1261 --------+--------+--------+--------+--------+--------+ 1320
     GTATACTGGGACCCGAAGCTAGACTGTCGTCGTGTCCGAAAGTGTCACCACTGTCAGAAG
``` a  H M T L G F D L T A A Q A F T V V T V F -

```
     AATTCCATGACTTTTGCTTTGAAAGTAACACCGTTTTCAGTAAAGTCCCTCTCAGAAGCC
1321 --------+--------+--------+--------+--------+--------+ 1380
     TTAAGGTACTGAAAACGAAACTTTCATTGTGGCAAAAGTCATTTCAGGGAGAGTCTTCGG
``` a  N S M T F A L K V T P F S V K S L S E A -

```
     TCAGTGGCTGTTGACAGATTTAAGAGTTTGTTTCTAATGGAAGAGGTTCACATGATAAAG
1381 --------+--------+--------+--------+--------+--------+ 1440
     AGTCACCGACAACTGTCTAAATTCTCAAACAAAGATTACCTTCTCCAAGTGTACTATTTC
``` a  S V A V D R F K S L F L M E E V H M I K -

```
     AACAAACCAGCCAGTCCTCACATCAAGATAGAGATGAAAAATGCCACCTTGGCATGGGAC
1441 --------+--------+--------+--------+--------+--------+ 1500
     TTGTTTGGTCGGTCAGGAGTGTAGTTCTATCTCTACTTTTTACGGTGGAACCGTACCCTG
``` a  N K P A S P H I K I E M K N A T L A W D -

```
     TCCTCCCACTCCAGTATCCAGAACTCGCCCAAGCTGACCCCCAAAATGAAAAAAGACAAG
1501 --------+--------+--------+--------+--------+--------+ 1560
     AGGAGGGTGAGGTCATAGGTCTTGAGCGGGTTCGACTGGGGGTTTTACTTTTTTCTGTTC
``` a  S S H S S I Q N S P K L T P K M K K D K -

```
     AGGGCTTCCAGGGGCAAGAAAGAGAAGGTGAGGCAGCTGCAGCGCACTGAGCATCAGGCG
1561 --------+--------+--------+--------+--------+--------+ 1620
     TCCCGAAGGTCCCCGTTCTTTCTCTTCCACTCCGTCGACGTCGCGTGACTCGTAGTCCGC
``` a  R A S R G K K E K V R Q L Q R T E H Q A -

```
     GTGCTGGCAGAGCAGAAAGGCCACCTCCTCCTGGACAGTGACGAGCGGCCCAGTCCCGAA
1621 --------+--------+--------+--------+--------+--------+ 1680
     CACGACCGTCTCGTCTTTCCGGTGGAGGAGGACCTGTCACTGCTCGCCGGGTCAGGGCTT
```

Figure 13D a    V L A E Q K G H L L L D S D E R P S P E  -

```
     GAGGAAGAAGGCAAGCACATCCACCTGGGCCACCTGCGCTTACAGAGGACACTGCACAGC
1681 ———+———+———+———+———+———+ 1740
     CTCCTTCTTCCGTTCGTGTAGGTGGACCCGGTGGACGCGAATGTCTCCTGTGACGTGTCG
``` a    E E E G K H I H L G H L R L Q R T L H S  -

```
     ATCGATCTGGAGATCCAAGAGGGTAAACTGGTTGGAATCTGCGGCAGTGTGGGAAGTGGA
1741 ———+———+———+———+———+———+ 1800
     TAGCTAGACCTCTAGGTTCTCCCATTTGACCAACCTTAGACGCCGTCACACCCTTCACCT
``` a    I D L E I Q E G K L V G I C G S V G S G  -

```
     AAAACCTCTCTCATTTCAGCCATTTTAGGCCAGATGACGCTTCTAGAGGGCAGCATTGCA
1801 ———+———+———+———+———+———+ 1860
     TTTTGGAGAGAGTAAAGTCGGTAAAATCCGGTCTACTGCGAAGATCTCCCGTCGTAACGT
``` a    K T S L I S A I L G Q M T L L E G S I A  -

```
     ATCAGTGGAACCTTCGCTTATGTGGCCCAGCAGGCCTGGATCCTCAATGCTACTCTGAGA
1861 ———+———+———+———+———+———+ 1920
     TAGTCACCTTGGAAGCGAATACACCGGGTCGTCCGGACCTAGGAGTTACGATGAGACTCT
``` a    I S G T F A Y V A Q Q A W I L N A T L R  -

```
     GACAACATCCTGTTTGGGAAGGAATATGATGAAGAAAGATACAACTCTGTGCTGAACAGC
1921 ———+———+———+———+———+———+ 1980
     CTGTTGTAGGACAAACCCTTCCTTATACTACTTCTTTCTATGTTGAGACACGACTTGTCG
``` a    D N I L F G K E Y D E E R Y N S V L N S  -

```
     TGCTGCCTGAGGCCTGACCTGGCCATTCTTCCCAGCAGCGACCTGACGGAGATTGGAGAG
1981 ———+———+———+———+———+———+ 2040
     ACGACGGACTCCGGACTGGACCGGTAAGAAGGGTCGTCGCTGGACTGCCTCTAACCTCTC
``` a    C C L R P D L A I L P S S D L T E I G E  -

```
     CGAGGAGCCAACCTGAGCGGTGGGCAGCGCCAGAGGATCAGCCTTGCCCGGGCCTTGTAT
2041 ———+———+———+———+———+———+ 2100
     GCTCCTCGGTTGGACTCGCCACCCGTCGCGGTCTCCTAGTCGGAACGGGCCCGGAACATA
``` a    R G A N L S G G Q R Q R I S L A R A L Y  -

Figure 13E

```
         AGTGACAGGAGCATCTACATCCTGGACGACCCCCTCAGTGCCTTAGATGCCCATGTGGGC
    2101 --------+--------+--------+--------+--------+--------+ 2160
         TCACTGTCCTCGTAGATGTAGGACCTGCTGGGGGAGTCACGGAATCTACGGGTACACCCG a          S  D  R  S  I  Y  I  L  D  D  P  L  S  A  L  D  A  H  V  G  -

AACCACATCTTCAATAGTGCTATCCGGAAACATCTCAAGTCCAAGACAGTTCTGTTTGTT
    2161 --------+--------+--------+--------+--------+--------+ 2220
         TTGGTGTAGAAGTTATCACGATAGGCCTTTGTAGAGTTCAGGTTCTGTCAAGACAAACAA a          N  H  I  F  N  S  A  I  R  K  H  L  K  S  K  T  V  L  F  V  -

ACCCACCAGTTACAGTACCTGGTTGACTGTGATGAAGTGATCTTCATGAAAGAGGGCTGT
    2221 --------+--------+--------+--------+--------+--------+ 2280
         TGGGTGGTCAATGTCATGGACCAACTGACACTACTTCACTAGAAGTACTTTCTCCCGACA a          T  H  Q  L  Q  Y  L  V  D  C  D  E  V  I  F  M  K  E  G  C  -

ATTACGGAAAGAGGCACCCATGAGGAACTGATGAATTTAAATGGTGACTATGCTACCATT
    2281 --------+--------+--------+--------+--------+--------+ 2340
         TAATGCCTTTCTCCGTGGGTACTCCTTGACTACTTAAATTTACCACTGATACGATGGTAA a          I  T  E  R  G  T  H  E  E  L  M  N  L  N  G  D  Y  A  T  I  -

TTTAATAACCTGTTGCTGGGAGAGACACCGCCAGTTGAGATCAATTCAAAAAAGGAAACC
    2341 --------+--------+--------+--------+--------+--------+ 2400
         AAATTATTGGACAACGACCCTCTCTGTGGCGGTCAACTCTAGTTAAGTTTTTTCCTTTGG a          F  N  N  L  L  L  G  E  T  P  P  V  E  I  N  S  K  K  E  T  -

AGTGGTTCACAGAAGAAGTCACAAGACAAGGGTCCTAAAACAGGATCAGTAAAGAAGGAA
    2401 --------+--------+--------+--------+--------+--------+ 2460
         TCACCAAGTGTCTTCTTCAGTGTTCTGTTCCCAGGATTTTGTCCTAGTCATTTCTTCCTT a          S  G  S  Q  K  K  S  Q  D  K  G  P  K  T  G  S  V  K  K  E  -

AAAGCAGTAAAGCCAGAGGAAGGGCAGCTTGTGCAGCTGGAAGAGAAAGGGCAGGGTTCA
    2461 --------+--------+--------+--------+--------+--------+ 2520
         TTTCGTCATTTCGGTCTCCTTCCCGTCGAACACGTCGACCTTCTCTTTCCCGTCCCAAGT a          K  A  V  K  P  E  E  G  Q  L  V  Q  L  E  E  K  G  Q  G  S  -
```

Figure 13F

```
       GTGCCCTGGTCAGTATATGGTGTCTACATCCAGGCTGCTGGGGGCCCCTTGGCATTCCTG
  2521 --------+--------+--------+--------+--------+--------+   2580
       CACGGGACCAGTCATATACCACAGATGTAGGTCCGACGACCCCCGGGGAACCGTAAGGAC
``` a       V  P  W  S  V  Y  G  V  Y  I  Q  A  A  G  G  P  L  A  F  L  -

```
       GTTATTATGGCCCTTTTCATGCTGAATGTAGGCAGCACCGCCTTCAGCACCTGGTGGTTG
  2581 --------+--------+--------+--------+--------+--------+   2640
       CAATAATACCGGGAAAAGTACGACTTACATCCGTCGTGGCGGAAGTCGTGGACCACCAAC
``` a       V  I  M  A  L  F  M  L  N  V  G  S  T  A  F  S  T  W  W  L  -

```
       AGTTACTGGATCAAGCAAGGAAGCGGGAACACCACTGTGACTCGAGGGAACGAGACCTCG
  2641 --------+--------+--------+--------+--------+--------+   2700
       TCAATGACCTAGTTCGTTCCTTCGCCCTTGTGGTGACACTGAGCTCCCTTGCTCTGGAGC
``` a       S  Y  W  I  K  Q  G  S  G  N  T  T  V  T  R  G  N  E  T  S  -

```
       GTGAGTGACAGCATGAAGGACAATCCTCATATGCAGTACTATGCCAGCATCTACGCCCTC
  2701 --------+--------+--------+--------+--------+--------+   2760
       CACTCACTGTCGTACTTCCTGTTAGGAGTATACGTCATGATACGGTCGTAGATGCGGGAG
``` a       V  S  D  S  M  K  D  N  P  H  M  Q  Y  Y  A  S  I  Y  A  L  -

```
       TCCATGGCAGTCATGCTGATCCTGAAAGCCATTCGAGGAGTTGTCTTTGTCAAGGGCACG
  2761 --------+--------+--------+--------+--------+--------+   2820
       AGGTACCGTCAGTACGACTAGGACTTTCGGTAAGCTCCTCAACAGAAACAGTTCCCGTGC
``` a       S  M  A  V  M  L  I  L  K  A  I  R  G  V  V  F  V  K  G  T  -

```
       CTGCGAGCTTCCTCCCGGCTGCATGACGAGCTTTTCCGAAGGATCCTTCGAAGCCCTATG
  2821 --------+--------+--------+--------+--------+--------+   2880
       GACGCTCGAAGGAGGGCCGACGTACTGCTCGAAAAGGCTTCCTAGGAAGCTTCGGGATAC
``` a       L  R  A  S  S  R  L  H  D  E  L  F  R  R  I  L  R  S  P  M  -

```
       AAGTTTTTTGACACGACCCCCACAGGGAGGATTCTCAACAGGTTTTCCAAAGACATGGAT
  2881 --------+--------+--------+--------+--------+--------+   2940
       TTCAAAAAACTGTGCTGGGGGTGTCCCTCCTAAGAGTTGTCCAAAAGGTTTCTGTACCTA
``` a       K  F  F  D  T  T  P  T  G  R  I  L  N  R  F  S  K  D  M  D  -

```
       GAAGTTGACGTGCGGCTGCCGTTCCAGGCCGAGATGTTCATCCAGAACGTTATCCTGGTG
```

Figure 13G

```
2941 ---------+---------+---------+---------+---------+---------+   3000
     CTTCAACTGCACGCCGACGGCAAGGTCCGGCTCTACAAGTAGGTCTTGCAATAGGACCAC
``` a    E V D V R L P F Q A E M F I Q N V I L V -

```
     TTCTTCTGTGTGGGAATGATCGCAGGAGTCTTCCCGTGGTTCCTTGTGGCAGTGGGGCCC
3001 ---------+---------+---------+---------+---------+---------+   3060
     AAGAAGACACACCCTTACTAGCGTCCTCAGAAGGGCACCAAGGAACACCGTCACCCCGGG
``` a    F F C V G M I A G V F P W F L V A V G P -

```
     CTTGTCATCCTCTTTTCAGTCCTGCACATTGTCTCCAGGGTCCTGATTCGGGAGCTGAAG
3061 ---------+---------+---------+---------+---------+---------+   3120
     GAACAGTAGGAGAAAAGTCAGGACGTGTAACAGAGGTCCCAGGACTAAGCCCTCGACTTC
``` a    L V I L F S V L H I V S R V L I R E L K -

```
     CGTCTGGACAATATCACGCAGTCACCTTTCCTCTCCCACATCACGTCCAGCATACAGGGC
3121 ---------+---------+---------+---------+---------+---------+   3180
     GCAGACCTGTTATAGTGCGTCAGTGGAAAGGAGAGGGTGTAGTGCAGGTCGTATGTCCCG
``` a    R L D N I T Q S P F L S H I T S S I Q G -

```
     CTTGCCACCATCCACGCCTACAATAAAGGGCAGGAGTTTCTGCACAGATACCAGGAGCTG
3181 ---------+---------+---------+---------+---------+---------+   3240
     GAACGGTGGTAGGTGCGGATGTTATTTCCCGTCCTCAAAGACGTGTCTATGGTCCTCGAC
``` a    L A T I H A Y N K G Q E F L H R Y Q E L -

```
     CTGGATGACAACCAAGCTCCTTTTTTTTTTGTTTACGTGTGCGATGCGGTGGCTGGCTGTG
3241 ---------+---------+---------+---------+---------+---------+   3300
     GACCTACTGTTGGTTCGAGGAAAAAAAAACAAATGCACACGCTACGCCACCGACCGACAC
``` a    L D D N Q A P F F L F T C A M R W L A V -

```
     CGGCTGGACCTCATCAGCATCGCCCTCATCACCACCACGGGGCTGATGATCGTTCTTATG
3301 ---------+---------+---------+---------+---------+---------+   3360
     GCCGACCTGGAGTAGTCGTAGCGGGAGTAGTGGTGGTGCCCCGACTACTAGCAAGAATAC
``` a    R L D L I S I A L I T T T G L M I V L M -

```
     CACGGGCAGATTCCCCCAGCCTATGCGGGTCTCGCCATCTCTTATGCTGTCCAGTTAACG
3361 ---------+---------+---------+---------+---------+---------+   3420
```

Figure 13H

```
                  GTGCCCGTCTAAGGGGGTCGGATACGCCCAGAGCGGTAGAGAATACGACAGGTCAATTGC a        H  G  Q  I  P  P  A  Y  A  G  L  A  I  S  Y  A  V  Q  L  T   -

GGGCTGTTCCAGTTTACGGTCAGACTGGCATCTGAGACAGAAGCTCGATTCACCTCGGTG
    3421 ———+———+———+———+———+———+  3480
         CCCGACAAGGTCAAATGCCAGTCTGACCGTAGACTCTGTCTTCGAGCTAAGTGGAGCCAC a        G  L  F  Q  F  T  V  R  L  A  S  E  T  E  A  R  F  T  S  V   -

GAGAGGATCAATCACTACATTAAGACTCTGTCCTTGGAAGCACCTGCCAGAATTAAGAAC
    3481 ———+———+———+———+———+———+  3540
         CTCTCCTAGTTAGTGATGTAATTCTGAGACAGGAACCTTCGTGGACGGTCTTAATTCTTG a        E  R  I  N  H  Y  I  K  T  L  S  L  E  A  P  A  R  I  K  N   -

AAGGCTCCCTCCCCTGACTGGCCCCAGGAGGGAGAGGTGACCTTTGAGAACGCAGAGATG
    3541 ———+———+———+———+———+———+  3600
         TTCCGAGGGAGGGGACTGACCGGGGTCCTCCCTCTCCACTGGAAACTCTTGCGTCTCTAC a        K  A  P  S  P  D  W  P  Q  E  G  E  V  T  F  E  N  A  E  M   -

AGGTACCGAGAAAACCTCCCTCTTGTCCTAAAGAAAGTATCCTTCACGATCAAACCTAAA
    3601 ———+———+———+———+———+———+  3660
         TCCATGGCTCTTTTGGAGGGAGAACAGGATTTCTTTCATAGGAAGTGCTAGTTTGGATTT a        R  Y  R  E  N  L  P  L  V  L  K  K  V  S  F  T  I  K  P  K   -

GAGAAGATTGGCATTGTGGGGCGGACAGGATCAGGGAAGTCCTCGCTGGGGATGGCCCTC
    3661 ———+———+———+———+———+———+  3720
         CTCTTCTAACCGTAACACCCCGCCTGTCCTAGTCCCTTCAGGAGCGACCCCTACCGGGAG a        E  K  I  G  I  V  G  R  T  G  S  G  K  S  S  L  G  M  A  L   -

TTCCGTCTGGTGGAGTTATCTGGAGGCTGCATCAAGATTGATGGAGTGAGAATCAGTGAT
    3721 ———+———+———+———+———+———+  3780
         AAGGCAGACCACCTCAATAGACCTCCGACGTAGTTCTAACTACCTCACTCTTAGTCACTA a        F  R  L  V  E  L  S  G  G  C  I  K  I  D  G  V  R  I  S  D   -

ATTGGCCTTGCCGACCTCCGAAGCAAACTCTCTATCATTCCTCAAGAGCCGGTGCTGTTC
    3781 ———+———+———+———+———+———+  3840
         TAACCGGAACGGCTGGAGGCTTCGTTTGAGAGATAGTAAGGAGTTCTCGGCCACGACAAG
```

Figure 13I a   I G L A D L R S K L S I I P Q E P V L F -

```
     AGTGGCACTGTCAGATCAAATTTGGACCCCTTCAACCAGTACACTGAAGACCAGATTTGG
3841 --------+---------+---------+---------+---------+---------+   3900
     TCACCGTGACAGTCTAGTTTAAACCTGGGGAAGTTGGTCATGTGACTTCTGGTCTAAACC
``` a   S G T V R S N L D P F N Q Y T E D Q I W -

```
     GATGCCCTGGAGAGGACACACATGAAAGAATGTATTGCTCAGCTACCTCTGAAACTTGAA
3901 --------+---------+---------+---------+---------+---------+   3960
     CTACGGGACCTCTCCTGTGTGTACTTTCTTACATAACGAGTCGATGGAGACTTTGAACTT
``` a   D A L E R T H M K E C I A Q L P L K L E -

```
     TCTGAAGTGATGGAGAATGGGGATAACTTCTCAGTGGGGGAACGGCAGCTCTTGTGCATA
3961 --------+---------+---------+---------+---------+---------+   4020
     AGACTTCACTACCTCTTACCCCTATTGAAGAGTCACCCCCTTGCCGTCGAGAACACGTAT
``` a   S E V M E N G D N F S V G E R Q L L C I -

```
     GCTAGAGCCCTGCTCCGCCACTGTAAGATTCTGATTTTAGATGAAGCCACAGCTGCCATG
4021 --------+---------+---------+---------+---------+---------+   4080
     CGATCTCGGGACGAGGCGGTGACATTCTAAGACTAAAATCTACTTCGGTGTCGACGGTAC
``` a   A R A L L R H C K I L I L D E A T A A M -

```
     GACACAGAGACAGACTTATTGATTCAAGAGACCATCCGAGAAGCATTTGCAGACTGTACC
4081 --------+---------+---------+---------+---------+---------+   4140
     CTGTGTCTCTGTCTGAATAACTAAGTTCTCTGGTAGGCTCTTCGTAAACGTCTGACATGG
``` a   D T E T D L L I Q E T I R E A F A D C T -

```
     ATGCTGACCATTGCCCATCGCCTGCACACGGTTCTAGGCTCCGATAGGATTATGGTGCTG
4141 --------+---------+---------+---------+---------+---------+   4200
     TACGACTGGTAACGGGTAGCGGACGTGTGCCAAGATCCGAGGCTATCCTAATACCACGAC
``` a   M L T I A H R L H T V L G S D R I M V L -

```
     GCCCAGGGACAGGTGGTGGAGTTTGACACCCCATCGGTCCTTCTGTCCAACGACAGTTCC
4201 --------+---------+---------+---------+---------+---------+   4260
     CGGGTCCCTGTCCACCACCTCAAACTGTGGGGTAGCCAGGAAGACAGGTTGCTGTCAAGG
```

Figure 13J a   A Q G Q V V E F D T P S V L L S N D S S

```
    CGATTCTATGCCATGTTTGCTGCTGCAGAGAACAAGGTCGCTGTCAAGGGCTGA
4261 ------+--------+---------+---------+---------+----  4314
    GCTAAGATACGGTACAAACGACGACGTCTCTTGTTCCAGCGACAGTTCCCGACT
``` a   R F Y A M F A A A E N K V A V K G *

Figure 13K

MOAT D cDNA AND AMINO ACID SEQUENCE ENCODED THEREBY

```
    ATGGACGCCCTGTGCGGTTCCGGGGAGCTCGGCTCCAAGTTCTGGGACTCCAACCTGTCT
1 ──────+──────+──────+──────+──────+──────+  60
    TACCTGCGGGACACGCCAAGGCCCCTCGAGCCGAGGTTCAAGACCCTGAGGTTGGACAGA
``` a     M D A L C G S G E L G S K F W D S N L S -

```
     GTGCACACAGAAAACCCGGACCTCACTCCCTGCTTCCAGAACTCCCTGCTGGCCTGGGTG
61 ──────+──────+──────+──────+──────+──────+  120
     CACGTGTGTCTTTTGGGCCTGGAGTGAGGGACGAAGGTCTTGAGGGACGACCGGACCCAC
``` a     V H T E N P D L T P C F Q N S L L A W V -

```
      CCCTGCATCTACCTGTGGGTCGCCCTGCCCTGCTACTTGCTCTACCTGCGGCACCATTGT
121 ──────+──────+──────+──────+──────+──────+  180
      GGGACGTAGATGGACACCCAGCGGGACGGGACGATGAACGAGATGGACGCCGTGGTAACA
``` a     P C I Y L W V A L P C Y L L Y L R H H C -

```
      CGTGGCTACATCATCCTCTCCCACCTGTCCAAGCTCAAGATGGTCCTGGGTGTCCTGCTG
181 ──────+──────+──────+──────+──────+──────+  240
      GCACCGATGTAGTAGGAGAGGGTGGACAGGTTCGAGTTCTACCAGGACCCACAGGACGAC
``` a     R G Y I I L S H L S K L K M V L G V L L -

```
      TGGTGCGTCTCCTGGGCGGACCTTTTTTACTCCTTCCATGGCCTGGTCCATGGCCGGGCC
241 ──────+──────+──────+──────+──────+──────+  300
      ACCACGCAGAGGACCCGCCTGGAAAAAATGAGGAAGGTACCGGACCAGGTACCGGCCCGG
``` a     W C V S W A D L F Y S F H G L V H G R A -

```
      CCTGCCCCTGTTTTCTTTGTCACCCCCTTGGTGGTGGGGGTCACCATGCTGCTGGCCACC
301 ──────+──────+──────+──────+──────+──────+  360
      GGACGGGGACAAAAGAAACAGTGGGGGAACCACCACCCCCAGTGGTACGACGACCGGTGG
``` a     P A P V F F V T P L V V G V T M L L A T -

```
      CTGCTGATACAGTATGAGCGGCTGCAGGGCGTACAGTCTTCGGGGGTCCTCATTATCTTC
```

Figure 14A

```
           361 ---------+---------+---------+---------+---------+---------+ 420
              GACGACTATGTCATACTCGCCGACGTCCCGCATGTCAGAAGCCCCCAGGAGTAATAGAAG a     L L I Q Y E R L Q G V Q S S G V L I I F  -

TGGTTCCTGTGTGTGGTCTGCGCCATCGTCCCATTCCGCTCCAAGATCCTTTTAGCCAAG
           421 ---------+---------+---------+---------+---------+---------+ 480
              ACCAAGGACACACACCAGACGCGGTAGCAGGGTAAGGCGAGGTTCTAGGAAAATCGGTTC a     W F L C V V C A I V P F R S K I L L A K  -

GCAGAGGGTGAGATCTCAGACCCCTTCCGCTTCACCACCTTCTACATCCACTTTGCCCTG
           481 ---------+---------+---------+---------+---------+---------+ 540
              CGTCTCCCACTCTAGAGTCTGGGGAAGGCGAAGTGGTGGAAGATGTAGGTGAAACGGGAC a     A E G E I S D P F R F T T F Y I H F A L  -

GTACTCTCTGCCCTCATCTTGGCCTGCTTCAGGGAGAAACCTCCATTTTTCTCCGCAAAG
           541 ---------+---------+---------+---------+---------+---------+ 600
              CATGAGAGACGGGAGTAGAACCGGACGAAGTCCCTCTTTGGAGGTAAAAAGAGGCGTTTC a     V L S A L I L A C F R E K P P F F S A K  -

AATGTCGACCCTAACCCCTACCCTGAGACCAGCGCTGGCTTTCTCTCCCGCCTGTTTTTC
           601 ---------+---------+---------+---------+---------+---------+ 660
              TTACAGCTGGGATTGGGGATGGGACTCTGGTCGCGACCGAAAGAGAGGGCGGACAAAAAG a     N V D P N P Y P E T S A G F L S R L F F  -

TGGTGGTTCACAAAGATGGCCATCTATGGCTACCGGCATCCCCTGGAGGAGAAGGACCTC
           661 ---------+---------+---------+---------+---------+---------+ 720
              ACCACCAAGTGTTTCTACCGGTAGATACCGATGGCCGTAGGGGACCTCCTCTTCCTGGAG a     W W F T K M A I Y G Y R H P L E E K D L  -

TGGTCCCTAAAGGAAGAGGACAGATCCCAGATGGTGGTGCAGCAGCTGCTGGAGGCATGG
           721 ---------+---------+---------+---------+---------+---------+ 780
              ACCAGGGATTTCCTTCTCCTGTCTAGGGTCTACCACCACGTCGTCGACGACCTCCGTACC a     W S L K E E D R S Q M V V Q Q L L E A W  -

AGGAAGCAGGAAAAGCAGACGGCACGACACAAGGCTTCAGCAGCACCTGGGAAAAATGCC
           781 ---------+---------+---------+---------+---------+---------+ 840
```

Figure 14B

TCCTTCGTCCTTTTCGTCTGCCGTGCTGTGTTCCGAAGTCGTCGTGGACCCTTTTTACGG a    R  K  Q  E  K  Q  T  A  R  H  K  A  S  A  A  P  G  K  N  A  -

```
      TCCGGCGAGGACGAGGTGCTGCTGGGTGCCCGGCCCAGGCCCCGGAAGCCCTCCTTCCTG
841 ------+--------+--------+---------+---------+--------+   900
      AGGCCGCTCCTGCTCCACGACGACCCACGGGCCGGGTCCGGGGCCTTCGGGAGGAAGGAC
``` a    S  G  E  D  E  V  L  L  G  A  R  P  R  P  R  K  P  S  F  L  -

```
      AAGGCCCTGCTGGCCACCTTCGGCTCCAGCTTCCTCATCAGTGCCTGCTTCAAGCTTATC
901 ------+--------+-------+---------+--------+--------+    960
      TTCCGGGACGACCGGTGGAAGCCGAGGTCGAAGGAGTAGTCACGGACGAAGTTCGAATAG
``` a    K  A  L  L  A  T  F  G  S  S  F  L  I  S  A  C  F  K  L  I  -

```
      CAGGACCTGCTCTCCTTCATCAATCCACAGCTGCTCAGCATCCTGATCAGGTTTATCTCC
961 ------+--------+-------+---------+--------+--------+   1020
      GTCCTGGACGAGAGGAAGTAGTTAGGTGTCGACGAGTCGTAGGACTAGTCCAAATAGAGG
``` a    Q  D  L  L  S  F  I  N  P  Q  L  L  S  I  L  I  R  F  I  S  -

```
       AACCCCATGGCCCCCTCCTGGTGGGGCTTCCTGGTGGCTGGGCTGATGTTCCTGTGCTCC
1021 -----+-------+-------+--------+--------+---------+    1080
       TTGGGGTACCGGGGGAGGACCACCCCGAAGGACCACCGACCCGACTACAAGGACACGAGG
``` a    N  P  M  A  P  S  W  W  G  F  L  V  A  G  L  M  F  L  C  S  -

```
       ATGATGCAGTCGCTGATCTTACAACACTATTACCACTACATCTTTGTGACTGGGGTGAAG
1081 -----+--------+-------+---------+--------+--------+    1140
       TACTACGTCAGCGACTAGAATGTTGTGATAATGGTGATGTAGAAACACTGACCCCACTTC
``` a    M  M  Q  S  L  I  L  Q  H  Y  Y  H  Y  I  F  V  T  G  V  K  -

```
       TTTCGTACTGGGATCATGGGTGTCATCTACAGGAAGGCTCTGGTTATCACCAACTCAGTC
1141 -----+--------+--------+--------+---------+---------+  1200
       AAAGCATGACCCTAGTACCCACAGTAGATGTCCTTCCGAGACCAATAGTGGTTGAGTCAG
``` a    F  R  T  G  I  M  G  V  I  Y  R  K  A  L  V  I  T  N  S  V  -

```
       AAACGTGCGTCCACTGTGGGGGAAATTGTCAACCTCATGTCAGTGGATGCCCAGCGCTTC
1201 -----+--------+--------+--------+--------+---------+   1260
       TTTGCACGCAGGTGACACCCCCTTTAACAGTTGGAGTACAGTCACCTACGGGTCGCGAAG
```

Figure 14C a  K R A S T V G E I V N L M S V D A Q R F -

```
         ATGGACCTTGCCCCCTTCCTCAATCTGCTGTGGTCAGCACCCCTGCAGATCATCCTGGCG
1261 --------+---------+---------+---------+---------+---------+   1320
         TACCTGGAACGGGGGAAGGAGTTAGACGACACCAGTCGTGGGGACGTCTAGTAGGACCGC
``` a  M D L A P F L N L L W S A P L Q I I L A -

```
         ATCTACTTCCTCTGGCAGAACCTAGGTCCCTCTGTCCTGGCTGGAGTCGCTTTCATGGTC
1321 --------+---------+---------+---------+---------+---------+   1380
         TAGATGAAGGAGACCGTCTTGGATCCAGGGAGACAGGACCGACCTCAGCGAAAGTACCAG
``` a  I Y F L W Q N L G P S V L A G V A F M V -

```
         TTGCTGATTCCACTCAACGGAGCTGTGGCCGTGAAGATGCGCGCCTTCCAGGTAAAGCAA
1381 --------+---------+---------+---------+---------+---------+   1440
         AACGACTAAGGTGAGTTGCCTCGACACCGGCACTTCTACGCGCGGAAGGTCCATTTCGTT
``` a  L L I P L N G A V A V K M R A F Q V K Q -

```
         ATGAAATTGAAGGACTCGCGCATCAAGCTGATGAGTGAGATCCTGAACGGCATCAAGGTG
1441 --------+---------+---------+---------+---------+---------+   1500
         TACTTTAACTTCCTGAGCGCGTAGTTCGACTACTCACTCTAGGACTTGCCGTAGTTCCAC
``` a  M K L K D S R I K L M S E I L N G I K V -

```
         CTGAAGCTGTACGCCTGGGAGCCCAGCTTCCTGAAGCAGGTGGAGGGCATCCGGCAGGGT
1501 --------+---------+---------+---------+---------+---------+   1560
         GACTTCGACATGCGGACCCTCGGGTCGAAGGACTTCGTCCACCTCCCGTAGGCCGTCCCA
``` a  L K L Y A W E P S F L K Q V E G I R Q G -

```
         GAGCTCCAGCTGCTGCGCACGGCGGCCTACCTCCACACCACAACCACCTTCACCTGGATG
1561 --------+---------+---------+---------+---------+---------+   1620
         CTCGAGGTCGACGACGCGTGCCGCCGGATGGAGGTGTGGTGTTGGTGGAAGTGGACCTAC
``` a  E L Q L L R T A A Y L H T T T T F T W M -

```
         TGCAGCCCCTTCCTGGTGACCCTGATCACCCTCTGGGTGTACGTGTACGTGGACCCAAAC
1621 --------+---------+---------+---------+---------+---------+   1680
         ACGTCGGGGAAGGACCACTGGGACTAGTGGGAGACCCACATGCACATGCACCTGGGTTTG
```

AATGTGCTGGACGCCGAGAAGGCCTTTGTGTCTGTGTCCTTGTTTAATATCTTAAGACTT
1681 ------+------+------+------+------+------+ 1740
     TTACACGACCTGCGGCTCTTCCGGAAACACAGACACAGGAACAAATTATAGAATTCTGAA a    N V L D A E K A F V S V S L F N I L R L  -

CCCCTCAACATGCTGCCCCAGTTAATCAGCAACCTGACTCAGGCCAGTGTGTCTCTGAAA
1741 ------+------+------+------+------+------+ 1800
     GGGGAGTTGTACGACGGGGTCAATTAGTCGTTGGACTGAGTCCGGTCACACAGAGACTTT a    P L N M L P Q L I S N L T Q A S V S L K  -

CGGATCCAGCAATTCCTGAGCCAAGAGGAACTTGACCCCCAGAGTGTGGAAAGAAAGACC
1801 ------+------+------+------+------+------+ 1860
     GCCTAGGTCGTTAAGGACTCGGTTCTCCTTGAACTGGGGGTCTCACACCTTTCTTTCTGG a    R I Q Q F L S Q E E L D P Q S V E R K T  -

ATCTCCCCAGGCTATGCCATCACCATACACAGTGGCACCTTCACCTGGGCCCAGGACCTG
1861 ------+------+------+------+------+------+ 1920
     TAGAGGGGTCCGATACGGTAGTGGTATGTGTCACCGTGGAAGTGGACCCGGGTCCTGGAC a    I S P G Y A I T I H S G T F T W A Q D L  -

CCCCCCACTCTGCACAGCCTAGACATCCAGGTCCCGAAAGGGGCACTGGTGGCCGTGGTG
1921 ------+------+------+------+------+------+ 1980
     GGGGGGTGAGACGTGTCGGATCTGTAGGTCCAGGGCTTTCCCCGTGACCACCGGCACCAC a    P P T L H S L D I Q V P K G A L V A V V  -

GGGCCTGTGGGCTGTGGGAAGTCCTCCCTGGTGTCTGCCCTGCTGGGAGAGATGGAGAAG
1981 ------+------+------+------+------+------+ 2040
     CCCGGACACCCGACACCCTTCAGGAGGGACCACAGACGGGACGACCCTCTCTACCTCTTC a    G P V G C G K S S L V S A L L G E M E K  -

CTAGAAGGCAAAGTGCACATGAAGGCATGGATCCAGAACTGCACTCTTCAGGAAAACGTG
2041 ------+------+------+------+------+------+ 2100
     GATCTTCCGTTTCACGTGTACTTCCGTACCTAGGTCTTGACGTGAGAAGTCCTTTTGCAC a    L E G K V H M K A W I Q N C T L Q E N V  -
```

Figure 14E

```
        CTTTTCGGCAAAGCCCTGAACCCCAAGCGCTACCAGCAGACTCTGGAGGCCTGTGCCTTG
   2101 ---------+---------+---------+---------+---------+---------+ 2160
        GAAAAGCCGTTTCGGGACTTGGGGTTCGCGATGGTCGTCTGAGACCTCCGGACACGGAAC a       L F G K A L N P K R Y Q Q T L E A C A L  -

CTAGCTGACCTGGAGATGCTGCCTGGTGGGGATCAGACAGAGATTGGAGAGAAGGGCATT
   2161 ---------+---------+---------+---------+---------+---------+ 2220
        GATCGACTGGACCTCTACGACGGACCACCCCTAGTCTGTCTCTAACCTCTCTTCCCGTAA a       L A D L E M L P G G D Q T E I G E K G I  -

AACCTGTCTGGGGGCCAGCGGCAGCGGGTCAGTCTGGCTCGAGCTGTTTACAGTGATGCC
   2221 ---------+---------+---------+---------+---------+---------+ 2280
        TTGGACAGACCCCCGGTCGCCGTCGCCCAGTCAGACCGAGCTCGACAAATGTCACTACGG a       N L S G G Q R Q R V S L A R A V Y S D A  -

GATATTTTCTTGCTGGATGACCCACTGTCCGCGGTGGACTCTCATGTGGCCAAGCACATC
   2281 ---------+---------+---------+---------+---------+---------+ 2340
        CTATAAAAGAACGACCTACTGGGTGACAGGCGCCACCTGAGAGTACACCGGTTCGTGTAG a       D I F L L D D P L S A V D S H V A K H I  -

TTTGACCACGTCATCGGGCCAGAAGGCGTGCTGGCAGGCAAGACGCGAGTGCTGGTGACG
   2341 ---------+---------+---------+---------+---------+---------+ 2400
        AAACTGGTGCAGTAGCCCGGTCTTCCGCACGACCGTCCGTTCTGCGCTCACGACCACTGC a       F D H V I G P E G V L A G K T R V L V T  -

CACGGCATTAGCTTCCTGCCCCAGACAGACTTCATCATTGTGCTAGCTGATGGACAGGTG
   2401 ---------+---------+---------+---------+---------+---------+ 2460
        GTGCCGTAATCGAAGGACGGGGTCTGTCTGAAGTAGTAACACGATCGACTACCTGTCCAC a       H G I S F L P Q T D F I I V L A D G Q V  -

TCTGAGATGGGCCCGTACCCAGCCCTGCTGCAGCGCAACGGCTCCTTTGCCAACTTTCTC
   2461 ---------+---------+---------+---------+---------+---------+ 2520
        AGACTCTACCCGGGCATGGGTCGGGACGACGTCGCGTTGCCGAGGAAACGGTTGAAAGAG a       S E M G P Y P A L L Q R N G S F A N F L  -
```

Figure 14F

```
        TGCAACTATGCCCCCGATGAGGACCAAGGGCACCTGGAGGACAGCTGGACCGCGTTGGAA
   2521 ---------+---------+---------+---------+---------+---------+  2580
        ACGTTGATACGGGGGCTACTCCTGGTTCCCGTGGACCTCCTGTCGACCTGGCGCAACCTT a       C N Y A P D E D Q G H L E D S W T A L E -

GGTGCAGAGGATAAGGAGGCACTGCTGATTGAAGACACACTCAGCAACCACACGGATCTG
   2581 ---------+---------+---------+---------+---------+---------+  2640
        CCACGTCTCCTATTCCTCCGTGACGACTAACTTCTGTGTGAGTCGTTGGTGTGCCTAGAC a       G A E D K E A L L I E D T L S N H T D L -

ACAGACAATGATCCAGTCACCTATGTGGTCCAGAAGCAGTTTATGAGACAGCTGAGTGCC
   2641 ---------+---------+---------+---------+---------+---------+  2700
        TGTCTGTTACTAGGTCAGTGGATACACCAGGTCTTCGTCAAATACTCTGTCGACTCACGG a       T D N D P V T Y V V Q K Q F M R Q L S A -

CTGTCCTCAGATGGGGAGGGACAGGGTCGGCCTGTACCCCGGAGGCACCTGGGTCCATCA
   2701 ---------+---------+---------+---------+---------+---------+  2760
        GACAGGAGTCTACCCCTCCCTGTCCCAGCCGGACATGGGGCCTCCGTGGACCCAGGTAGT a       L S S D G E G Q G R P V P R R H L G P S -

GAGAAGGTGCAGGTGACAGAGGCGAAGGCAGATGGGGCACTGACCCAGGAGGAGAAAGCA
   2761 ---------+---------+---------+---------+---------+---------+  2820
        CTCTTCCACGTCCACTGTCTCCGCTTCCGTCTACCCCGTGACTGGGTCCTCCTCTTTCGT a       E K V Q V T E A K A D G A L T Q E E K A -

GCCATTGGCACTGTGGAGCTCAGTGTGTTCTGGGATTATGCCAAGGCCGTGGGGCTCTGT
   2821 ---------+---------+---------+---------+---------+---------+  2880
        CGGTAACCGTGACACCTCGAGTCACACAAGACCCTAATACGGTTCCGGCACCCCGAGACA a       A I G T V E L S V F W D Y A K A V G L C -

ACCACGCTGGCCATCTGTCTCCTGTATGTGGGTCAAAGTGCGGCTGCCATTGGAGCCAAT
   2881 ---------+---------+---------+---------+---------+---------+  2940
        TGGTGCGACCGGTAGACAGAGGACATACACCCAGTTTCACGCCGACGGTAACCTCGGTTA a       T T L A I C L L Y V G Q S A A A I G A N -

GTGTGGCTCAGTGCCTGGACAAATGATGCCATGGCAGACAGTAGACAGAACAACACTTCC
```

Figure 14G

```
                                                                    3000
2941 ————+————+————+————+————+————+
     CACACCGAGTCACGGACCTGTTTACTACGGTACCGTCTGTCATCTGTCTTGTTGTGAAGG a    V  W  L  S  A  W  T  N  D  A  M  A  D  S  R  Q  N  N  T  S  -

CTGAGGCTGGGCGTCTATGCTGCTTTAGGAATTCTGCAAGGGTTCTTGGTGATGCTGGCA
3001 ————+————+————+————+————+————+    3060
     GACTCCGACCCGCAGATACGACGAAATCCTTAAGACGTTCCCAAGAACCACTACGACCGT a    L  R  L  G  V  Y  A  A  L  G  I  L  Q  G  F  L  V  M  L  A  -

GCCATGGCCATGGCAGCGGGTGGCATCCAGGCTGCCCGTGTGTTGCACCAGGCACTGCTG
3061 ————+————+————+————+————+————+    3120
     CGGTACCGGTACCGTCGCCCACCGTAGGTCCGACGGGCACACAACGTGGTCCGTGACGAC a    A  M  A  M  A  A  G  G  I  Q  A  A  R  V  L  H  Q  A  L  L  -

CACAACAAGATACGCTCGCCACAGTCCTTCTTTGACACCACACCATCAGGCCGCATCCTG
3121 ————+————+————+————+————+————+    3180
     GTGTTGTTCTATGCGAGCGGTGTCAGGAAGAAACTGTGGTGTGGTAGTCCGGCGTAGGAC a    H  N  K  I  R  S  P  Q  S  F  F  D  T  T  P  S  G  R  I  L  -

AACTGCTTCTCCAAGGACATCTATGTCGTTGATGAGGTTCTGGCCCCTGTCATCCTCATG
3181 ————+————+————+————+————+————+    3240
     TTGACGAAGAGGTTCCTGTAGATACAGCAACTACTCCAAGACCGGGGACAGTAGGAGTAC a    N  C  F  S  K  D  I  Y  V  V  D  E  V  L  A  P  V  I  L  M  -

CTGCTCAATTCCTTCTTCAACGCCATCTCCACTCTTGTGGTCATCATGGCCAGCACGCCG
3241 ————+————+————+————+————+————+    3300
     GACGAGTTAAGGAAGAAGTTGCGGTAGAGGTGAGAACACCAGTAGTACCGGTCGTGCGGC a    L  L  N  S  F  F  N  A  I  S  T  L  V  V  I  M  A  S  T  P  -

CTCTTCACTGTGGTCATCCTGCCCCTGGCTGTGCTCTACACCTTAGTGCAGCGCTTCTAT
3301 ————+————+————+————+————+————+    3360
     GAGAAGTGACACCAGTAGGACGGGGACCGACACGAGATGTGGAATCACGTCGCGAAGATA a    L  F  T  V  V  I  L  P  L  A  V  L  Y  T  L  V  Q  R  F  Y  -

GCAGCCACATCACGGCAACTGAAGCGGCTGGAATCAGTCAGCCGCTCACCTATCTACTCC
3361 ————+————+————+————+————+————+    3420
```

Figure 14H

```
          CGTCGGTGTAGTGCCGTTGACTTCGCCGACCTTAGTCAGTCGGCGAGTGGATAGATGAGG a         A A T S R Q L K R L E S V S R S P I Y S -

CACTTTTCGGAGACAGTGACTGGTGCCAGTGTCATCCGGGCCTACAACCGCAGCCGGGAT
     3421 --------+---------+---------+---------+---------+---------+  3480
          GTGAAAAGCCTCTGTCACTGACCACGGTCACAGTAGGCCCGGATGTTGGCGTCGGCCCTA a         H F S E T V T G A S V I R A Y N R S R D -

TTTGAGATCATCAGTGATACTAAGGTGGATGCCAACCAGAGAAGCTGCTACCCCTACATC
     3481 --------+---------+---------+---------+---------+---------+  3540
          AAACTCTAGTAGTCACTATGATTCCACCTACGGTTGGTCTCTTCGACGATGGGGATGTAG a         F E I I S D T K V D A N Q R S C Y P Y I -

ATCTCCAACCGGTGGCTGAGCATCGGAGTGGAGTTCGTGGGGAACTGCGTGGTGCTCTTT
     3541 --------+---------+---------+---------+---------+---------+  3600
          TAGAGGTTGGCCACCGACTCGTAGCCTCACCTCAAGCACCCCTTGACGCACCACGAGAAA a         I S N R W L S I G V E F V G N C V V L F -

GCTGCACTATTTGCCGTCATCGGGAGGAGCAGCCTGAACCCGGGGCTGGTGGGCCTTTCT
     3601 --------+---------+---------+---------+---------+---------+  3660
          CGACGTGATAAACGGCAGTAGCCCTCCTCGTCGGACTTGGGCCCCGACCACCCGGAAAGA a         A A L F A V I G R S S L N P G L V G L S -

GTGTCCTACTCCTTGCAGGTGACATTTGCTCTGAACTGGATGATACGAATGATGTCAGAT
     3661 --------+---------+---------+---------+---------+---------+  3720
          CACAGGATGAGGAACGTCCACTGTAAACGAGACTTGACCTACTATGCTTACTACAGTCTA a         V S Y S L Q V T F A L N W M I R M M S D -

TTGGAATCTAACATCGTGGCTGTGGAGAGGGTCAAGGAGTACTCCAAGACAGAGACAGAG
     3721 --------+---------+---------+---------+---------+---------+  3780
          AACCTTAGATTGTAGCACCGACACCTCTCCCAGTTCCTCATGAGGTTCTGTCTCTGTCTC a         L E S N I V A V E R V K E Y S K T E T E -

GCGCCCTGGGTGGTGGAAGGCAGCCGCCCTCCCGAAGGTTGGCCCCCACGTGGGGAGGTG
     3781 --------+---------+---------+---------+---------+---------+  3840
          CGCGGGACCCACCACCTTCCGTCGGCGGGAGGGCTTCCAACCGGGGGTGCACCCCTCCAC
```

Figure 14I a   A P W V V E G S R P P E G W P P R G E V -

```
     GAGTTCCGGAATTATTCTGTGCGCTACCGGCCGGGCCTAGACCTGGTGCTGAGAGACCTG
3841 ------+--------+--------+--------+--------+--------+  3900
     CTCAAGGCCTTAATAAGACACGCGATGGCCGGCCCGGATCTGGACCACGACTCTCTGGAC
``` a   E F R N Y S V R Y R P G L D L V L R D L -

```
     AGTCTGCATGTGCACGGTGGCGAGAAGGTGGGGATCGTGGGCCGCACTGGGGCTGGCAAG
3901 ------+--------+--------+--------+--------+--------+  3960
     TCAGACGTACACGTGCCACCGCTCTTCCACCCCTAGCACCCGGCGTGACCCCGACCGTTC
``` a   S L H V H G G E K V G I V G R T G A G K -

```
     TCTTCCATGACCCTTTGCCTGTTCCGCATCCTGGAGGCGGCAAAGGGTGAAATCCGCATT
3961 ------+--------+--------+--------+--------+--------+  4020
     AGAAGGTACTGGGAAACGGACAAGGCGTAGGACCTCCGCCGTTTCCCACTTTAGGCGTAA
``` a   S S M T L C L F R I L E A A K G E I R I -

```
     GATGGCCTCAATGTGGCAGACATCGGCCTCCATGACCTGCGCTCTCAGCTGACCATCATC
4021 ------+--------+--------+--------+--------+--------+  4080
     CTACCGGAGTTACACCGTCTGTAGCCGGAGGTACTGGACGCGAGAGTCGACTGGTAGTAG
``` a   D G L N V A D I G L H D L R S Q L T I I -

```
     CCGCAGGACCCCATCCTGTTCTCGGGGACCCTGCGCATGAACCTGGACCCCTTCGGCAGC
4081 ------+--------+--------+--------+--------+--------+  4140
     GGCGTCCTGGGGTAGGACAAGAGCCCCTGGGACGCGTACTTGGACCTGGGGAAGCCGTCG
``` a   P Q D P I L F S G T L R M N L D P F G S -

```
     TACTCAGAGGAGGACATTTGGTGGGCTTTGGAGCTGTCCCACCTGCACACGTTTGTGAGC
4141 ------+--------+--------+--------+--------+--------+  4200
     ATGAGTCTCCTCCTGTAAACCACCCGAAACCTCGACAGGGTGGACGTGTGCAAACACTCG
``` a   Y S E E D I W W A L E L S H L H T F V S -

```
     TCCCAGCCGGCAGGCCTGGACTTCCAGTGCTCAGAGGGCGGGGAGAATCTCAGCGTGGGC
4201 ------+--------+--------+--------+--------+--------+  4260
     AGGGTCGGCCGTCCGGACCTGAAGGTCACGAGTCTCCCGCCCCTCTTAGAGTCGCACCCG
```

CAGAGGCAGCTCGTGTGCCTGGCCCGAGCCCTGCTCCGCAAGAGCCGCATCCTGGTTTTA
4261 --------+--------+--------+--------+--------+--------+  4320
     GTCTCCGTCGAGCACACGGACCGGGCTCGGGACGAGGCGTTCTCGGCGTAGGACCAAAAT a    Q R Q L V C L A R A L L R K S R I L V L  -

GACGAGGCCACACCTGCCATCGACCTGGAGACTGACAACCTCATCCAGGCTACCATCCGC
4321 --------+--------+--------+--------+--------+--------+  4380
     CTGCTCCGGTGTCGACGGTAGCTGGACCTCTGACTGTTGGAGTAGGTCCGATGGTAGGCG a    D E A T A A I D L E T D N L I Q A T I R  -

ACCCAGTTTGATACCTGCACTGTCCTGACCATCGCACACCGGCTTAACACTATCATGGAC
4381 --------+--------+--------+--------+--------+--------+  4440
     TGGGTCAAACTATGGACGTGACAGGACTGGTAGCGTGTGGCCGAATTGTGATAGTACCTG a    T Q F D T C T V L T I A H R L N T I M D  -

TACACCAGGGTCCTGGTCCTGGACAAAGGAGTAGTAGCTGAATTTGATTCTCCAGCCAAC
4441 --------+--------+--------+--------+--------+--------+  4500
     ATGTGGTCCCAGGACCAGGACCTGTTTCCTCATCATCGACTTAAACTAAGAGGTCGGTTG a    Y T R V L V L D K G V V A E F D S P A N  -

CTCATTGCAGCTAGAGGCATCTTCTACGGGATGGCCAGAGATGCTGGACTTGCCTAA
4501 --------+--------+--------+--------+-------+  4557
     GAGTAACGTCGATCTCCGTAGAAGATGCCCTACCGGTCTCTACGACCTGAACGGATT a    L I A A R G I F Y G M A R D A G L A *  -
```

Figure 14K

MOAT E cDNA AND AMINO ACID SEQUENCE ENCODED THEREBY

```
    ATGGCCGCGCCTGCTGAGCCCTGCGCGGGGCAGGGGGTCTGGAACCAGACAGAGCCTGAA
1   ------+------+------+------+------+------+  60
    TACCGGCGCGGACGACTCGGGACGCGCCCCGTCCCCCAGACCTTGGTCTGTCTCGGACTT a   M  A  A  P  A  E  P  C  A  G  Q  G  V  W  N  Q  T  E  P  E  -

CCTGCCGCCACCAGCCTGCTGAGCCTGTGCTTCCTGAGAACAGCAGGGGTCTGGGTACCC
61  ------+------+------+------+------+------+  120
    GGACGGCGGTGGTCGGACGACTCGGACACGAAGGACTCTTGTCGTCCCCAGACCCATGGG a   P  A  A  T  S  L  L  S  L  C  F  L  R  T  A  G  V  W  V  P  -

CCCATGTACCTCTGGGTCCTTGGTCCCATCTACCTCCTCTTCATCCACCACCATGGCCGG
121 ------+------+------+------+------+------+  180
    GGGTACATGGAGACCCAGGAACCAGGGTAGATGGAGGAGAAGTAGGTGGTGGTACCGGCC a   P  M  Y  L  W  V  L  G  P  I  Y  L  L  F  I  H  H  H  G  R  -

GGCTACCTCCGGATGTCCCCACTCTTCAAAGCCAAGATGGTGCTTGGATTCGCCCTCATA
181 ------+------+------+------+------+------+  240
    CCGATGGAGGCCTACAGGGGTGAGAAGTTTCGGTTCTACCACGAACCTAAGCGGGAGTAT a   G  Y  L  R  M  S  P  L  F  K  A  K  M  V  L  G  F  A  L  I  -

GTCCTGTGTACCTCCAGCGTGGCTGTCGCTCTTTGGAAAATCCAACAGGGAACGCCTGAG
241 ------+------+------+------+------+------+  300
    CAGGACACATGGAGGTCGCACCGACAGCGAGAAACCTTTTAGGTTGTCCCTTGCGGACTC a   V  L  C  T  S  S  V  A  V  A  L  W  K  I  Q  Q  G  T  P  E  -

GCCCCAGAATTCCTCATTCATCCTACTGTGTGGCTCACCACGATGAGCTTCGCAGTGTTC
301 ------+------+------+------+------+------+  360
    CGGGGTCTTAAGGAGTAAGTAGGATGACACACCGAGTGGTGCTACTCGAAGCGTCACAAG a   A  P  E  F  L  I  H  P  T  V  W  L  T  T  M  S  F  A  V  F  -

CTGATTCACACCGAGAGGAAAAAGGGAGTCCAGTCATCTGGAGTGCTGTTTGGTTACTGG
361 ------+------+------+------+------+------+  420
    GACTAAGTGTGGCTCTCCTTTTTCCCTCAGGTCAGTAGACCTCACGACAAACCAATGACC
```

Figure 15A a    L I H T E R K K G V Q S S G V L F G Y W -

```
    CTTCTCTGCTTTGTCTTGCCAGCTACCAACGCTGCCCAGCAGGCCTCCGGAGCGGGCTTC
421 ------+---------+---------+---------+---------+---------+  480
    GAAGAGACGAAACAGAACGGTCGATGGTTGCGACGGGTCGTCCGGAGGCCTCGCCCGAAG
``` a    L L C F V L P A T N A A Q Q A S G A G F -

```
    CAGAGCGACCCTGTCCGCCACCTGTCCACCTACCTATGCCTGTCTCTGGTGGTGGCACAG
481 ------+---------+---------+---------+---------+---------+  540
    GTCTCGCTGGGACAGGCGGTGGACAGGTGGATGGATACGGACAGAGACCACCACCGTGTC
``` a    Q S D P V R H L S T Y L C L S L V V A Q -

```
    TTTGTGCTGTCCTGCCTGGCGGATCAACCCCCCTTCTTCCCTGAAGACCCCCAGCAGTCT
541 ------+---------+---------+---------+---------+---------+  600
    AAACACGACAGGACGGACCGCCTAGTTGGGGGGAAGAAGGGACTTCTGGGGGTCGTCAGA
``` a    F V L S C L A D Q P P F F P E D P Q Q S -

```
    AACCCCTGTCCAGAGACTGGGGCAGCCTTCCCCTCCAAAGCCACGTTCTGGTGGGTTTCT
601 ------+---------+---------+---------+---------+---------+  660
    TTGGGGACAGGTCTCTGACCCCGTCGGAAGGGGAGGTTTCGGTGCAAGACCACCCAAAGA
``` a    N P C P E T G A A F P S K A T F W W V S -

```
    GGCCTGGTCTGGAGGGGATACAGGAGGCCACTGAGACCAAAAGACCTCTGGTCGCTTGGG
661 ------+---------+---------+---------+---------+---------+  720
    CCGGACCAGACCTCCCCTATGTCCTCCGGTGACTCTGGTTTTCTGGAGACCAGCGAACCC
``` a    G L V W R G Y R R P L R P K D L W S L G -

```
    AGAGAAAACTCCTCAGAAGAACTTGTTTCCCGGCTTGAAAAGGAGTGGATGAGGAACCGC
721 ------+---------+---------+---------+---------+---------+  780
    TCTCTTTTGAGGAGTCTTCTTGAACAAAGGGCCGAACTTTTCCTCACCTACTCCTTGGCG
``` a    R E N S S E E L V S R L E K E W M R N R -

```
    AGTGCAGCCCGGAGGCACAACAAGGCAATAGCATTTAAAAGGAAAGGCGGCAGTGGCATG
781 ------+---------+---------+---------+---------+---------+  840
    TCACGTCGGGCCTCCGTGTTGTTCCGTTATCGTAAATTTTCCTTTCCGCCGTCACCGTAC
```

Figure 15B a   S A A R R H N K A I A F K R K G G S G M -

```
      AAGGCTCCAGAGACCGAGCCCTTCCTACGGCAAGAAGGGAGCCAGTGGCGCCCACTGCTG
841 ──────+──────+──────+──────+──────+──────+  900
      TTCCGAGGTCTCTGGCTCGGGAAGGATGCCGTTCTTCCCTCGGTCACCGCGGGTGACGAC
``` a   K A P E T E P F L R Q E G S Q W R P L L -

```
      AAGGCCATCTGGCAGGTGTTCCATTCTACCTTCCTCCTGGGGACCCTCAGCCTCATCATC
901 ──────+──────+──────+──────+──────+──────+  960
      TTCCGGTAGACCGTCCACAAGGTAAGATGGAAGGAGGACCCCTGGGAGTCGGAGTAGTAG
``` a   K A I W Q V F H S T F L L G T L S L I I -

```
      AGTGATGTCTTCAGGTTCACTGTCCCCAAGCTGCTCAGCCTTTTCCTGGAGTTTATTGGT
961 ──────+──────+──────+──────+──────+──────+  1020
      TCACTACAGAAGTCCAAGTGACAGGGGTTCGACGAGTCGGAAAAGGACCTCAAATAACCA
``` a   S D V F R F T V P K L L S L F L E F I G -

```
       GATCCCAAGCCTCCAGCCTGGAAGGGCTACCTCCTCGCCGTGCTGATGTTCCTCTCAGCC
1021 ──────+──────+──────+──────+──────+──────+  1080
       CTAGGGTTCGGAGGTCGGACCTTCCCGATGGAGGAGCGGCACGACTACAAGGAGAGTCGG
``` a   D P K P P A W K G Y L L A V L M F L S A -

```
       TGCCTGCAAACGCTGTTTGAGCAGCAGAACATGTACAGGCTCAAGGTGCCGCAGATGAGG
1081 ──────+──────+──────+──────+──────+──────+  1140
       ACGGACGTTTGCGACAAACTCGTCGTCTTGTACATGTCCGAGTTCCACGGCGTCTACTCC
``` a   C L Q T L F E Q Q N M Y R L K V P Q M R -

```
       TTGCGGTCGGCCATCACTGGCCTGGTGTACAGAAAGGTCCTGGCTCTGTCCAGCGGCTCC
1141 ──────+──────+──────+──────+──────+──────+  1200
       AACGCCAGCCGGTAGTGACCGGACCACATGTCTTTCCAGGACCGAGACAGGTCGCCGAGG
``` a   L R S A I T G L V Y R K V L A L S S G S -

```
       AGAAAGGCCAGTGCGGTGGGTGATGTGGTCAATCTGGTGTCCGTGGACGTGCAGCGGCTG
1201 ──────+──────+──────+──────+──────+──────+  1260
       TCTTTCCGGTCACGCCACCCACTACACCAGTTAGACCACAGGCACCTGCACGTCGCCGAC
``` a   R K A S A V G D V V N L V S V D V Q R L -

Figure 15C

```
     ACCGAGAGCGTCCTCTACCTCAACGGGCTGTGGCTGCCTCTCGTCTGGATCGTGGTCTGC
1261 ------+--------+--------+---------+---------+---------+  1320
     TGGCTCTCGCAGGAGATGGAGTTGCCCGACACCGACGGAGAGCAGACCTAGCACCAGACG
``` a     T E S V L Y L N G L W L P L V W I V V C -

```
     TTCGTCTATCTCTGGCAGCTCCTGGGGCCCTCCGCCCTCACTGCCATCGCTGTCTTCCTG
1321 -------+---------+---------+---------+---------+---------+  1380
     AAGCAGATAGAGACCGTCGAGGACCCCGGGAGGCGGGAGTGACGGTAGCGACAGAAGGAC
``` a     F V Y L W Q L L G P S A L T A I A V F L -

```
     AGCCTCCTCCCTCTGAATTTCTTCATCTCCAAGAAAAGGAACCACCATCAGGAGGAGCAA
1381 ------+---------+---------+--------+---------+---------+  1440
     TCGGAGGAGGGAGACTTAAAGAAGTAGAGGTTCTTTTCCTTGGTGGTAGTCCTCCTCGTT
``` a     S L L P L N F F I S K K R N H H Q E E Q -

```
     ATGAGGCAGAAGGACTCACGGGCACGGCTCACCAGCTCTATCCTCAGGAACTCGAAGACC
1441 ------+---------+---------+---------+---------+---------+  1500
     TACTCCGTCTTCCTGAGTGCCCGTGCCGAGTGGTCGAGATAGGAGTCCTTGAGCTTCTGG
``` a     M R Q K D S R A R L T S S I L R N S K T -

```
     ATCAAGTTCCATGGCTGGGAGGGAGCCTTTCTGGACAGAGTCCTGGGCATCCGAGGCCAG
1501 ------+---------+---------+---------+---------+---------+  1560
     TAGTTCAAGGTACCGACCCTCCCTCGGAAAGACCTGTCTCAGGACCCGTAGGCTCCGGTC
``` a     I K F H G W E G A F L D R V L G I R G Q -

```
     GAGCTGGGCGCCTTGCGGACCTCCGGCCTCCTCTTCTCTGTGTCGCTGGTGTCCTTCCAA
1561 ------+---------+---------+---------+---------+---------+  1620
     CTCGACCCGCGGAACGCCTGGAGGCCGGAGGAGAAGAGACACAGCGACCACAGGAAGGTT
``` a     E L G A L R T S G L L F S V S L V S F Q -

```
     GTGTCTACATTTCTGGTCGCACTGGTGGTGTTTGCTGTCCACACTCTGGTGGCCGAGAAT
1621 ------+---------+---------+---------+---------+---------+  1680
     CACAGATGTAAAGACCAGCGTGACCACCACAAACGACAGGTGTGAGACCACCGGCTCTTA
``` a     V S T F L V A L V V F A V H T L V A E N -

Figure 15D

```
        GCTATGAATGCAGAGAAAGCCTTTGTGACTCTCACAGTTCTCAACATCCTCAACAAGGCC
    1681 --------+--------+--------+--------+--------+--------+  1740
        CGATACTTACGTCTCTTTCGGAAACACTGAGAGTGTCAAGAGTTGTAGGAGTTGTTCCGG
``` a    A M N A E K A F V T L T V L N I L N K A -

```
        CAGGCTTTCCTGCCCTTCTCCATCCACTCCCTCGTCCAGGCCCGGGTGTCCTTTGACCGT
    1741 --------+--------+--------+--------+--------+--------+  1800
        GTCCGAAAGGACGGGAAGAGGTAGGTGAGGGAGCAGGTCCGGGCCCACAGGAAACTGGCA
``` a    Q A F L P F S I H S L V Q A R V S F D R -

```
        CTGGTCACCTTCCTCTGCCTGGAAGAAGTTGACCCTGGTGTCGTAGACTCAAGTTCCTCT
    1801 --------+--------+--------+--------+--------+--------+  1860
        GACCAGTGGAAGGAGACGGACCTTCTTCAACTGGGACCACAGCATCTGAGTTCAAGGAGA
``` a    L V T F L C L E E V D P G V V D S S S -

```
        GGAAGCGCTGCCGGGAAGGATTGCATCACCATACACAGTGCCACCTTCGCCTGGTCCCAG
    1861 --------+--------+--------+--------+--------+--------+  1920
        CCTTCGCGACGGCCCTTCCTAACGTAGTGGTATGTGTCACGGTGGAAGCGGACCAGGGTC
``` a    G S A A G K D C I T I H S A T F A W S Q -

```
        GAAAGCCCTCCCTGCCTCCACAGAATAAACCTCACGGTGCCCCAGGGCTGTCTGCTGGCT
    1921 --------+--------+--------+--------+--------+--------+  1980
        CTTTCGGGAGGGACGGAGGTGTCTTATTTGGAGTGCCACGGGGTCCCGACAGACGACCGA
``` a    E S P P C L H R I N L T V P Q G C L L A -

```
        GTTGTCGGTCCAGTGGGGGCAGGGAAGTCCTCCCTGCTGTCCGCCCTCCTTGGGGAGCTG
    1981 --------+--------+--------+--------+--------+--------+  2040
        CAACAGCCAGGTCACCCCCGTCCCTTCAGGAGGGACGACAGGCGGGAGGAACCCCTCGAC
``` a    V V G P V G A G K S S L L S A L L G E L -

```
        TCAAAGGTGGAGGGGTTCGTGAGCATCGAGGGTGCTGTGGCCTACGTGCCCCAGGAGGCC
    2041 --------+--------+--------+--------+--------+--------+  2100
        AGTTTCCACCTCCCCAAGCACTCGTAGCTCCCACGACACCGGATGCACGGGGTCCTCCGG
``` a    S K V E G F V S I E G A V A Y V P Q E A -

```
        TGGGTGCAGAACACCTCTGTGGTAGAGAATGTGTGCTTCGGGCAGGAGCTGGACCCACCC
```

Figure 15E

```
                          2101 -------+--------+--------+--------+--------+--------+  2160
                               ACCCACGTCTTGTGGAGACACCATCTCTTACACACGAAGCCCGTCCTCGACCTGGGTGGG a      W  V  Q  N  T  S  V  V  E  N  V  C  F  G  Q  E  L  D  P  P  -

TGGCTGGAGAGAGTACTAGAAGCCTGTGCCCTGCAGCCAGATGTGGACAGCTTCCCTGAG
                          2161 -------+--------+--------+--------+--------+--------+  2220
                               ACCGACCTCTCTCATGATCTTCGGACACGGGACGTCGGTCTACACCTGTCGAAGGGACTC a      W  L  E  R  V  L  E  A  C  A  L  Q  P  D  V  D  S  F  P  E  -

GGAATCCACACTTCAATTGGGGAGCAGGGCATGAATCTCTCCGGAGGCCAGAAGCAGCGG
                          2221 -------+--------+--------+--------+--------+--------+  2280
                               CCTTAGGTGTGAAGTTAACCCCTCGTCCCGTACTTAGAGAGGCCTCCGGTCTTCGTCGCC a      G  I  H  T  S  I  G  E  Q  G  M  N  L  S  G  G  Q  K  Q  R  -

CTGAGCCTGGCCCGGGCTGTATACAGAAAGGCAGCTGTGTACCTGCTGGATGACCCCCTG
                          2281 -------+--------+--------+--------+--------+--------+  2340
                               GACTCGGACCGGGCCCGACATATGTCTTTCCGTCGACACATGGACGACCTACTGGGGGAC a      L  S  L  A  R  A  V  Y  R  K  A  A  V  Y  L  L  D  D  P  L  -

GCGGCCCTGGATGCCCACGTTGGCCAGCATGTCTTCAACCAGGTCATTGGGCCTGGTGGG
                          2341 -------+--------+--------+--------+--------+--------+  2400
                               CGCCGGGACCTACGGGTGCAACCGGTCGTACAGAAGTTGGTCCAGTAACCCGGACCACCC a      A  A  L  D  A  H  V  G  Q  H  V  F  N  Q  V  I  G  P  G  G  -

CTACTCCAGGGAACAACACGGATTCTCGTGACGCACGCACTCCACATCCTGCCCCAGGCT
                          2401 -------+--------+--------+--------+--------+--------+  2460
                               GATGAGGTCCCTTGTTGTGCCTAAGAGCACTGCGTGCGTGAGGTGTAGGACGGGGTCCGA a      L  L  Q  G  T  T  R  I  L  V  T  H  A  L  H  I  L  P  Q  A  -

GATTGGATCATAGTGCTGGCAAATGGGGCCATCGCAGAGATGGGTTCCTACCAGGAGCTT
                          2461 -------+--------+--------+--------+--------+--------+  2520
                               CTAACCTAGTATCACGACCGTTTACCCCGGTAGCGTCTCTACCCAAGGATGGTCCTCGAA a      D  W  I  I  V  L  A  N  G  A  I  A  E  M  G  S  Y  Q  E  L  -

CTGCAGAGGAAGGGGGCCCTCGTGTGTCTTCTGGATCAAGCCAGACAGCCAGGAGATAGA
                          2521 -------+--------+--------+--------+--------+--------+  2580
```

Figure 15F

```
                GACGTCTCCTTCCCCCGGGAGCACACAGAAGACCTAGTTCGGTCTGTCGGTCCTCTATCT a      L  Q  R  K  G  A  L  V  C  L  L  D  Q  A  R  Q  P  G  D  R   -

GGAGAAGGAGAAACAGAACCTGGGACCAGCACCAAGGACCCCAGAGGCACCTCTGCAGGC
     2581   ———+———+———+———+———+———+   2640
            CCTCTTCCTCTTTGTCTTGGACCCTGGTCGTGGTTCCTGGGGTCTCCGTGGAGACGTCCG a      G  E  G  E  T  E  P  G  T  S  T  K  D  P  R  G  T  S  A  G   -

AGGAGGCCCGAGCTTAGACGCGAGAGGTCCATCAAGTCAGTCCCTGAGAAGGACCGTACC
     2641   ———+———+———+———+———+———+   2700
            TCCTCCGGGCTCGAATCTGCGCTCTCCAGGTAGTTCAGTCAGGGACTCTTCCTGGCATGG a      R  R  P  E  L  R  R  E  R  S  I  K  S  V  P  E  K  D  R  T   -

ACTTCAGAAGCCCAGACAGAGGTTCCTCTGGATGACCCTGACAGGGCAGGATGGCCAGCA
     2701   ———+———+———+———+———+———+   2760
            TGAAGTCTTCGGGTCTGTCTCCAAGGAGACCTACTGGGACTGTCCCGTCCTACCGGTCGT a      T  S  E  A  Q  T  E  V  P  L  D  D  P  D  R  A  G  W  P  A   -

GGAAAGGACAGCATCCAATACGGCAGGGTGAAGGCCACAGTGCACCTGGCCTACCTGCGT
     2761   ———+———+———+———+———+———+   2820
            CCTTTCCTGTCGTAGGTTATGCCGTCCCACTTCCGGTGTCACGTGGACCGGATGGACGCA a      G  K  D  S  I  Q  Y  G  R  V  K  A  T  V  H  L  A  Y  L  R   -

GCCGTGGGCACCCCCCTCTGCCTCTACGCACTCTTCCTCTTCCTCTGCCAGCAAGTGGCC
     2821   ———+———+———+———+———+———+   2880
            CGGCACCCGTGGGGGGAGACGGAGATGCGTGAGAAGGAGAAGGAGACGGTCGTTCACCGG a      A  V  G  T  P  L  C  L  Y  A  L  F  L  F  L  C  Q  Q  V  A   -

TCCTTCTGCCGGGGCTACTGGCTGAGCCTGTGGGCGGACGACCCTGCAGTAGGTGGGCAG
     2881   ———+———+———+———+———+———+   2940
            AGGAAGACGGCCCCGATGACCGACTCGGACACCCGCCTGCTGGGACGTCATCCACCCGTC a      S  F  C  R  G  Y  W  L  S  L  W  A  D  D  P  A  V  G  G  Q   -

CAGACGCAGGCAGCCCTGCGTGGCGGGATCTTCGGGCTCCTCGGCTGTCTCCAAGCCATT
     2941   ———+———+———+———+———+———+   3000
            GTCTGCGTCCGTCGGGACGCACCGCCCTAGAAGCCCGAGGAGCCGACAGAGGTTCGGTAA
```

GGGCTGTTTGCCTCCATGGCTGCGGTGCTCCTAGGTGGGGCCCGGGCATCCAGGTTGCTC
3001 ------+------+------+------+------+------+  3060
     CCCGACAAACGGAGGTACCGACGCCACGAGGATCCACCCCGGGCCCGTAGGTCCAACGAG a    G L F A S M A A V L L G G A R A S R L L  -

TTCCAGAGGCTCCTGTGGGATGTGGTGCGATCTCCCATCAGCTTCTTTGAGCGGACACCC
3061 ------+------+------+------+------+------+  3120
     AAGGTCTCCGAGGACACCCTACACCACGCTAGAGGGTAGTCGAAGAAACTCGCCTGTGGG a    F Q R L L W D V V R S P I S F F E R T P  -

ATTGGTCACCTGCTAAACCGCTTCTCCAAGGAGACAGACACGGTTGACGTGGACATTCCA
3121 ------+------+------+------+------+------+  3180
     TAACCAGTGGACGATTTGGCGAAGAGGTTCCTCTGTCTGTGCCAACTGCACCTGTAAGGT a    I G H L L N R F S K E T D T V D V D I P  -

GACAAACTCCGGTCCCTGCTGATGTACGCCTTTGGACTCCTGGAGGTCAGCCTGGTGGTG
3181 ------+------+------+------+------+------+  3240
     CTGTTTGAGGCCAGGGACGACTACATGCGGAAACCTGAGGACCTCCAGTCGGACCACCAC a    D K L R S L L M Y A F G L L E V S L V V  -

GCAGTGGCTACCCCACTGGCCACTGTGGCCATCCTGCCACTGTTTCTCCTCTACGCTGGG
3241 ------+------+------+------+------+------+  3300
     CGTCACCGATGGGGTGACCGGTGACACCGGTAGGACGGTGACAAAGAGGAGATGCGACCC a    A V A T P L A T V A I L P L F L L Y A G  -

TTTCAGAGCCTGTATGTGGTTAGCTCATGCCAGCTGAGACGCTTGGAGTCAGCCAGCTAC
3301 ------+------+------+------+------+------+  3360
     AAAGTCTCGGACATACACCAATCGAGTACGGTCGACTCTGCGAACCTCAGTCGGTCGATG a    F Q S L Y V V S S C Q L R R L E S A S Y  -

TCGTCTGTCTGCTCCCACATGGCTGAGACGTTCCAGGGCAGCACAGTGGTCCGGGCATTC
3361 ------+------+------+------+------+------+  3420
     AGCAGACAGACGAGGGTGTACCGACTCTGCAAGGTCCCGTCGTGTCACCAGGCCCGTAAG
```

Figure 15H a    S  S  V  C  S  H  M  A  E  T  F  Q  G  S  T  V  V  R  A  F  -

```
     CGAACCCAGGCCCCTCTTGTGGCTCAGAACAATGCTCGCGTAGATGAAAGCCAGAGGATC
3421 ------+---------+---------+---------+---------+---------+ 3480
     GCTTGGGTCCGGGGAGAACACCGAGTCTTGTTACGAGCGCATCTACTTTCGGTCTCCTAG
``` a    R  T  Q  A  P  L  V  A  Q  N  N  A  R  V  D  E  S  Q  R  I  -

```
     AGTTTCCCGCGACTGGTGGCTGACAGGTGGCTTGCGGCCAATGTGGAGCTCCTGGGGAAT
3481 ------+---------+---------+---------+---------+---------+ 3540
     TCAAAGGGCGCTGACCACCGACTGTCCACCGAACGCCGGTTACACCTCGAGGACCCCTTA
``` a    S  F  P  R  L  V  A  D  R  W  L  A  A  N  V  E  L  L  G  N  -

```
     GGCCTGGTGTTTGCAGCTGCCACGTGTGCTGTGCTGAGCAAAGCCCACCTCAGTGCTGGC
3541 ------+---------+---------+---------+---------+---------+ 3600
     CCGGACCACAAACGTCGACGGTGCACACGACACGACTCGTTTCGGGTGGAGTCACGACCG
``` a    G  L  V  F  A  A  A  T  C  A  V  L  S  K  A  H  L  S  A  G  -

```
     CTCGTGGGCTTCTCTGTCTCTGCTGCCCTCCAGGTGACCCAGGCACTGCAGTGGGTTGTT
3601 ------+---------+---------+---------+---------+---------+ 3660
     GAGCACCCGAAGAGACAGAGACGACGGGAGGTCCACTGGGTCCGTGACGTCACCCAACAA
``` a    L  V  G  F  S  V  S  A  A  L  Q  V  T  Q  A  L  Q  W  V  V  -

```
     CGCAACTGGACAGACCTAGAGAACAGCATCGTGTCAGTGGAGCGGATGCAGGACTATGCC
3661 ------+---------+---------+---------+---------+---------+ 3720
     GCGTTGACCTGTCTGGATCTCTTGTCGTAGCACAGTCACCTCGCCTACGTCCTGATACGG
``` a    R  N  W  T  D  L  E  N  S  I  V  S  V  E  R  M  Q  D  Y  A  -

```
     TGGACGCCCAAGGAGGCTCCCTGGAGGCTGCCCACATGTGCAGCTCAGCCCCCCTGGCCT
3721 ------+---------+---------+---------+---------+---------+ 3780
     ACCTGCGGGTTCCTCCGAGGGACCTCCGACGGGTGTACACGTCGAGTCGGGGGGACCGGA
``` a    W  T  P  K  E  A  P  W  R  L  P  T  C  A  A  Q  P  P  W  P  -

```
     CAGGGCGGGCAGATCGAGTTCCGGGACTTTGGGCTAAGATACCGACCTGAGCTCCCGCTG
3781 ------+---------+---------+---------+---------+---------+ 3840
     GTCCCGCCCGTCTAGCTCAAGGCCCTGAAACCCGATTCTATGGCTGGACTCGAGGGCGAC
``` a    Q  G  G  Q  I  E  F  R  D  F  G  L  R  Y  R  P  E  L  P  L

Figure 15I

```
     GCTGTGCAGGGCGTGTCCCTCAAGATCCACGCAGGAGAGAAGGTGGGCATCGTTGGCAGG
3841 ------+---------+--------+---------+---------+---------+  3900
     CGACACGTCCCGCACAGGGAGTTCTAGGTGCGTCCTCTCTTCCACCCGTAGCAACCGTCC
``` a   A V Q G V S L K I H A G E K V G I V G R -

```
     ACCGGGGCAGGGAAGTCCTCCCTGGCCAGTGGGCTGCTGCGGCTCCAGGAGGCAGCTGAG
3901 ---------+--------+--------+---------+---------+---------+  3960
     TGGCCCCGTCCCTTCAGGAGGGACCGGTCACCCGACGACGCCGAGGTCCTCCGTCGACTC
``` a   T G A G K S S L A S G L L R L Q E A A E -

```
     GGTGGGATCTGGATCGACGGGGTCCCCATTGCCCACGTGGGGCTGCACACACTGCGCTCC
3961 --------+--------+--------+--------+---------+--------+  4020
     CCACCCTAGACCTAGCTGCCCCAGGGGTAACGGGTGCACCCCGACGTGTGTGACGCGAGG
``` a   G G I W I D G V P I A H V G L H T L R S -

```
     AGGATCAGCATCATCCCCCAGGACCCCATCCTGTTCCCTGGCTCTCTGCGGATGAACCTC
4021 --------+--------+---------+---------+--------+--------+  4080
     TCCTAGTCGTAGTAGGGGGTCCTGGGGTAGGACAAGGGACCGAGAGACGCCTACTTGGAG
``` a   R I S I I P Q D P I L F P G S L R M N L -

```
     GACCTGCTGCAGGAGCACTCGGACGAGGCTATCTGGGCAGCCCTGGAGACGGTGCAGCTC
4081 ---------+--------+--------+---------+--------+--------+  4140
     CTGGACGACGTCCTCGTGAGCCTGCTCCGATAGACCCGTCGGGACCTCTGCCACGTCGAG
``` a   D L L Q E H S D E A I W A A L E T V Q L -

```
     AAAGCCTTGGTGGCCAGCCTGCCCGGCCAGCTGCAGTACAAGTGTGCTGACCGAGGCGAG
4141 --------+---------+---------+---------+---------+--------+  4200
     TTTCGGAACCACCGGTCGGACGGGCCGGTCGACGTCATGTTCACACGACTGGCTCCGCTC
``` a   K A L V A S L P G Q L Q Y K C A D R G E -

```
     GACCTGAGCGTGGGCCAGAAACAGCTCCTGTGTCTGGCACGTGCCCTTCTCCGGAAGACC
4201 --------+--------+--------+---------+---------+---------+  4260
     CTGGACTCGCACCCGGTCTTTGTCGAGGACACAGACCGTGCACGGGAAGAGGCCTTCTGG
``` a   D L S V G Q K Q L L C L A R A L L R K T -

Figure 15J

```
      CAGATCCTCATCCTGGACGAGGCTACTGCTGCCGTGGACCCTGGCACGGAGCTGCAGATG
4261 ——————+—————+————+————+————+————+   4320
      GTCTAGGAGTAGGACCTGCTCCGATGACGACGGCACCTGGGACCGTGCCTCGACGTCTAC a     Q I L I L D E A T A A V D P G T E L Q M  -

CAGGCCATGCTCGGGAGCTGGTTTGCACAGTGCACTGTGCTGCTCATTGCCCACCGCCTG
4321 ——————+—————+————+————+————+————+   4380
      GTCCGGTACGAGCCCTCGACCAAACGTGTCACGTGACACGACGAGTAACGGGTGGCGGAC a     Q A M L G S W F A Q C T V L L I A H R L  -

CGCTCCGTGATGGACTGTGCCCGGGTTCTGGTCATGGACAAGGGGCAGGTGGCAGAGAGC
4381 ——————+—————+————+————+————+————+   4440
      GCGAGGCACTACCTGACACGGGCCCAAGACCAGTACCTGTTCCCCGTCCACCGTCTCTCG a     R S V M D C A R V L V M D K G Q V A E S  -

GGCAGCCCGGCCCAGCTGCTGGCCCAGAAGGGCCTGTTTTACAGACTGGCCCAGGAGTCA
4441 ——————+—————+————+————+————+————+   4500
      CCGTCGGGCCGGGTCGACGACCGGGTCTTCCCGGACAAAATGTCTGACCGGGTCCTCAGT a     G S P A Q L L A Q K G L F Y R L A Q E S  -

GGCCTGGTCTGA
4501 ——————+—  4512
      CCGGACCAGACT a     G L V *  -
```

MRP-RELATED ABC TRANSPORTER ENCODING NUCLEIC ACIDS AND METHODS OF USE THEREOF

This application is a divisional application of U.S. application 09/647,140, filed Sep. 27, 2000, now U.S. Pat. 6,803,184, which is a U.S. National Phase of PCT/US99/06644, filed Mar. 26, 1999, which in turn claims priority to U.S. Provisional Applications, 60/095,153, filed Aug. 3, 1998, and Ser. No. 60/079,759, filed Mar. 27, 1998.

Pursuant to 35 U.S.C. §202(c) it is acknowledged that the U.S. Government has certain rights in the invention described herein, which was made in part with funds from the National Institutes of Health, Grant Numbers, CA63173 and CA06927.

FIELD OF THE INVENTION

The present invention relates to the fields of medicine and molecular biology. More specifically, the invention provides nucleic acid molecules and proteins encoded thereby which are involved in the development of resistance to pharmacological and chemotherapeutic agents in tumor cells.

BACKGROUND OF THE INVENTION

Several publications are referenced in this application in parentheses in order to more fully describe the state of the art to which this invention pertains. The disclosure of each of these publications is incorporated by reference herein.

P-glycoprotein, the product of the MDR1 gene, was the first ABC transporter shown to confer resistance to cytotoxic agents. Pgp functions as an ATP-dependent efflux pump that reduces the intracellular concentration of a variety of chemotherapeutic agents by transporting them across the plasma membrane (1). The multidrug resistance phenotype associated with overexpression of Pgp is of considerable clinical interest because natural product drugs are second only to alkylating agents in clinical utility, and many effective chemotherapeutic regimens contain more than one natural product agent. More recently, we and others have reported transfection studies indicating that MRP, another ABC family transporter, confers a multidrug resistance phenotype that includes many natural product drugs, but is distinct from the resistance phenotype associated with Pgp (2-6). MRP shares only limited amino acid identity with Pgp, and this is reflected in the different substrate specificities of the two transporters. In contrast to Pgp, MRP can transport a wide range of anionic organic conjugates, including glutathione S-conjugates (7). In addition to Pgp and MRP there may be other transporters that are involved in cytotoxic drug resistance. In the case of natural product drugs, resistant cell lines have been described that display a multidrug resistant phenotype associated with a drug accumulation deficit, but do not overexpress Pgp or MRP (8). ABC transporters have also been linked to cisplatin resistance, and several lines of evidence suggest the possibility that pumps specific for organic anions may be involved: 1) decreased cisplatin accumulation is consistently observed in cisplatin resistant cell lines (9); 2) cisplatin is conjugated to glutathione in the cell, and this anionic conjugate is toxic in an in vitro biochemical assay (10); and 3) biochemical studies using membrane vesicle preparations have shown that cisplatin resistant cells lines have enhanced expression of an ATP-dependent transporter of CDDP-glutathione and other glutathione S-conjugates such as the cystinyl leukotriene $LTC_4$ (11, 12). These data thus suggest that an organic anion transporter may contribute to cisplatin resistance by exporting CDDP-glutathione. While MRP is an organic anion transporter, the reported drug resistance profile of MRP-transfected cells does not extend to this agent (5, 6), and to date only one cisplatin resistant cell line has been reported to overexpress MRP (13). This suggests that organic anion transporters other than MRP may contribute to cisplatin resistance. Consistent with this possibility, the canalicular multispecific organic anion transporter, cMOAT, an MRP-related transporter that functions as the major organic anion transporter in liver, has been reported to be overexpressed in cisplatin resistant cell lines (14, 15). A more direct link between cMOAT and cytotoxic drug resistance is suggested by a recent report in which transfection of a cMOAT antisense construct into a liver cancer cell line resulted in sensitization to cisplatin, daunorubicin and other cytotoxic agents (16).

Clearly, a need exists for identifying the essential components and mechanisms giving rise to drug resistance and the transport of anticancer agents out of the tumor cell. The elucidation of these mechanisms may be used to advantage for the design of efficacious chemotherapeutic agents.

SUMMARY OF THE INVENTION

This invention provides novel, biological molecules useful for identification, detection, and/or molecular characterization of components involved in the acquisition of drug resistance in tumor cells. According to one aspect of the invention, an isolated nucleic acid molecule is provided which includes a sequence encoding a protein transporter of a size between about 1300 and 1350 amino acids in length. The encoded protein, referred to herein as MOAT-B, comprises a multi-domain structure including a tandem repeat of nucleotide binding folds appended C-terminal to a hydrophobic domain that contains several potential membrane spanning helices. Conserved Walker A and B ATP binding sites are present in each of the nucleotide binding folds.

In a preferred embodiment of the invention, an isolated nucleic acid molecule is provided that includes a cDNA encoding a human MOAT-B protein. In a particularly preferred embodiment, the human MOAT-B protein has an amino acid sequence the same as Sequence I.D. No. 2. An exemplary MOAT-B nucleic acid molecule of the invention comprises Sequence I.D. No. 1.

According to another aspect of the invention, a second isolated nucleic acid molecule is provided which includes a sequence encoding a transporter between about 1400 and 1450 amino acids. The encoded protein, referred to herein as MOAT-C contains a multi-domain structure including a tandem repeat of nucleotide binding folds appended C-terminal to a hydrophobic domain that contains several potential membrane spanning helices. Conserved Walker A and B ATP binding sites are present in each of the nucleotide binding folds. While similar in structure to MOAT-B described above, MOAT-C contains distinct sequence differences.

In a preferred embodiment of the invention, an isolated nucleic acid molecule is provided that includes a cDNA encoding a human MOAT-C protein. In a particularly preferred embodiment, the human MOAT-C protein has an amino acid sequence the same as Sequence I.D. No. 4. An exemplary MOAT-C nucleic acid molecule of the invention comprises Sequence I.D. No. 3.

According to yet another aspect of the invention, an isolated nucleic acid molecule is provided which includes a sequence encoding a protein of a size between about 1500 and 1550 amino acids in length. The encoded protein, referred to herein as MOAT-D, contains a multidomain structure including an N-terminal hydrophobic extension which harbors five transmembrane spanning helices.

In a preferred embodiment of the invention, an isolated nucleic acid molecule is provided that includes a cDNA encoding a MOAT-D protein. In a particularly preferred embodiment, the human MOAT-D protein has an amino acid sequence the same as Sequence I.D. No. 6. An exemplary MOAT-D nucleic acid molecule of the invention comprises Sequence I.D. No. 5.

According to yet another aspect of the invention, an isolated nucleic acid molecule is provided which includes a sequence encoding a protein of a size between about 1480 and 1530 amino acids in length. The encoded protein, referred to herein as MOAT-E, contains a multidomain structure including an N-terminal hydrophobic extension which harbors several transmembrane spanning helices. While similar in structure to MOAT-D described above, MOAT-E contains distinct sequence differences.

In a preferred embodiment of the invention, an isolated nucleic acid molecule is provided that includes a cDNA encoding a MOAT-E protein. In a particularly preferred embodiment, the human MOAT-E protein has an amino acid sequence the same as Sequence I.D. No. 8. An exemplary MOAT-E nucleic acid molecule of the invention comprises Sequence I.D. No. 7.

According to another aspect of the present invention, an isolated nucleic acid molecule is provided, which has a sequence selected from the group consisting of: (1) Sequence I.D. No. 1; (2) a sequence specifically hybridizing with preselected portions or all of the complementary strand of Sequence I.D. No. 1 comprising nucleic acids encoding amino acids 1-1154 of Sequence ID No. 2; (3) a sequence encoding preselected portions of Sequence I.D. No. 1 within nucleotides 1-3462, (4) Sequence I.D. No. 3; (5) a sequence specifically hybridizing with preselected portions or all of the complementary strand of Sequence I.D. No. 3 comprising nucleic acids encoding amino acids 1-442 of Sequence ID No. 4; (6) a sequence encoding preselected portions of Sequence I.D. No. 3 within nucleotides 1-1326, (7) Sequence I.D. No. 5; (8) a sequence specifically hybridizing with preselected portions or all of the complementary strand of Sequence I.D. No. 5 comprising nucleic acids encoding amino acids 1-1036 of Sequence ID No. 6; (9) a sequence encoding preselected portions of Sequence I.D. No. 5 within nucleotides 1-3108, (1) Sequence I.D. No. 7; (2) a sequence specifically hybridizing with preselected portions or all of the complementary strand of Sequence I.D. No. 7 comprising nucleic acids encoding amino acids 1-998 of Sequence ID No. 8; (3) a sequence encoding preselected portions of Sequence I.D. No. 7 within nucleotides 1-300.

Such partial sequences are useful as probes to identify and isolate homologues of the MOAT genes of the invention. Additionally, isolated nucleic acid sequences encoding natural allelic variants of the nucleic acids of Sequence I.D. Nos., 1, 3, 5 and 7 are also contemplated to be within the scope of the present invention. The term natural allelic variants will be defined hereinbelow.

According to another aspect of the present invention, antibodies immunologically specific for the human MOAT proteins described hereinabove are provided.

In yet another aspect of the invention, host cells comprising at least one of the MOAT encoding nucleic acids are provided. Such host cells include but are not limited to bacterial cells, fungal cells, insect cells, mammalian cells, and plant cells. Host cells overexpressing one or more of the MOAT encoding nucleic acids of the invention provide valuable research tools for assessing transport of chemotherapeutic agents out of cells. MOAT expressing cells also comprise a biological system useful in methods for identifying inhibitors of the MOAT transporters.

Another embodiment of the present invention encompasses methods for screening cells expressing MOAT encoding nucleic acids for chemotherapy resistance. Such methods will provide the clinician with data which correlates expression of a particular MOAT genes with a particular chemotherapy resistant phenotype.

Diagnostic methods are also contemplated in the present invention. Accordingly, suitable oligonucleotide probes are provided which hybridize to the nucleic acids of the invention. Such probes may be used to advantage in screening biopsy samples for the expression of particular MOAT genes. Once a tumor sample has been characterized as to the MOAT gene(s) expressed therein, inhibitors identified in the cell line screening methods described above may be administered to prevent efflux of the beneficial chemotherapeutic agents from cancer cells.

The methods of the invention may be applied to kits. An exemplary kit of the invention comprises MOAT gene specific oligonucleotide probes and/or primers, MOAT encoding DNA molecules for use as a positive control, buffers, and an instruction sheet. A kit for practicing the cell line screening method includes frozen cells comprising the MOAT genes of the invention, suitable culture media, buffers and an instruction sheet.

In a further aspect of the invention, transgenic knockout mice are disclosed. Mice will be generated in which at least one MOAT gene has been knocked out. Such mice will provide a valuable in biological system for assessing resistance to chemotherapy in an in vivo tumor model.

Various terms relating to the biological molecules of the present invention are used hereinabove and also throughout the specification and claims. The terms "percent similarity" and "percent identity (identical)" are used as set forth in the UW GCG Sequence Analysis program (Devereux et al. NAR 12:387-397 (1984)).

With reference to nucleic acids of the invention, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the genomic DNA of a prokaryote or eukaryote.

With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form (the term "substantially pure" is defined below).

With respect to protein, the term "isolated protein" or "isolated and purified protein" is sometimes used herein. This term refers primarily to a protein produced by expression of an isolated nucleic acid molecule of the invention. Alternatively, this term may refer to a protein which has been sufficiently separated from other proteins with which it would naturally be associated, so as to exist in "substantially pure" form.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, the compound of interest. Purity is measured by methods appropriate for the compound of interest (e.g. chromatographic methods, agarose or polyacrylamide gel electrophoresis, HPLC analysis, and the like). With respect to antibodies of the invention, the term "immunologically specific" refers to antibodies that bind to one or more epitopes of a protein of interest (e.g., MOAT-B, MOAT-C or MOAT-D), but which do not substantially recognize and bind other molecules in a sample containing a mixed population of antigenic biological molecules.

With respect to nucleic acids and oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). When used in reference to a double stranded nucleic acid, this term is intended to signify that the double stranded nucleic acid has been subjected to denaturing conditions, as is well known to those of skill in the art. In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

One common formula for calculating the stringency conditions required to achieve hybridization between nucleic acid molecules of a specified sequence homology (Sambrook et al., 1989):

$$T_m = 81.5° \text{C.} + 16.6 \text{ Log[Na+]} + 0.41(\% \ G+C) - 0.63(\% \text{ formamide}) - 600/\#bp \text{ in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C. Such sequences would be considered substantially homologous to the nucleic acid sequences of the invention.

The nucleic acids, proteins, antibodies, cell lines, methods, and kits of the present invention may be used to advantage to identify targets for the development of novel agents which inhibit the aberrant transport of cytoxic agents out of tumor cells. The transgenic mice of the invention may be used an in vivo model for chemotherapy resistance.

The human MOAT molecules methods and kits described above may also be used as research tools and will facilitate the elucidation of the mechanism by which tumor cells acquire a drug resistant phenotype.

BRIEF DESCRIPTION OF THE DRAWINGS

FIGS. 1A and 1B show the predicted structure of MOAT-B (SEQ ID NO: 2) and comparison with human MRP (SEQ ID NO: 19). The vertical lines indicate identical amino acids and the vertical dots indicate conserved amino acids. Gaps are indicated by periods. The overbars indicate potential transmembrane spanning segments as predicted by the TMAP program. The first and second nucleotide binding folds (NBF 1 and NBF 2) are indicated by horizontal arrows. The C-terminal 34 amino acids (residues 1291-1325) are replaced in the second class of MOAT-B cDNA clones by the following amino acids: ILQKKLSTYWSH (SEQ ID NO: 20). The Alignment was performed using the GAP program (gap weight 3.0, length weight 0.1) in the Genetics Computer Group Package. H. MRP: human MRP.

FIG. 2A shows the comparison of the nucleotide binding folds of MOAT-B (residues 428 to 577 of SEQ ID NO: 2; residues 1058 to 1216 of SEQ ID NO: 2). Amino acids that are identical to those of MOAT-B are shaded, and gaps are indicated by periods. Walker A and B motifs, and the ABC transporter family signature sequence C, are underlined. Amino acid positions are indicated to the right. Amino acid sequences were aligned using the PILEUP program (gap weight 3.0, length weight 0.1) in the Genetics Computer Group Package. FIG. 2B shows a comparison of the MOAT-B hydropathy profile. To facilitate comparison, the proteins are aligned so that the N-terminal nucleotide binding folds (NBF) are roughly in register. NBF's are indicated by bars. Values above and below the horizontal lines indicate hydrophobic and hydrophilic regions, respectively. Hydrophobicity plots were generated using the Kyte-Doolittle algorithm with a window of 7 residues. The transporters shown are: human multidrug-associated protein, H. MRP (P33529; residues 661 to 810 of SEQ ID NO: 19; residues 1310 to 1469 of SEQ ID NO: 19); human multispecific organic anion transporter, H. MOAT (U63970; SEQ ID NO: 23; SEQ ID NO: 24); Saccharomyces cerevisiae yeast cadmium factor 1, S. YCF1 (P39109; SEQ ID NO: 21; SEQ ID NO: 22); rat sulfonylurea receptor, R. SUR (Q09427; SEQ ID NO: 29; SEQ ID NO: 30); human cystic fibrosis transmembrane conductance regulator, H. CFTR (M28668; SEQ ID NO: 25; SEQ ID NO: 26); Leishmania P-glycoprotein, L. PgpA (P21441; SEQ ID NO: 27; SEQ ID NO: 28) and human mdr1 gene product, H. MDR1 (P08183; SEQ ID NO: 31; SEQ ID NO: 32). Accession numbers and sequence identifiers for the NBF I and NBF II, respectively, are shown in parentheses.

FIGS. 5A and 5B show the predicted structures of MOAT-C and MOAT-D. FIG. 5A presents the structure of MOAT-C (SEQ ID NO: 4). FIG. 5B shows the structure of MOAT-D (SEQ ID NO: 33). Numbered overbars indicate potential transmembrane spanning helices. Horizontal arrows indicate the positions of the amino terminal (NBF1) and C-terminal (NBF2) nucleotide binding folds. Walker A and B motifs, and the ABC transporter family signature sequence C are underlined. Bullets indicate the positions of potential N-linked glycosylation sites that are conserved with previously reported N-glycosylation sites in MRP. The indicated MOAT-C transmembrane spanning helices were predicted using the TMAP program and an input alignment of MOAT-B and MOAT-C. The indicated MOAT-D transmembrane helices are based upon inspection of an alignment with MRP.

FIGS. 6A and 6B show a comparison of the nucleotide binding folds and hydropathy profiles of MOAT-C (residues 578 to 727 of SEQ ID NO: 4; residues 1210 to 1369 of SEQ ID NO: 4) and MOAT-D (residues 644 to 793 of SEQ ID NO: 6; residues 1306 to 1465 of SEQ ID NO: 6) with those of other related ABC transporters including MOAT-B (residues 428 to 577 of SEQ ID NO: 2; residues 1058 to 1216 of SEQ ID NO: 2). FIG. 6A depicts the comparison of the nucleotide binding folds. The alignment was produced using the PILEUP command (gap weight 3.0, length weight 0.1) in the Genetics Computer Group Package Version 9.1. Amino acid positions conserved in at least 4 of the 8 proteins are shaded. Periods indicate gaps in the alignment. Walker A and B, and the ABC transporter family signature sequence C are indicated by underbars. FIG. 6B shows the comparison of hydropathy profiles. To facilitate comparisons, gaps were introduced at the N-termini of some proteins in order to bring the first nucleotide binding folds into register. Nucleotide binding folds are indicated by bars. Values above and below the horizontal lines indicate hydrophobic and hydrophilic regions, respectively. Hydrophobicity plots were generated using the Kyte-Doolittle algorithm with a window of 7 residues. Accession numbers are as follows: MRP, P33529 (residues 661 to 810 of SEQ ID NO: 19; residues 1310 to 1469 of SEQ ID NO: 19); cMOAT, U63970 SEQ ID NO: 23; SEQ ID NO: 24); SUR, Q09428 (SEQ ID NO: 29; SEQ ID NO: 30); CFTR, P-13569 (SEQ ID NO: 25; SEQ ID NO: 26); MDR1, P08183 (SEQ ID NO: 31; SEQ ID NO: 32)

FIG. 8A shows the localization of MOAT-C. Hybridization signals at chromosome 3q27 in two metaphase spreads are indicated by arrows (top). The inset shows paired hybridization signals at band q27 of chromosome 3 from three other metaphase spreads. FIG. 8B shows the localization of MOAT-D. Hybridization signals at chromosome 17q21-22 in two metaphase spreads are indicated by arrows (top). The inset shows paired hybridization signals at band q21-22 of chromosome 17 from three other metaphase spreads.

FIG. 9 shows predicted amino acid sequence of MOAT- E (SEQ ID NO: 8). Also shown are the location of the potential transmembrane helices (overbars), the potential—glycosylation site (black dot) and the two nucleotide binding folds (NBF1 and NBF2). Walker A and B motifs, as well as the signature C motif of ABC transporters, are also indicated.

FIGS. 12A-12J show the cDNA (SEQ ID NO: 1) and amino acid sequences (SEQ ID NO: 2)encoded by MOATB.

FIGS. 13A-13K show the cDNA (SEQ ID NO: 3) and amino acid sequences (SEQ ID NO: 4) encoded by MOATC.

FIGS. 14A-14K show the cDNA (SEQ ID NO: 5) and amino acid sequences (SEQ ID NO: 6) encoded by MOATD.

FIGS. 15A-15K show the cDNA (SEQ ID NO: 7) and amino acid sequences (SEQ ID NO: 8) encoded by MOATE.

DETAILED DESCRIPTION OF THE INVENTION

Figures 2A, 2B:
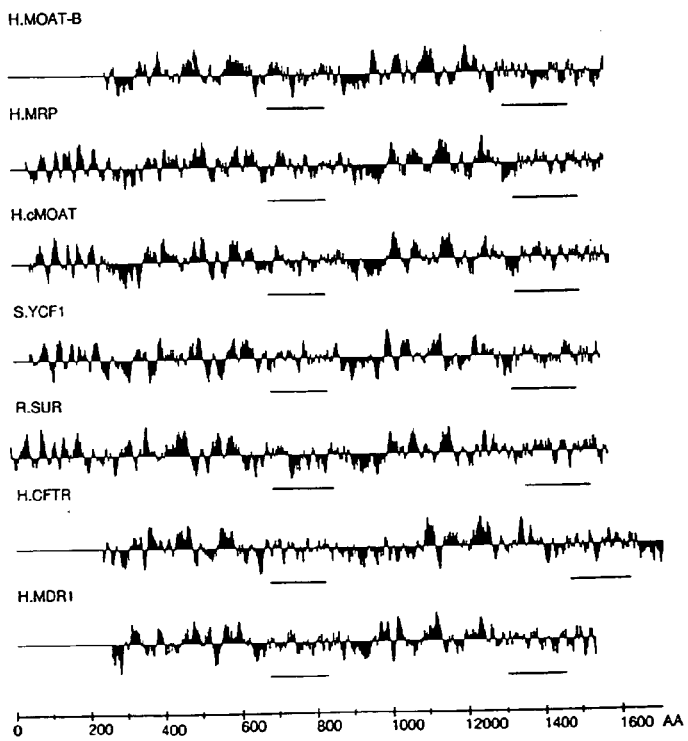
FIGS. 2A and 2B depict a comparison of the nucleotide binding folds and hydropathy profile of MOAT-B with those of other eukaryotic ABC transporters.

MRP and cMOAT are closely related mammalian ABC transporters that export organic anions from cells. Transfection studies have established that MRP confers resistance to natural product cytotoxic agents, and recent evidence suggests the possibility that cMOAT may contribute to cytotoxic drug resistance as well. Based upon the potential importance of these transporters in clinical drug resistance, and their important physiological roles in the export of the amphiphilic products of phase I and phase II metabolism, we sought to identify other MRP-related transporters. Using a degenerate PCR approach, a cDNA molecule was isolated which encodes a novel ABC transporter designated herein as MOAT-B. The MOAT-B gene was mapped using fluorescence in situ hybridization to chromosome band 13q32. Comparison of the MOAT-B predicted protein with other transporters revealed that it is most closely related to MRP, cMOAT, and the yeast organic anion transporter YCF1. While MOAT-B is closely related to these transporters, it is distinguished by the absence of approximately 200 amino acid N-terminal hydrophobic extension that is present in MRP and cMOAT, and which is predicted to encode several transmembrane spanning segments. In addition, the MOAT-B tissue distribution is distinct from MRP and cMOAT. In contrast to MRP, which is widely expressed in most tissues, including liver, and cMOAT, whose expression is largely restricted to liver, the MOAT-B transcript is widely expressed, with particularly high levels in prostate, but is barely detectable in liver. These data indicate that MOAT-B is a ubiquitously expressed transporter that is closely related to MRP and cMOAT, and indicate that it is an organic anion pump relevant to cellular detoxification.

Three additional MRP/cMOAT-related transporters, MOAT-C, MOAT-D and MOAT-E are also disclosed herein. MOAT-C encodes a 1437 amino acid protein that is most closely related to MRP, cMOAT and MOAT-B, among eukaryotic transporters (33% -37% identity). However, based upon amino acid identity, MOAT-C is considerably less related to MRP and cMOAT than the latter transporters are to each other (48% identity). In addition, the MOAT-C topology is distinct from that of MRP and cMOAT in that it, like MOAT-B, lacks an N-terminal transmembrane spanning domain. MOAT-D encodes a 1530 amino acid transporter that is highly related to MRP (57% identity) and cMOAT (47% identity). MOAT-E encodes 1503 amino acid transporter that is highly related to MOAT-D, MRP and cMOAT (39-45% identity). The topology of MOAT-D and MOAT-E are quite similar to MRP and cMOAT, in that they have an N-terminal hydrophobic extension that is predicted to harbor five transmembrane spanning helices. MOAT-C and MOAT-D were mapped to chromosome bands 3q27 and 17q21-22, respectively, by fluorescence in situ hybridization.

The expression patterns of MOAT-C, MOAT-D and MOAT-E are distinct from those of MRP, cMOAT and MOAT-B. MOAT-C transcript is widely expressed, with highest levels in skeletal muscle, kidney and testis, but is expressed at barely detectable levels in liver and lung. MOAT-D transcript has a more restricted expression pattern, with high levels in colon, pancreas, liver and kidney. Data presented herein reveal that MOAT-E expression is restricted to liver and kidney.

Based upon degree of amino acid identity, and protein topology, the MRP-related transporters fall into two groups, with the first group consisting of MRP, cMOAT, MOAT-D and MOAT-E, and the second group consisting of MOAT-B and MOAT-C. The isolation of MOAT-C, MOAT-D and MOAT-E thus helps to define the MRP/cMOAT subfamily. The high degree of amino acid identity and topological similarity of MOAT-D and MOAT-E to MRP and cMOAT suggest that they function as organic anion transporters, and play a role in cytotoxic drug resistance. In contrast, the lower degree of amino acid identify and distinct topology of MOAT-B and MOAT-C suggest the possibility that their substrate specificities and functions may be distinct from that of MRP, cMOAT, MOAT-D and MOAT-E.

The compositions, methods, kits and transgenic mice of the invention disclosed herein will facilitate the identification of drugs that cripple the ability of MOAT genes and proteins encoded thereby to effect the efflux of clinically beneficial pharmacological agents in malignant cells.

I. Preparation of MOAT-Encoding Nucleic Acid Molecules, MOAT Proteins, and Antibodies Thereto A. Nucleic Acid Molecules Nucleic acid molecules encoding the MOAT proteins of the invention may be prepared by two general methods: (1) synthesis from appropriate nucleotide triphosphates, or (2) isolation from biological sources. Both methods utilize protocols well known in the art. The availability of nucleotide sequence information, such as cDNAs having Sequence I.D. Nos. 1, 3, 5, or 7 enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a 5 kb double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire 5 kb double-stranded molecule. A synthetic DNA molecule so constructed may then be cloned and amplified in an appropriate vector.

Nucleic acid sequences encoding the MOAT proteins of the invention may be isolated from appropriate biological sources using methods known in the art. In a preferred embodiment, a cDNA clone is isolated from a cDNA expression library of human origin. In an alternative embodiment, utilizing the sequence information provided by the cDNA sequence, human genomic clones encoding MOAT proteins may be isolated. Alternatively, cDNA or genomic clones having homology with MOAT-B, MOAT-C, MOAT-D or MOAT-E may be isolated from other species using oligonucleotide probes corresponding to predetermined sequences within the MOAT encoding nucleic acids.

In accordance with the present invention, nucleic acids having the appropriate level of sequence homology with the protein coding region of Sequence I.D. Nos. 1, 3, 5, and 7 may be identified by using hybridization and washing conditions of appropriate stringency. For example, hybridizations may be performed, according to the method of Sambrook et al., (supra) using a hybridization solution comprising: 5×SSC, 5× Denhardt's reagent, 1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42-65° in 1×SSC and 1% SDS, changing the solution every 30 minutes.

Nucleic acids of the present invention may be maintained as DNA in any convenient cloning vector. In a preferred embodiment, clones are maintained in a plasmid cloning/expression vector, such as pBluescript (Stratagene, La Jolla, Calif.), which is propagated in a suitable E. coli host cell.

MOAT-encoding nucleic acid molecules of the invention include cDNA, genomic DNA, RNA, and fragments thereof which may be single-or double-stranded. Thus, this invention provides oligonucleotides (sense or antisense strands of DNA or RNA) having sequences capable of hybridizing with at least one sequence of a nucleic acid molecule of the present invention, such as selected segments of the cDNA having Sequence I.D. No. 1. Such oligonucleotides are useful as probes for detecting or isolating MOAT genes. Antisense nucleic acid molecules may be targeted to translation initiation sites and/or splice sites to inhibit the translation of the MOAT-encoding nucleic acids of the invention. Such antisense molecules are typically between 15 and 30 nucleotides and length and often span the translational start site of MOAT encoding mRNA molecules.

It will be appreciated by persons skilled in the art that variants of these sequences exist in the human population, and must be taken into account when designing and/or utilizing oligos of the invention. Accordingly, it is within the scope of the present invention to encompass such variants, with respect to the MOAT sequences disclosed herein or the oligos targeted to specific locations on the respective genes or RNA transcripts. With respect to the inclusion of such variants, the term "natural allelic variants" is used herein to refer to various specific nucleotide sequences and variants thereof that would occur in a human population. The usage of different wobble codons and genetic polymorphisms which give rise to conservative or neutral amino acid substitutions in the encoded protein are examples of such variants. Additionally, the term "substantially complementary" refers to oligo sequences that may not be perfectly matched to a target sequence, but the mismatches do not materially affect the ability of the oligo to hybridize with its target sequence under the conditions described.

B. Proteins

Full-length MOAT-B, MOAT-C, MOAT-D and MOAT-E proteins of the present invention may be prepared in a variety of ways, according to known methods. The proteins may be purified from appropriate sources, e.g., transformed bacterial or animal cultured cells or tissues, by immunoaffinity purification. However, this is not a preferred method due to the low amount of protein likely to be present in a given cell type at any time. The availability of nucleic acid molecules encoding MOAT proteins enables production of the proteins using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or Gibco-BRL, Gaithersburg, Md.

Alternatively, according to a preferred embodiment, larger quantities of MOAT proteins may be produced by expression in a suitable prokaryotic or eukaryotic system. For example, part or all of a DNA molecule, such as a cDNA having Sequence I.D. No. 1, 3, 5 or 7 may be inserted into a plasmid vector adapted for expression in a bacterial cell, such as E. coli. Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences.

The human MOAT proteins produced by gene expression in a recombinant procaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemagglutinin epitope. Such methods are commonly used by skilled practitioners.

The human MOAT proteins of the invention, prepared by the aforementioned methods, may be analyzed according to standard procedures. For example, such proteins may be subjected to amino acid sequence analysis, according to known methods.

The present invention also provides antibodies capable of immunospecifically binding to proteins of the invention. Polyclonal antibodies directed toward human MOAT proteins may be prepared according to standard methods. In a preferred embodiment, monoclonal antibodies are prepared, which react immunospecifically with the various epitopes of the MOAT proteins described herein. Monoclonal antibodies may be prepared according to general methods of Kohler and Milstein, following standard protocols. Polyclonal or monoclonal antibodies that immunospecifically interact with MOAT proteins can be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules. Other uses of anti-MOAT antibodies are described below.

II. Uses of MOAT-Encoding Nucleic Acids, MOAT Proteins and Antibodies Thereto

Cellular transporter molecules have received a great deal of attention as potential targets of chemotherapeutic agents designed to effectively block the export of pharmacological reagents from tumor cells. The MOAT proteins of the invention play a pivotal role in the transport of molecules across the cell membrane.

Additionally, MOAT nucleic acids, proteins and antibodies thereto, according to this invention, may be used as research tools to identify other proteins that are intimately involved in the transport of molecules into and out of cells. Biochemical elucidation of molecular mechanisms which govern such transport will facilitate the development of novel anti-transport agents that may sensitize tumor cells to conventional chemotherapeutic agents.

A. MOAT-Encoding Nucleic Acids

MOAT-encoding nucleic acids may be used for a variety of purposes in accordance with the present invention. MOAT-encoding DNA, RNA, or fragments thereof may be used as probes to detect the presence of and/or expression of genes encoding MOAT proteins. Methods in which MOAT-encoding nucleic acids may be utilized as probes for such assays include, but are not limited to: (1) in situ hybridization; (2) Southern hybridization (3) northern hybridization; and (4) assorted amplification reactions such as polymerase chain reactions (PCR).

The MOAT-encoding nucleic acids of the invention may also be utilized as probes to identify related genes from other animal species. As is well known in the art, hybridization stringencies may be adjusted to allow hybridization of nucleic acid probes with complementary sequences of varying degrees of homology. Thus, MOAT-encoding nucleic acids may be used to advantage to identify and characterize other genes of varying degrees of relation to the MOAT genes of the invention. Such information enables further characterization of transporter molecules which give rise to the chemoresistant phenotype of certain tumors. Additionally, they may be used to identify genes encoding proteins that interact with MOAT proteins (e.g., by the "interaction trap" technique), which should further accelerate identification of the components involved in the acquisition of drug resistance. The MOAT encoding nucleic acids may also be used to generate primer sets suitable for PCR amplification of target MOAT DNA. Criteria for selecting suitable primers are well known to those of ordinary skill in the art.

Nucleic acid molecules, or fragments thereof, encoding MOAT genes may also be utilized to control the production of MOAT proteins, thereby regulating the amount of protein available to participate in cytotoxic drug efflux. As mentioned above, antisense oligonucleotides corresponding to essential processing sites in MOAT-encoding mRNA molecules may be utilized to inhibit MOAT protein production in targeted cells. Alterations in the physiological amount of MOAT proteins may dramatically affect the ability of these proteins to transport pharmacological reagents out of the cell.

Host cells comprising at least one MOAT encoding DNA molecule are encompassed in the present invention. Host cells contemplated for use in the present invention include but are not limited to bacterial cells, fungal cells, insect cells, mammalian cells, and plant cells. The MOAT encoding DNA molecules may introduced singly into such host cells or in combination to assess the phenotype of cells conferred by such expression. Methods for introducing DNA molecules are also well known to those of ordinary skill in the art. Such methods are set forth in Ausubel et al. eds., *Current Protocols in Molecular Biology*, John Wiley & Sons, NY, N.Y. 1995, the disclosure of which is incorporated by reference herein.

The availability of MOAT encoding nucleic acids enables the production of strains of laboratory mice carrying part or all of the MOAT genes or mutated sequences thereof. Such mice may provide an in vivo model for development of novel chemotherapeutic agents. Alternatively, the MOAT nucleic acid sequence information provided herein enables the production of knockout mice in which the endogenous genes encoding MOAT-B, MOAT-C, MOAT-D or MOAT-E have been specifically inactivated. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo.

The alterations to the MOAT gene envisioned herein include modifications, deletions, and substitutions. Modifications and deletions render the naturally occurring gene nonfunctional, producing a "knock out" animal. Substitutions of the naturally occurring gene for a gene from a second species results in an animal which produces an MOAT gene from the second species. Substitution of the naturally occurring gene for a gene having a mutation results in an animal with a mutated MOAT protein. A transgenic mouse carrying the human MOAT gene is generated by direct replacement of the mouse MOAT gene with the human gene. These transgenic animals are valuable for use in vivo assays for elucidation of other medical disorders associated with cellular activities modulated by MOAT genes. A transgenic animal carrying a "knock out" of a MOAT encoding nucleic acid is useful for the establishment of a nonhuman model for chemotherapy resistance involving MOAT regulation.

As a means to define the role that MOAT plays in mammalian systems, mice can be generated that cannot make MOAT proteins because of a targeted mutational disruption of a MOAT gene.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring in fact, possess some or all of that alteration or genetic information, then they, too, are transgenic animals.

The alteration or genetic information may be foreign to the species of animal to which the recipient belongs, or foreign only to the particular individual recipient, or may be genetic information already possessed by the recipient. In the last case, the altered or introduced gene may be expressed differently than the native gene. The altered MOAT gene generally should not fully encode the same MOAT protein native to the host animal and its expression product should be altered to a minor or great degree, or absent altogether. However, it is conceivable that a more modestly modified MOAT gene will fall within the compass of the present invention if it is a specific alteration.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro. Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated MOAT genes to selectively inactivate the wild-type gene in totipotent ES cells (such as those described above) and then generate transgenic mice. The use of gene-targeted ES cells in the generation of gene-targeted transgenic mice is known in the art.

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$-fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabinofluranosyl)-5-iodouracil, (FIAU). By this counter selection, the number of homologous recombinants in the surviving transformants can be increased.

As used herein, a "targeted gene" or "knock-out" is a DNA sequence introduced into the germline or a non-human animal by way of human intervention, including but not limited to, the methods described herein. The targeted genes of the invention include DNA sequences which are designed to specifically alter cognate endogenous alleles.

Methods of use for the transgenic mice of the invention are also provided herein. Knockout mice of the invention can be injected with tumor cells or treated with carcinogens to generate carcinomas. Such mice provide a biological system for assessing chemotherapy resistance as modulated by a MOAT gene of the invention. Accordingly, therapeutic agents which inhibit the action of these transporters and thereby prevent efflux of beneficial chemotherapeutic agents from tumor cells may be screened in studies using MOAT knock out mice.

As described above, MOAT-encoding nucleic acids are also used to advantage to produce large quantities of substantially pure MOAT proteins, or selected portions thereof.

B. MOAT Proteins and Antibodies

Purified full length MOAT proteins, or fragments thereof, may be used to produce polyclonal or monoclonal antibodies which also may serve as sensitive detection reagents for the presence and accumulation of MOAT proteins (or complexes containing MOAT proteins) in mammalian cells. Recombinant techniques enable expression of fusion proteins containing part or all of MOAT proteins. The full length proteins or fragments of the proteins may be used to advantage to generate an array of monoclonal antibodies specific for various epitopes of MOAT proteins, thereby providing even greater sensitivity for detection of MOAT proteins in cells.

Polyclonal or monoclonal antibodies immunologically specific for MOAT proteins may be used in a variety of assays designed to detect and quantitate the proteins. Such assays include, but are not limited to: (1) flow cytometric analysis; (2) immunochemical localization of MOAT proteins in tumor cells; and (3) immunoblot analysis (e.g., dot blot, Western blot) of extracts from various cells. Additionally, as described above, anti-MOAT antibodies can be used for purification of MOAT proteins and any associated subunits (e.g., affinity column purification, immunoprecipitation).

From the foregoing discussion, it can be seen that MOAT-encoding nucleic acids, MOAT expressing vectors, MOAT proteins and anti-MOAT antibodies of the invention can be used to detect MOAT gene expression and alter MOAT protein accumulation for purposes of assessing the genetic and protein interactions involved in the development of drug resistance in tumor cells.

C. Methods and Kits Employing the Compositions of the Present Invention

From the foregoing discussion, it can be seen that MOAT-encoding nucleic acids, MOAT-expressing vectors, MOAT proteins and anti-MOAT antibodies of the invention can be used to detect MOAT gene expression and alter MOAT protein accumulation for purposes of assessing the genetic and protein interactions giving rise to chemotherapy resistance in tumor cells.

Exemplary approaches for detecting MOAT nucleic acid or polypeptides/proteins include:

a) comparing the sequence of nucleic acid in the sample with the MOAT nucleic acid sequence to determine whether the sample from the patient contains mutations;or b) determining the presence, in a sample from a patient, of the polypeptide encoded by the MOAT gene and, if present, determining whether the polypeptide is full length, and/or is mutated, and/or is expressed at the normal level; or c) using DNA restriction mapping to compare the restriction pattern produced when a restriction enzyme cuts a sample of nucleic acid from the patient with the restriction pattern obtained from normal MOAT gene or from known mutations thereof; or, d) using a specific binding member capable of binding to a MOAT nucleic acid sequence (either normal sequence or known mutated sequence), the specific binding member comprising nucleic acid hybridizable with the MOAT sequence, or substances comprising an antibody domain with specificity for a native or mutated MOAT nucleic acid sequence or the polypeptide encoded by it, the specific binding member being labelled so that binding of the specific binding member to its binding partner is detectable; or, e) using PCR involving one or more primers based on normal or mutated MOAT gene sequence to screen for normal or mutant MOAT gene in a sample from a patient.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples and they do not need to be listed here. Further, the term "specific binding pair" is also applicable where either or both of the specific binding member and the binding partner comprise a part of a large molecule. In embodiments in which the specific binding pair are nucleic acid sequences, they will be of a length to hybridize to each other under conditions of the assay, preferably greater than 10 nucleotides long, more preferably greater than 15 or 20 nucleotides long.

In most embodiments for screening for alleles giving rise to chemotherapy resistance, the MOAT nucleic acid in biological sample will initially be amplified, e.g. using PCR, to increase the amount of the analyte as compared to other sequences present in the sample. This allows the target sequences to be detected with a high degree of sensitivity if they are present in the sample. This initial step may be avoided by using highly sensitive array techniques that are becoming increasingly important in the art.

The identification of the MOAT gene and its association with a particular chemotherapy resistance paves the way for aspects of the present invention to provide the use of materials and methods, such as are disclosed and discussed above, for establishing the presence or absence in a test sample of a variant form of the gene, in particular an allele or variant specifically associated with chemotherapy resistance. This may be done to assess the propensity of the tumor to exhibit chemotherapy resistance.

In still further embodiments, the present invention concerns immunodetection methods for binding, purifying, removing, quantifying or otherwise generally detecting biological components. The encoded proteins or peptides of the present invention may be employed to detect antibodies having reactivity therewith, or, alternatively, antibodies prepared in accordance with the present invention, may be employed to detect the encoded proteins or peptides. The steps of various useful immunodetection methods have been described in the scientific literature, such as, e.g., Nakamura et al. (1987).

In general, the immunobinding methods include obtaining a sample suspected of containing a protein, peptide or antibody, and contacting the sample with an antibody or protein or peptide in accordance with the present invention, as the case may be, under conditions effective to allow the formation of immunocomplexes.

The immunobinding methods include methods for detecting or quantifying the amount of a reactive component in a sample, which methods require the detection or quantitation of any immune complexes formed during the binding process. Here, one would obtain a sample suspected of containing a MOAT gene encoded protein, peptide or a corresponding antibody, and contact the sample with an antibody or encoded protein or peptide, as the case may be, and then detect or quantify the amount of immune complexes formed under the specific conditions.

In terms of antigen detection, the biological sample analyzed may be any sample that is suspected of containing the MOAT antigen, such as a tumor tissue section or specimen, a homogenized tissue extract, an isolated cell, a cell membrane preparation, separated or purified forms of any of the above protein-containing compositions.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i.e., to bind to, any antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

In one broad aspect, the present invention encompasses kits for use in detecting expression of MOAT encoding nucleic acids in biological samples, including biopsy samples. Such a kit may comprise one or more pairs of primers for amplifying nucleic acids corresponding to the MOAT gene. The kit may further comprise samples of total mRNA derived from tissues expressing at least one or a subset of the MOAT genes of the invention, to be used as controls. The kit may also comprise buffers, nucleotide bases, and other compositions to be used in hybridization and/or amplification reactions. Each solution or composition may be contained in a vial or bottle and all vials held in close confinement in a box for commercial sale. In a further embodiment, the invention encompasses a kit for use in detecting MOAT proteins in chemotherapy resistant cancer cells comprising antibodies specific for MOAT proteins encoded by the MOAT nucleic acids of the present invention.

Another aspect of the present invention comprises screening methods employing host cells expressing one or more MOAT genes of the invention. An advantage of having discovered the complete coding sequenced of MOAT B-E is that cell lines that overexpress MOATB C D or E can be generated using standard transfection protocols. Cells that overexpress the complete cDNA will also harbor the complete proteins, a feature that is essential for biological activity of proteins. The overexpressing cell lines will be useful in several ways: 1)The drug sensitivity of overexpressing cell lines can be tested with a variety of known anticancer agents in order to determine the spectrum of anticancer agents for which the transporter confers resistance; 2)The drug sensitivity of overexpressing cell lines can be used to determine whether newly discovered anticancer agents are transported out of the cell by one of the discovered transporters; 3)Overexpressing cell lines can be used to identify potential inhibitors that reduce the activity of the transporters. Such inhibitors are of great clinical interest in that they may enhance the activity of known anticancer agents, thereby increasing their effectiveness. Reduced activity will be detected by restoration of anticancer drug sensitivity, or by reduction of transporter mediated cellular efflux of anticancer agents. In vitro biochemical studies designed to identify reduced transporter activity in the presence of potential inhibitors can also be performed using membranes prepared from overexpessing cell lines; and 4)Overexpressing cell lines can also be used to determine whether pharmaceutical agents that are not anticancer agents are transported out of the cell by the transporters.

The following protocols are provided to facilitate the practice of the present invention.

Isolation of MOAT-B cDNA

Forward {CT(A/G/T) GT(A/G/T) GC(A/G/T) GT(A/G/T) GT(A/G/T) GG(A/G/C/T)} and reverse {(G/A)CT (A/G/C/T)A(A/G/C (A/G/C/T)GC (A/G/C/T) (G/C) (T/A) (A/G/C/T)A(A/G) (A/G/C/T)GG (A/G/C/T)TC (A/G)TC} degenerate oligonucleotide primers were designed based upon the first nucleotide binding folds of human MRP, CFTR, and MDR1. Bacteriophage DNA isolated from a C200 cDNA library prepared in the λpCEV27 phagemid vector (17) was used as template in PCR reactions containing 250 ng cDNA, 5 µM primers, 50 mM KCl, 10 mM Tris-HCl, pH 8.3, 3 mM $MgCl_2$, 0.05% gelatin, 0.2 mM dNTP and Taq polymerase (Perkin Elmer Cetus). Five cycles of PCR were performed as follows: 94° C. for 1 minute, 40° C. for 2 minutes, 72° C. for 3 minutes. Twenty five cycles were then performed as follows: 94° C. for 1 minute, 55° C. for 1 minute, and 72° C. for 1 minute. The resulting reaction products were used as template in a second round of PCR, as described above, with nested forward {CGGGATCC AG(A/G) GA(A/G) AA(C/T) AT(A/C/T) CT(A/G/C/T) TTT GG(A/G/C/T)} and reverse {CGGAATTC (A/G/T/C)TC (A/G)TC (A/C/T)AG (A/G/C/T)AG (A/G)TA (A/T/G)AT (A/G)TC} degenerate oligonucleotide primers. PCR reaction products were isolated from an agarose gel and subcloned into the BamHI and EcoRI sites of pBluescript (Stratagene). Nucleotide sequence analysis was performed on plasmid DNA prepared from ampicillin resistant transformants. Additional cDNA clones were isolated from C200 (ovary) and B5 (breast) cDNA libraries by plaque hybridization using the PCR product as the initial radiolabeled probe.

RNA Blot Analysis

Blots containing polyA+ RNA isolated from human tissues (Clontech) were prehybridized at 45° C. for 8 hours in 50% formamide, 4×SSC, 4× Denhardt's solution, 0.04 M sodium phosphate monobasic, pH 6.5, 0.8% (w/v) glycine, 0.1 mg/ml sheared denatured salmon sperm DNA. Hybridization was performed at 45° C. with $^{32}$P-labeled MOAT-B or GAPDH probes in a solution containing 50% formamide, 3×SSC, 0.04 M sodium phosphate pH 6.5, 10% dextran sulfate, 0.1 mg/ml sheared denatured salmon sperm DNA. Blots were washed 2 times for 15 min at 65° C. in 2×SSC, 5 mM Tris-HCl pH7.4, 0.5% SDS, 2.5 mM EDTA, 0.1% sodium pyrophosphate pH 8.0, and subsequently washed 2 times for 15 min in 0.1×SSC. Blots were then subjected to autoradiography.

Chromosomal localization

Preparation of metaphase spreads from phytohemagglutinin-stimulated lymphocytes of a healthy female donor, and fluorescence in situ hybridization and detection of immunofluorescence were carried out as previously described (18). A 2.2-kb cDNA clone of MOAT-B inserted in pBluescript was biotinylated by nick translation in a reaction containing 1 μg DNA, 20 μM each of dATP, dCTP and dGTP, 1 μM dTTP, 25 mM Tris-HCl, pH 7.5, 5 mM MgCl$_2$, 10 mM β-mercaptoethanol, 10 μM biotin-16-dUTP (Boehringer Mannheim), 2 units DNA polymerase 1/DNase 1 (GIBCO, BRL) and water to a total volume of 50 μl. The probe was denatured and hybridized to metaphase spreads overnight at 37° C. Hybridization sites were detected with fluorescein-labeled avidin (Oncor) and amplified by addition of anti-avidin antibody (Oncor) and a second layer of fluorescein-labeled avidin. The chromosome preparations were counterstained with DAPI and observed with a Zeiss Axiophot epifluorescence microscope equipped with a cooled charge coupled device camera (Photometrics, Tucson AZ) operated by a Macintosh computer work station. Digitized images of DAPI staining and fluorescein signals were captured, pseudo-colored and merged using Oncor Image version 1.6 software.

Isolation of MOAT-C and MOAT-D cDNA

MOAT-C and MOAT-D cDNA clones were isolated by plaque hybridization from bacteriophage cDNA libraries using the I.M.A.G.E. clones as the initial probes (ATCC).

RNA Blot Analysis

Blots containing polyA$^+$ RNA isolated from human tissues (Clontech) were purchased from Clontech, and hybridized with radiolabeled MOAT-C, MOAT-D or actin probes according to the manufacturer's directions.

Chromosomal Localization

Preparation of metaphase spreads from phytohemagglutinin-stimulated lymphocytes of a healthy female donor, and fluorescence in situ hybridization and detection of immunofluorescence were carried out as previously described (18). A MOAT-C probe inserted in pBluescript, or MOAT-D probe inserted in pBluescript, was biotinylated by nick translation in a reaction containing 1 μg DNA, 20 μM each of dATP, dCTP and dGTP, 1 μM dTTP, 25 mM Tris-HCl, pH 7.5, 5 mM MgCl$_2$, 10 mM β-mercaptoethanol, 10 μM biotin-16-dUTP (Boehringer Mannheim), 2 units DNA polymerase 1/DNase 1 (GIBCO, BRL) and water to a total volume of 50 μl. The probe was denatured and hybridized to metaphase spreads overnight at 37° C. Hybridization sites were detected with fluorescein-labeled avidin (Oncor) and amplified by addition of anti-avidin antibody (Oncor) and a second layer of fluorescein-labeled avidin. The chromosome preparations were counterstained with DAPI and observed with a Zeiss Axiophot epifluorescence microscope equipped with a cooled charge coupled device camera (Photometrics, Tucson AZ) operated by a Macintosh computer work station. Digitized images of DAPI staining and fluorescein signals were captured, pseudo-colored and merged using Oncor Image version 1.6 software.

The following examples are provided to illustrate various embodiments of the invention. They are not intended to limit the invention in any way.

EXAMPLE I

Isolation of MOAT-B cDNA

A degenerate PCR approach was used to isolate MRP-related transporters. Degenerate oligonucleotide primers were prepared based upon the N-terminal nucleotide binding folds of MRP and other eukaryotic transporters, and used in conjunction with DNA prepared from an ovarian cancer cell line bacteriophage library. Nucleotide sequence analysis of one of the resulting PCR products indicated that it encoded a segment of a novel nucleotide binding fold that was most closely related to MRP and cMOAT. Overlapping cDNA clones were isolated from ovarian and breast bacteriophage libraries by plaque hybridization using the PCR product as the initial probe. A total of 5.9 kB of cDNA was isolated. Nucleotide sequence analysis revealed two classes of cDNA clones that were about equally represented among isolates from each of the two bacteriophage libraries. The first class contained an open reading frame of 3975 bp that was bordered by in frame stop codons located at positions-76 and-42 (relative to the putative initiation codon) and 3976, and encoding a predicted protein of 1325 amino acids, which is designated MOAT-B. The open reading frame was followed by approximately 2 kB of 3" untranslated sequences. The most upstream ATG in the open reading frame was located in the sequence context $^{-4}$CAAGATGC$^{+4}$. The A at position −3 of the putative translation initiation codon was in agreement with the major feature of the Kozak consensus sequence, but the C at position +4 was divergent from the more usual G. The second class of cDNA clones was identical to the first with the exception of a single nucleotide. These clones harbored an additional T following nucleotide 3872 of the first class of clones, close to the C-terminus of the predicted protein. This additional nucleotide resulted in a frame shift such that the predicted protein of the second class of cDNA clones was 22 residues shorter than that of the first class of cDNA clones, and in which the C-terminal 34 residues of the latter reading frame were replaced by 12 distinct residues. See brief description of FIGS. 1A and 1B.

Analysis of the MOAT-B Predicted Structure.

Comparison of the MOAT-B predicted protein with complete coding sequences in protein data bases using the BLAST program indicated that it shared significant similarity with several eukaryotic ABC transporters. Table I.

TABLE I

Comparison of peptide domains of MOAT-B with those of other eukaryotic ABC transporters

| | MOAT-B Domain (peptide) | | | | | | |
|---|---|---|---|---|---|---|---|
| | TM1 (88–376) | NBF1 (428–576) | linker region (577–705) | TM2 (706–992) | NBF2 (1058–1216) | C-terminus (1217–1325) | overall identity |
| | | | percent identity | | | | |
| MRP human | 28.6 | 55.6 | 27.9 | 33.3 | 61.6 | 51.6 | 39.2 |
| YCF1 yeast | 27 | 56 | 27.9 | 34 | 57.2 | 48.5 | 38.9 |
| MOAT human | 33.2 | 53.3 | 32.8 | 31.4 | 55.3 | 44.9 | 38 |

TABLE I-continued

Comparison of peptide domains of MOAT-B with those of other eukaryotic ABC transporters

| | MOAT-B Domain (peptide) | | | | | | |
|---|---|---|---|---|---|---|---|
| | TM1 (88–376) | NBF1 (428–576) | linker region (577–705) | TM2 (706–992) | NBF2 (1058–1216) | C-terminus (1217–1325) | overall identity |
| | | | | percent identity | | | |
| CFTR Human | 30.5 | 48 | 27.9 | 37.7 | 44 | 21 | 36.3 |
| SUR rat | 28.1 | 41.3 | 28.2 | 30 | 52.8 | 42.8 | 32.9 |
| MDR1 human | 17.6 | 39.2 | 21.1 | 17.3 | 32.2 | 40.3 | 23.3 |

B The indicated domains are,
TM1: segment containing the transmembrane spanning domain N-terminal to NBF1;
NBF1 and NBF2: nucleotide binding folds 1 and 2;
Linker region: segment located between NBF1 and TM2;
TM2: segment containing the transmembrane spanning domain located between the two NBFs;
C-terminus: segment between NBF2 and the C-terminus of the proteins.
Sequence alignments were generated using the PILEUP program of the GCC package. Percent amino acid identity with MOAT-B domains are shown.

Typical features of eukaryotic ABC transporters were present in the predicted MOAT-B protein. See FIGS. 1A and 1B. Overall the protein was composed of a tandem repeat of a nucleotide binding fold appended C-terminal to a hydrophobic domain that contained several potential transmembrane spanning helices. Conserved Walker A and B ATP binding sites were present in each of the nucleotide binding folds. See FIG. 2A. In addition, a conserved C motif, the signature sequence of ABC transporters, was present in each nucleotide binding fold. Analysis of potential transmembrane motifs using the TMAP program (19) and an input sequence alignment of MOAT-B and MOAT-C, a transporter highly related to MOAT-B4, predicted 12 transmembrane helices with 6 transmembrane segments in each of the two hydrophobic domains. This 6+6 configuration of predicted transmembrane helices is in agreement with topological models proposed for MRP and other ABC transporters (20,21), and is shown in FIGS. 1A and 1B. However, alternative predictions of transmembrane segments were obtained using different program parameters or input sequence alignments. For example, when the TMAP program was used with an input sequence alignment consisting of human MRP, rat cMOAT, rat sulfonyl urea receptor (SUR), human cystic fibrosis conductance regulator (CFTR) and human P-glycoprotein, a 6+5 configuration was predicted. The only substantial difference between the latter prediction and the structure shown in FIGS. 1A and 1B is that transmembrane segments 9 (829-853) and 10 (855-878) were replaced by a single predicted transmembrane segment spanning amino acids 847-875.

Among ABC transporters, the degree of similarity of the nucleotide binding folds is considered to be the best indicator of functional conservation. Comparison of the nucleotide binding folds of MOAT-B with other eukaryotic ABC transporters indicated that it was most closely related to MRP, the yeast cadmium resistance protein (YCF1) and cMOAT (Table I), three transporters that have organic anions as substrates. The MOAT-B NBF1 was 55.6, 56.0 and 53.3 percent identical, and the MOAT-B NBF2 was 61.6, 57.2 and 55.3 percent identical to the first and second nucleotide binding folds of human MRP, YCF1 and human cMOAT, respectively. Aside from the latter transporters, the MOAT-B nucleotide binding folds were most closely related to those of CFTR and SUR. The MOAT-B nucleotide binding folds shared significantly less similarity with those of MDR1. Alignment of the MOAT-B nucleotide binding folds with those of other eukaryotic transporters is shown in FIG. 2A. Analysis of the overall amino acid identity of MOAT-B with other ABC transporters also indicated that it was most closely related to MRP, YCF1 and cMOAT (Table I). Overall MOAT-B was 39.2, 38.9 and 38 percent identical to these transporters, respectively. FIG. 2B shows a comparison of the hydropathy profiles of MOAT-B with those of other eukaryotic transporters. This comparison reveals that MOAT-B (1325 amino acids) is approximately 200 amino acids smaller than MRP (1531 residues), cMOAT (1545 residues) and YCF1 (1515 residues), and that this size difference is largely accounted for by the absence in MOAT-B of an amino terminal hydrophobic extension that is present in MRP, cMOAT and YCF1 (22). This N-terminal hydrophobic segment is predicted to harbor several transmembrane spanning segments, and is also present in SUR.

Expression Pattern of MOAT-B in Human Tissues.

Figure 3:
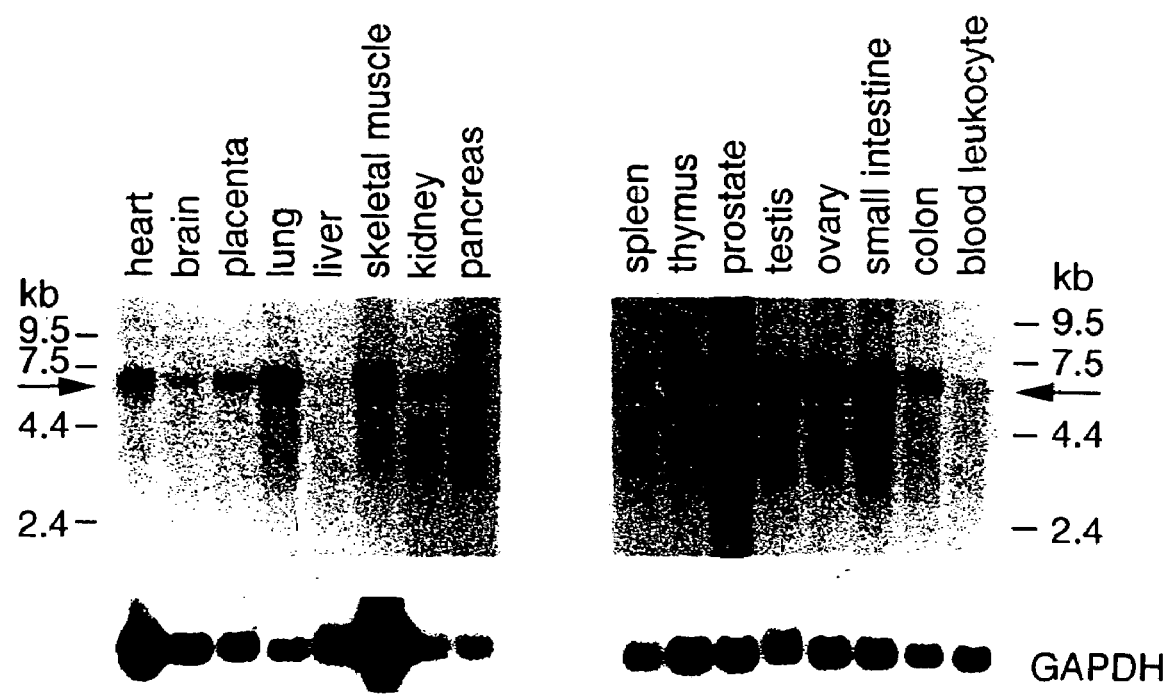
FIG. 3 is a Northern blot showing the tissue distribution of MOAT-B transcript. Membranes containing poly (A)+ RNA prepared from human tissues were hybridized with a radiolabeled MOAT-B or GAPDH probe. Top panels show MOAT-B transcript and bottom panels show the control GAPDH transcript. Arrows indicate the position of MOAT-B transcript. Prolonged exposure of the film revealed a low level signal in liver.

To gain insight into the possible function of MOAT-B, its expression pattern in a variety of human tissues was examined by RNA blot analysis. As shown in FIG. 3, a MOAT-B transcript of approximately 6 kB was readily detected. The isolation of 5.9 kB of MOAT-B cDNA was consistent with this size. MOAT-B expression was detected in each of the 16 tissues analyzed. Transcript levels were highest in prostate and lowest in liver and peripheral blood leukocytes, for which prolonged exposure of film were required to detect expression. Intermediate levels of expression were observed in other tissues.

Chromosomal Localization of the MOAT-B Gene.

Figure 4:
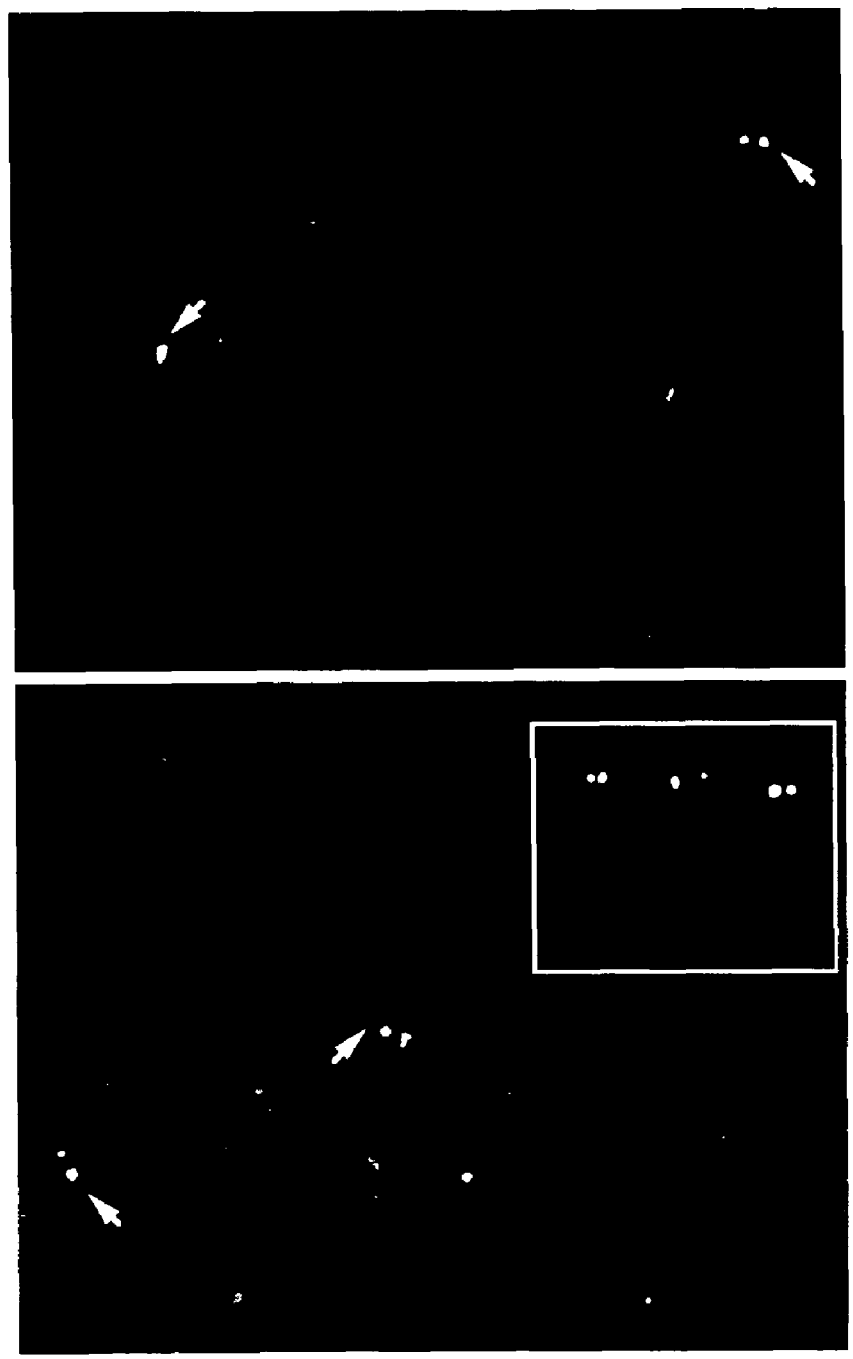
FIG. 4 shows the chromosomal localization of the gene encoding MOAT-B. Human metaphase spreads were hybridized with a biotin-labeled MOAT-B cDNA probe and detected by FITC-conjugated avidin. Hybridization signals at chromosome 13q32 in two metaphase spreads are indicated by arrows. The inset shows paired hybridization signals at band q32 of chromosome 13 from three other metaphase spreads.

The MOAT-B chromosomal localization was determined by fluorescence in situ hybridization. As shown in FIG. 4, hybridization of the MOAT-B probe to metaphase spreads revealed specific labeling at human chromosome band 13q32. Fluorescent signals were detected on chromosome 13 in each of 19 metaphase spreads scored. Of 135 signals observed, 62 (46%) were on 13q. Among these signals, 61 localized at 13q32, near the boundary between 13q31 and 13q32. Paired (on sister chromatids) signals were only seen at band 13q32. In several metaphases, signals on a single chromatid were observed at chromosome bands 6p21 or 4q21, suggesting hybridization to distantly related sequences.

EXAMPLE II

Isolation of MOAT-C and MOAT-D cDNA

Isolation of the MOAT-$B_4$ transporter as described above suggested the possibility that there were other MRP/cMOAT-related transporters. A blast search (36) of the nonredundent expressed sequence tag data base using MRP and related yeast transporters revealed two clones with significant similarity to MRP and cMOAT. The first of these sequences (I.M.A.G.E. consortium clone 113196) was 1.2 kb in length, 800 bp of which encoded an MRP-related peptide. A segment of this clone was used as a probe to screen ovarian and hematopoietic bacteriophage libraries. Analysis of these cDNA clones indicated that they contained approximately 2 kb of additional coding sequence not present in clone 113196. An additional 1655 bp of 5' sequence was obtained by several rounds of RACE using the bacteriophage DNA prepared from the ovarian cDNA library as template. The continuity of the sequences obtained by RACE with the cDNA clones isolated from bacteriophage libraries was confirmed by nucleotide sequence analysis of a 2 kb product obtained by RT/PCR using an upstream oligonucleotide primer located at the 5' end of the RACE sequence and a downstream primer located at the 5' end of the cDNA obtained by plaque hybridization. A total of approximately 5.9 kb of cDNA sequences were isolated. Nucleotide sequence analysis revealed an open reading frame of 4311 bp that was preceded by an in frame stop codon located at positions −93 (relative to the putative initiation codon), and encoding a predicted protein of 1437 amino acids, which is designated MOAT-C herein. The open reading frame was followed by approximately 1.4 kB of 3' untranslated sequences in which a polyadenylation sequence (AAUAAA) was located 20 bp upstream of the poly(A) tail. The most upstream ATG in the open reading frame was located in the sequence context $^{-4}$GAAGATGA$^{+4}$. The A at position −3 of the putative translation initiation codon was in agreement with the major feature of the Kozak consensus sequence, but the A at position +4 was divergent from the more usual G (37). The second sequence identified in our data base search (I.M.A.G.E. consortium clone 208097) was 1.2 kb in length, of which 588 bp encoded an MRP-related peptide. A segment of this clone was used as a probe to screen liver and monocyte bacteriophage cDNA libraries, and 5' cDNA segments of the isolated cDNA clones were used in a subsequent round of screening. Together approximately 5.2 kb of cDNA sequence were isolated. Nucleotide sequence analysis revealed an open reading frame of 4570 bp, which is designated MOAT-D herein. The open reading frame was followed by approximately 0.6 kb of 3' untranslated sequences in which a polyadenylation sequence (AAUAAA) was located 12 bp upstream of the poly(A) tail. An upstream in frame stop codon was not present in the MOAT-D cDNA clones, and attempts to obtain additional upstream sequences by RACE using as template cDNA prepared from sources in which MOAT-D is abundant were not successful. The most upstream ATG in the open reading frame (nucleotide position 5-7), located in the sequence context $^{-4}$ATGGATGG$^{+4}$, was therefore designated as the translational initiation site. The G at position +4, was in good agreement with the Kozak consensus sequence, but the T at −3 was divergent from the more usual A (37). Although an upstream in frame stop codon was not identified in the MOAT-D cDNA clones, the size of the encoded protein was within one amino acid of the size of the transporter with which it shares the highest degree of identity (MRP), suggesting that the complete MOAT-D open reading frame was present in the isolated cDNA clones.

Analysis of the MOAT-C and MOAT-D Predicted Proteins.

Figure 6B:
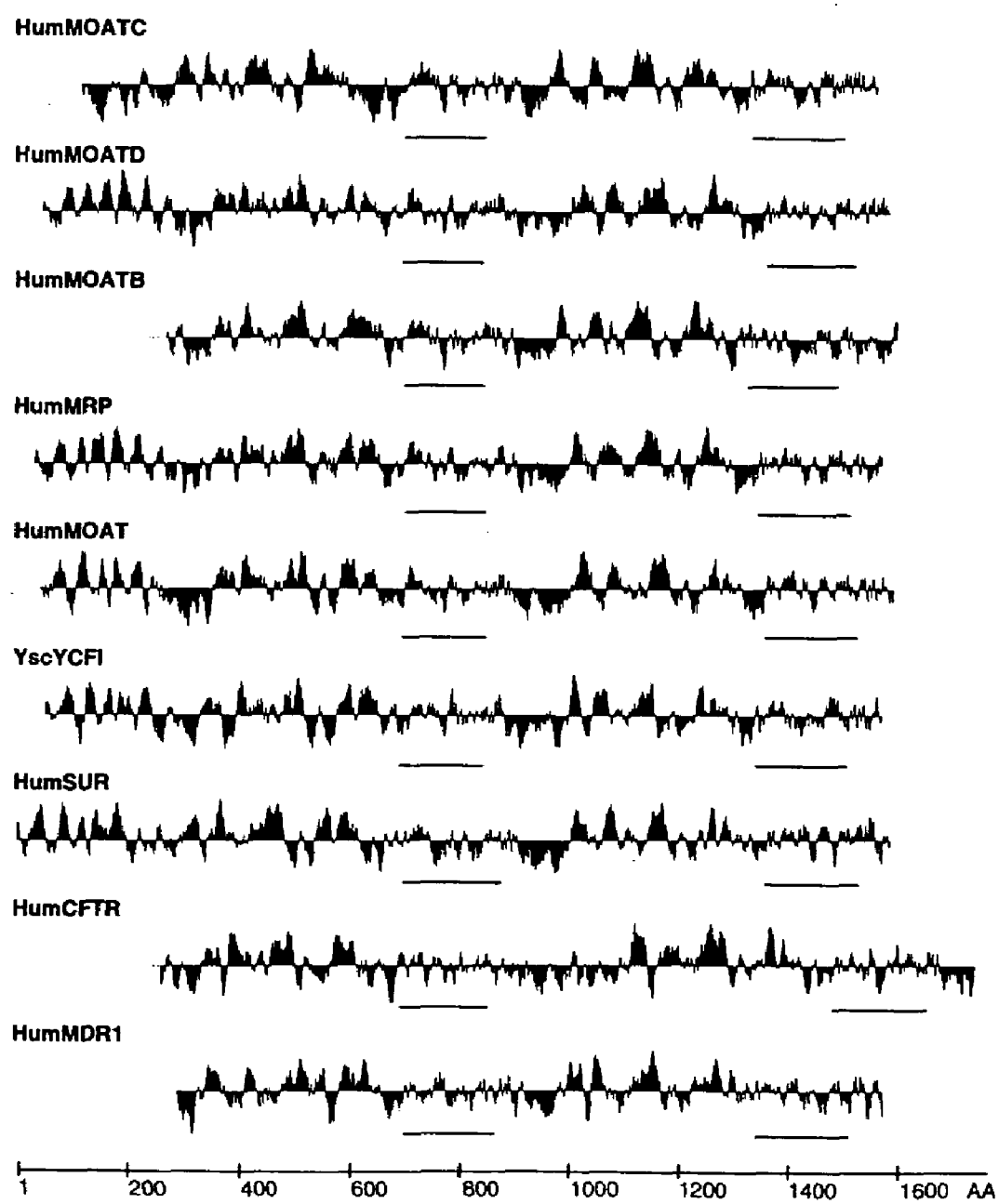

Comparison of the MOAT-C and MOAT-D predicted proteins with complete coding sequences in protein data bases using the BLAST program indicated that they shared significant similarity with several eukaryotic ABC transporters. Typical features of eukaryotic ABC transporters were present in the predicted proteins. See FIG. 5. Overall the proteins were composed of hydrophobic domains containing potential transmembrane spanning helices and two nucleotide binding folds. Conserved Walker A and B ATP binding sites, as well as a conserved C motif, the signature sequence of ABC transporters, was present in the nucleotide binding folds. Computer assisted analysis of potential transmembrane helices of MOAT-C using the TMAP program (19) predicted 12 transmembrane helices with 6 transmembrane spanning helices in each of two membrane spanning domains. This 6+6 (TM1-TM6 and TM7-TM12) configuration of predicted transmembrane helices is in agreement with topological models proposed for several other ABC transporters (20, 21), and is shown in FIG. 5. However, alternative predictions of transmembrane segments were obtained using different program parameters or input sequence alignments. Comparison of the hydropathy profiles of MOAT-C with other MRP/cMOAT-related transporters (FIG. 6B) indicates that its structure is similar to that of MOAT-B, which also has two membrane spanning domains.

In contrast to MOAT-C, hydrophobicity analysis of MOAT-D indicated that it has three membrane spanning domains. Similar to MRP, cMOAT and the yeast cadmium resistance factor 1 (YCF1), MOAT-D has an additional N-terminal hydrophobic domain that is not present in MOAT-B or MOAT-C (FIGS. 5 and 6). A 5+6+6 configuration of transmembrane spanning helices has been proposed for MRP (38), in which the N-terminal extension harbors 5 transmembrane spanning helices, and 6 transmembrane helices are present in the second and third membrane spanning domain. An alignment of the MOAT-D predicted protein with MRP using the GAP program indicated that proposed MRP transmembrane spanning helices were conserved in MOAT-D. This 5+6+6 model for MOAT-D is shown in FIG. 5. Another configuration of transmembrane spanning helices (5+6+4) was predicted using computer assisted analysis. MRP has been reported to have two N-linked glycosylation sites in its N-terminus (Asn-19 and Asn-23) and another site located between the first and second transmembrane spanning helix of its third membrane spanning domain (Asn-1006). The alignment of MOAT-D with MRP indicated that an N-terminal (Asn-21) and a distal N-glycosylation sites (Asn-1008/1009) were conserved in analogous positions in MOAT-D. Only the distal N-glycosylation site of MRP is conserved in MOAT-C (Asn890) (FIG. 5) and MOAT-B$^4$ (Asn746/754).

Among ABC transporters, the degree of similarity of the nucleotide binding folds is considered to be the best indicator of functional conservation. Comparison of the nucleotide binding folds of MOAT-C and MOAT-D with other eukaryotic ABC transporters indicated that they were most closely related to those of human MRP, human cMOAT and yeast YCF1, three transporters that have organic anions as substrates. As shown in Table 2, among the human transporters, the MOAT-C NBF1 was about equally related to MOAT-D, MRP and cMOAT (55-61% identity), and less similar to MOAT-B (49% identity).

TABLE II

Amino acid identity: nucleotide binding folds 1 and 2 of MRP/cMOAT sub-family members.

|        | MOAT-C     | MOAT-D    | MOAT-B    | MRP       | cMOAT     | YCF1      |
|--------|------------|-----------|-----------|-----------|-----------|-----------|
|        |            |           | % IDENTIFY (BNF1/NBF20) |  |  |  |
| MOAT-C | —          | 57.3/58.9 | 49.3/59.1 | 60.0/59.4 | 61.3/60.6 | 55.3/58/8 |
| MOAT-D | 57.3/58/9  | —         | 55.3/54.1 | 70.173.8  | 67.3/70.0 | 52.7/61.3 |
| MOAT-B | 49.3/59.1  | 55.3/54.1 | —         | 57.3/61/6 | 53.3/55.3 | 56.0/57.2 |
| MRP    | 60.0/59.4  | 70.7/73.7 | 57.3/61.6 | —         | 66.0/73.1 | 53.3/63.8 |
| cMOAT  | 61/3/60.6  | 67.3/70.0 | 53.3/55.3 | 66.0/73.1 | —         | 50.7/61/3 |
| YCF1   | 55.3/58.8  | 52.7/61.3 | 56.0/57.2 | 53.3/63.8 | 50.7/61.3 | —         |

The MOAT-C NBF2 shared about equal amino acid identity with the five other transporters in this group (59-61% identity). Overall, the MOAT-C protein was about equally related to the other five transporters in this group, with 33.1-36.5% identity. Aside from these transporters, MOAT-C is most closely related to CFTR, with which its NBFs shared 44%/42% identity, and SUR, with which its NBFs shared 49%/51% identity.

The MOAT-D NBFs were clearly most closely related to those of MRP and cMOAT, with which they shared considerable amino acid identity (67.3-73.8%). See Table III. Of the latter two transporters, the MOAT-D NBFs were slightly more related to those of MRP. In contrast, the MOAT-D NBFs shared only 55.3-58.9% identity with those of MOAT-C and MOAT-B. Overall, MOAT-D was again most closely related to MRP (57.3%) and cMOAT (46.9%), but significantly more related to MRP. Consistent with the analysis of NBFs, MOAT-D was much less related to MOAT-C and MOAT-B, with which it shared only 33.1% and 35.3% identity, respectively. Alignment of the MOAT-C and MOAT-D nucleotide binding folds with those of other eukaryotic transporters is shown in FIG. 6.

TABLE III

Overall amino acid identifying among MRP/cMOAT sub-family members

|        | MOAT-C | MOAT-D | MOAT-B | MRP  | cMOAT | YCF1 |
|--------|--------|--------|--------|------|-------|------|
|        |        |        | % identity |  |       |      |
| MOAT-C | —      | 33.1   | 36.5   | 35.8 | 36.2  | 33.6 |
| MOAT-D | 33.1   | —      | 35.3   | 57.3 | 46.9  | 38.1 |
| MOAT-B | 36.4   | 35.3   | —      | 39.4 | 36.8  | 38.8 |
| MRP    | 35.8   | 57.3   | 39.4   | —    | 48.4  | 46.4 |
| cMOAT  | 36.3   | 46.9   | 36.8   | 48.8 | —     | 38.8 |
| YCF1   | 33.6   | 38.1   | 38.8   | 40.4 | 38.8  | —    |

Expression Pattern of MOAT-C and MOAT-D in Human Tissues.

Figure 7:
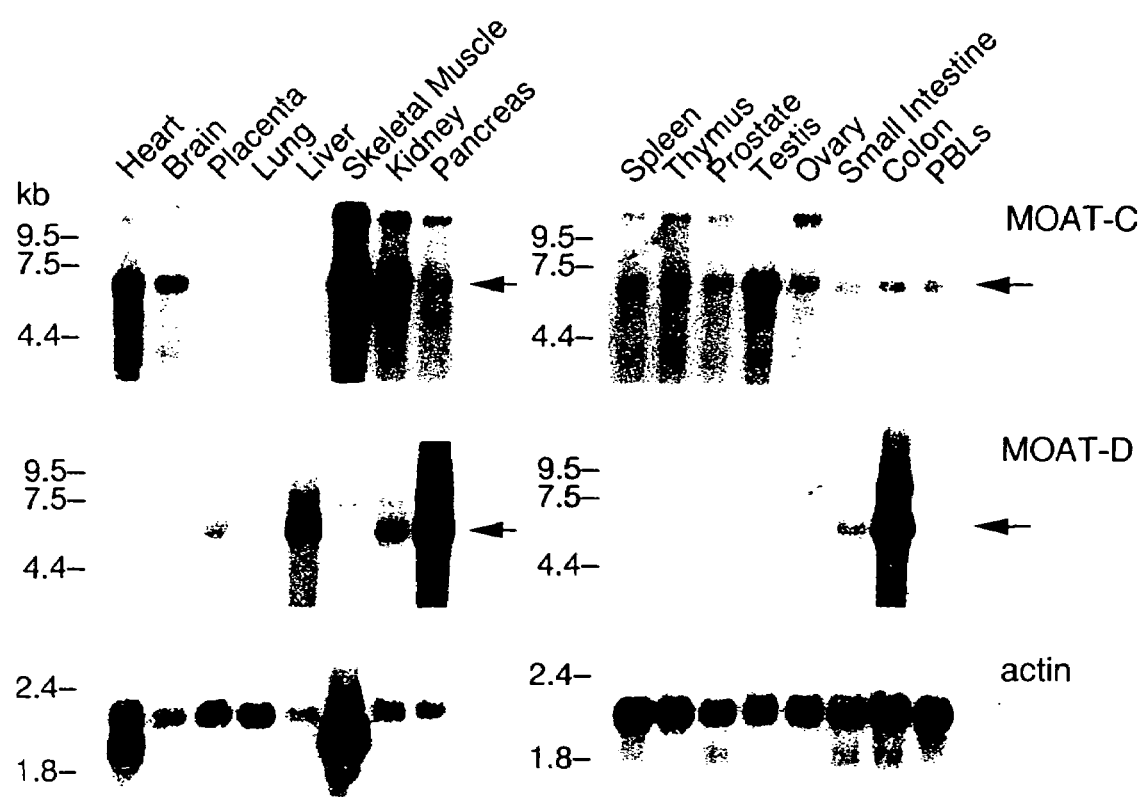
FIG. 7 is a Northern blot showing the tissue distribution of MOAT-C and MOAT-D transcripts. Blots containing poly A+RNA prepared from various human tissues were hybridized with MOAT-C, MOAT-D and actin probes. Arrows indicate the position of the MOAT-C (top panel) and MOAT-D (middle panel) transcripts. The bottom panel shows the control actin transcript.

To gain insight into the possible functions of MOAT-C and MOAT-D, their expression patterns in a variety of human tissues was examined by RNA blot analysis. As shown in FIG. 7 (upper panels), a MOAT-C transcript of approximately 6.6 kB was readily detected in several tissues. MOAT-C transcript levels were highest in skeletal muscle, with intermediate levels in kidney, testes, heart and brain. Low levels were detected in most other tissues, including spleen, thymus, prostate, ovary, and placenta. Prolonged exposures were required for detection in lung and liver. MOAT-D was expressed as an approximately 6 kb transcript (middle panels). Compared to MOAT-C, the MOAT-D expression pattern was more restricted. MOAT-D was highly expressed in colon and pancreas, with lower levels in liver and kidney. Low levels were detected in small intestine, placenta and prostate. Prolonged exposures were required to detect MOAT-D in testes, thymus, spleen and lung.

Chromosomal localization of the MOAT-C and MOAT-D genes.

Figure 8:
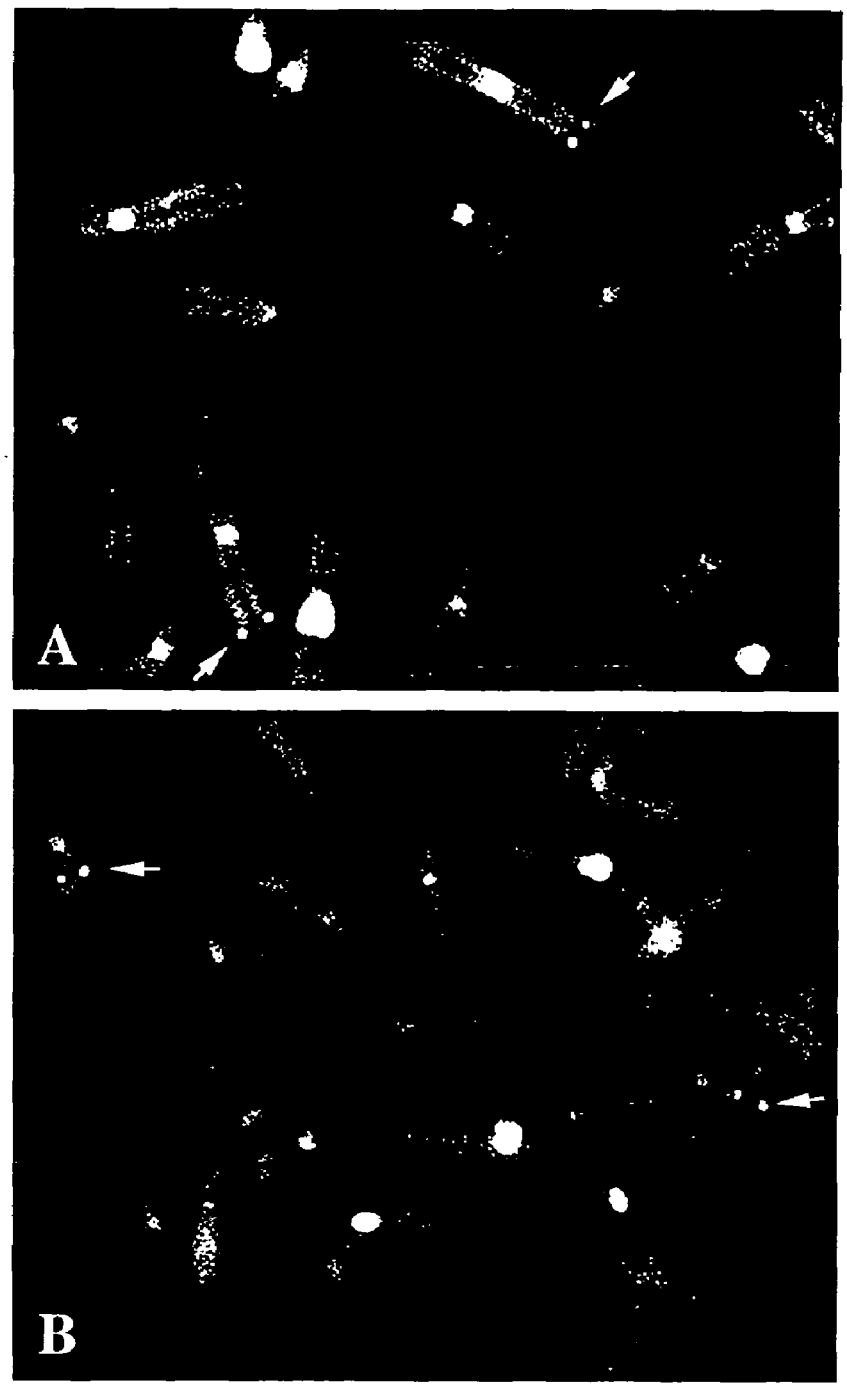
FIGS. 8A and 8B show the chromosomal localization of the MOAT-C and MOAT-D genes. Human metaphase spreads were hybridized with a biotin-labeled MOAT-C and MOAT-D cDNA probes and detected by FITC-conjugated avidin.

The MOAT-C and MOAT-D chromosomal localizations were determined by fluorescence in situ hybridization. As shown in FIG. 8, hybridization of the MOAT-C probe to metaphase spreads revealed specific labeling at human chromosome band 3q27. Fluorescent signals were detected on chromosome 3q in each of 22 metaphase spreads scored. Of 75 signals observed, 43 (57%) were on 3q. Paired (on sister chromatids) signals were only seen at band 3q27. Hybridization of the MOAT-D probe revealed specific labeling at human chromosome band 17q21.3. Fluorescent signals were detected on chromosome 17 in each of 21 metaphase spreads scored. Of 83 signals observed, 34 (41%) were on 17q21.3. Paired (on sister chromatids) signals were only seen at band 17q21.3.

EXAMPLE III

Isolation of MOAT-E and MOAT-E cDNA.

Analysis of ara, a reported cDNA sequence that encodes a 453 amino acid transporter, revealed that it is a non-physiological sequence representing a combination of 5' MRP sequences fused to an MRP/cMOAT-related transporter. The MRP sequences extend to codon 8 of the reported predicted protein.

To isolate the complete physiological cDNA, a RT/PCR approach was employed in which primers were designed based upon a reported genomic sequence that encodes exons identical to the reported ara sequence. The MOAT-E cDNA was isolated in three segments. The first segment, spanning residues 1-616, was isolated by PCR using 5' primer ATGGCCGCGCCTGCTGAGC; (SEQ ID NO: 10) and 3' primer GTCTACGACACCAGGGTCAA (SEQ ID NO: 11). The second segment, spanning residues 1815-3187, was isolated by PCR using 5' CTGCCTGGAAGAAGTTGACC (SEQ ID NO: 12) and 3' primer CTGGAATGTCCACGTCAACC (SEQ ID NO: 13). The third segment, spanning residues 3158-1503, was isolated by PCR using 5' primer GGAGACAGACACGGTTGACG (SEQ ID NO: 14) and 3' primer GCAGACCAGGCCTGACTCC (SEQ ID NO: 15). The primer were designed based upon the nucleotide sequence of human genomic BAC clone CIT987SD-962B4. The template for these reactions was random-primed human kidney cDNA prepared from total RNA. Using this approach the physiological cDNA was isolated which is designated MOAT-E herein and set forth as Sequence I.D. No. 7.

Analysis of the MOAT-E Predicted Protein.

MOAT-E encodes a 1503 amino acid transporter. The MOAT-E predicted amino acid sequence is designated Sequence I.D. No. 8. See FIG. 9. Also shown is the location of potential transmembrane helices (overbars), potential N-glycosylation site (black dot) and the two nucleotide binding folds (NBF1 and NBF2). Walker A and B motifs, as well as the signature C motif of ABC transporters are also indicated. Comparison of MOAT-E with ara indicates that the ara predicted protein is not only a fused sequence, but also that it represents only 446 (~30%) of the 1503 MOAT-E residues.

Comparison of MOAT-E with the other members of the MRP/cMOAT subfamily, which include MRP, cMOAT, MOAT-B, MOAT-C and MOAT-E, is shown in Table IV. MOAT-E is highly related to MOAT-D, MRP and cMOAT, with which it shares 39-45% identity. This high degree of identity is also indicated by the high percent identities of the nucleotide binding folds, which range from 55-61%. In contrast, MOAT-E is less related to MOAT-B and MOAT-C, with which it shares ~31% and 34% identity, respectively.

TABLE IV

Amino acid identity among MRP/cMOAT sub-family members.
[a]The bold type indicates the percent identity of the overall proteins, and the parentheses indicates the percent identity of the nucleotide binding folds.

|  | MOAT-E | MOAT-B | MOAT-C | MOAT-D | MRP | cMOAT |
|---|---|---|---|---|---|---|
|  |  |  | % identity[b] |  |  |  |
| MOAT-E | — | 33.9 | 30.6 | 43.6 | 45.1 | 38.9 |
|  | — | (52.0/56.6) | (50.0/52.5) | (59.3/59.4) | (61.3/61.4) | (55.3/59.4) |
| MOAT-B | 33.9 | — | 36.4 | 35.3 | 39.4 | 36.8 |
|  | (52.0/56.6) | — | (49.3/59.1) | (55.3/54.1) | (57.3/61.6) | (56.0/57 2) |
| MOAT-C | 30.0 | 36.4 | — | 33.1 | 35.8 | 36.2 |
|  | (50.0/52.5) | (49.3/59.1) | — | (57.3/58.9) | (60.6/59.4) | (61.3/60.6) |
| MOAT-D | 43.6 | 35.3 | 33.1 | — | 57.3 | 46.9 |
|  | (59.3/59.4) | (55.3/54.1) | (57.3/58.9) | — | (70 7/73.8) | (67.3/70.0) |
| MRP | 45.1 | 39.4 | 35.8 | 57.3 | — | 48.4 |
|  | (61.3/61.9) | (57.3/61.6) | (60.0/59.4) | (70.7/73.8) | — | (66.0/73 1) |
| cMOAT | 38.9 | 36.8 | 36.2 | 46.9 | 48.4 | — |
|  | (53.1/59.4) | (56.0/57.2) | (61.3/60.6) | (67.3/70.0) | (66.0/73.1) | — |

[a]overall amino acid identifies are indicated in bold-face, and identities of nucleotide binding folds 1 and 2 are indicated in parentheses (NBF1/NBF2).
[b]percent identity was obtained using the GAP command in the GCG package.

Figure 10:
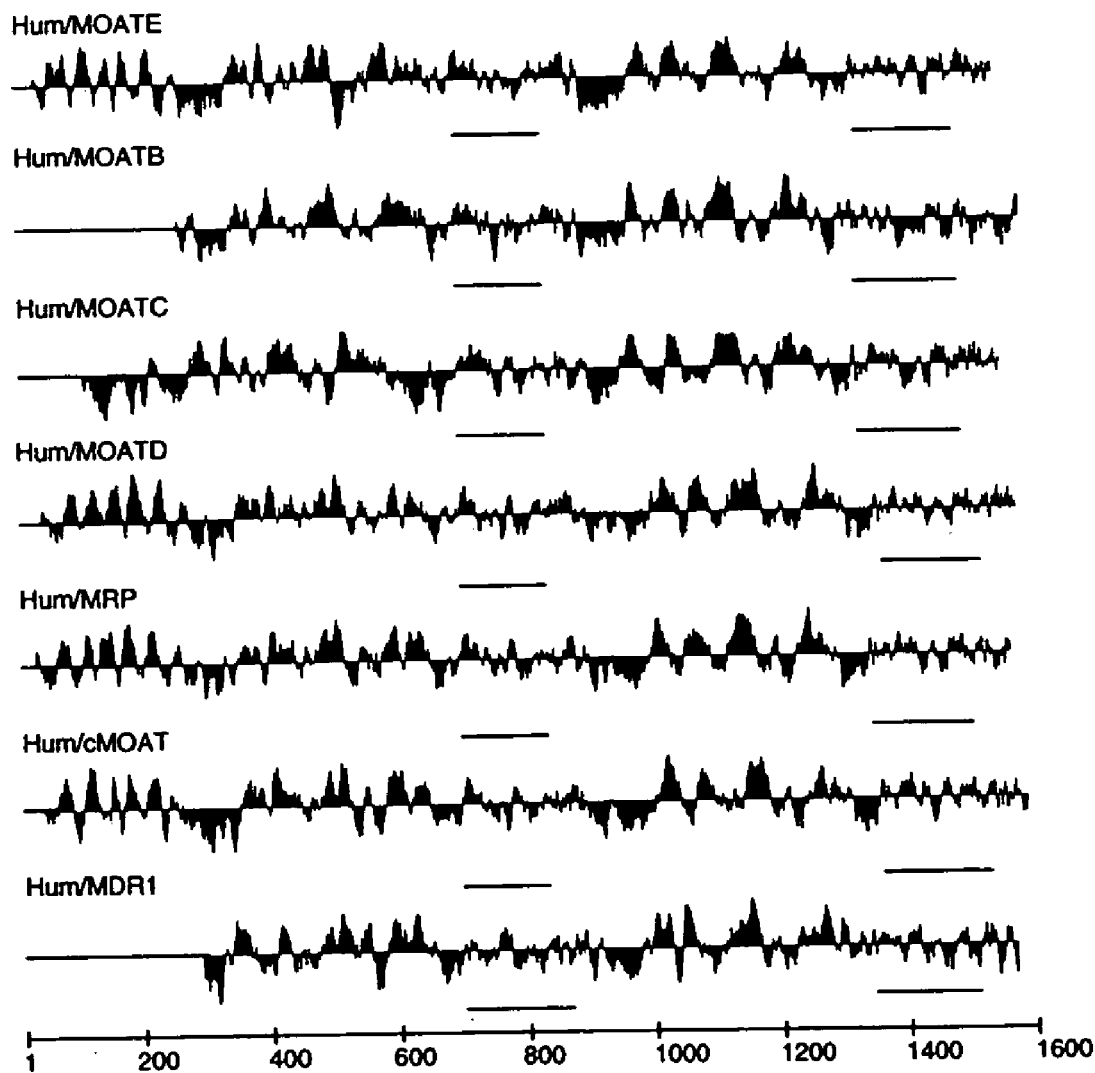
FIG. 10 shows a comparison of the hydropathy profile of MOAT-E with other members of the MRP-cMOAT subfamily. The profile reveals that MOAT-E has a hydrophobic N-terminal segment which is absent in MOAT-B and MOAT-C.

Comparison of the hydropathy profile of MOAT-E with other members of the MRP/cMOAT subfamily if shown in FIG. 10. The data reveal that MOAT-E has a hydrophobic N-terminal segment that is present in its closest relatives, MOAT-D, MRP and cMOAT. This structural feature is present in all of the currently known organic anion transporters, and suggests that MOAT-E may share substrate specificity with MRP and cMOAT. MOAT-E may also share the drug resistance activity of the latter two proteins. In contrast, MOAT-B and MOAT-C do not have this hydrophobic N-terminal extension.

Expression Pattern of MOAT-E in Human Tissues.

Figure 11:
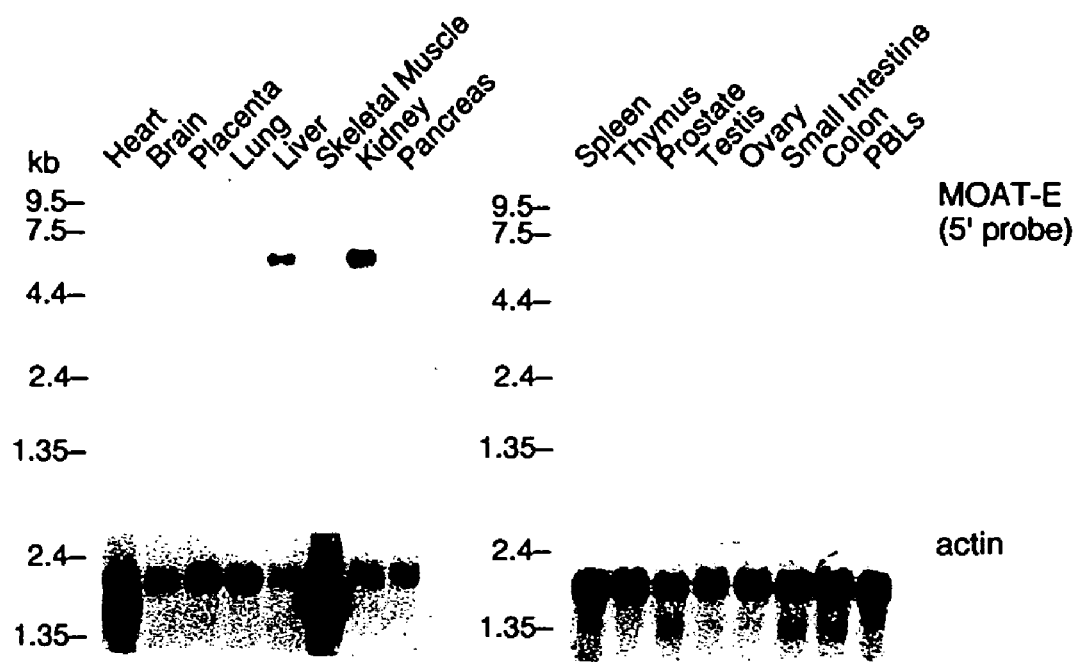
FIG. 11 is a RNA blot which reveals that MOAT-E is expressed only in the liver and the kidney, suggesting that MOAT-E may participate in the excretion of substances into urine and bile. The lower panel shows hybridization of an actin probe to assess RNA loading.

In a Northern blot of RNA isolated from various tissues, MOAT-E expression is restricted to liver and kidney, suggesting that MOAT-E may participate the excretion of substances into the urine and bile. See FIG. 11. This figure also shows that MOAT-E is expressed as an ~6 kB transcript. This is in contrast to the ~2.3 kB transcript that was reported for ara, clearly indicating that the fused ara transcript is unique to the cell line from which it was isolated, and is not a physiological transcript. Together, the isolation of MOAT-E and analysis of its sequence and expression pattern suggest that it may be involved in cellular resistance to drugs and/or the excretion of drugs into the urine and bile.

DISCUSSION

The present invention discloses additional MRP/cMOAT-related transporters which were identified by using a degenerative PCR cloning approach in which the conserved amino terminal ATP-binding domain of known eukaryotic transporters was targeted. Using this approach the complete coding sequences of MOAT-B, MOAT-C, MOAT-D and MOAT-E were obtained. MOAT-B is a protein whose predicted structure indicates that it is a member of the ABC transporter family. Comparison of the MOAT-B predicted protein with other transporters reveals that it is most closely related to MRP, cMOAT and yeast YCF1, and thus extends the number of known full length MRP-related transporters. The similarity of MOAT-B to these transporters suggest that it shares a similar substrate specificity. Transport assays using membrane vesicle preparations indicate that MRP is capable of transporting diverse organic anions, including glutathione S-conjugates such as $LTC_4$, oxidized glutathione, and glucuronidated and sulfated conjugates of steroid hormones and bile salts (7). Although membrane vesicle transport assays of substrate specificity using cMOAT-transfected cells have not yet been reported, genetic and biochemical studies using TR and EHBR rat strains, which are defective in the hepatobiliary excretion of glutathione and glucuronate conjugates, indicate that it is also an ATP-dependent transporter of organic anions. cMOAT, which is primarily expressed in the canalicular membrane of hepatocytes, has been reported to be absent in these rat strains, and hepatocyte canalicular membranes prepared from the mutant rats are deficient in the ATP-dependent transport of glutathione and glucuronate conjugates (23, 24). In addition, cMOAT protein has also been reported to be absent in the hepatocytes of patients with Dubin-Johnson syndrome (25), a disorder manifested by chronic conjugated hyperbilirubinemia. YCF1, a yeast transporter, has also been demonstrated to transport glutathione complexes (26). Thus, based upon the similarity of MOAT-B to these three transporters, it is possible that it also functions to transport organic anions, an activity critical to the cellular detoxification of a wide range of xenobiotics.

MOAT-C, MOAT-D and MOAT-E are three other MRP/cMOAT-related transporters. The isolation of these two transporters extends the number of known full length members of this subfamily to six. Based upon the degree of amino acid similarity and overall topology these six proteins fall into two groups. The first group is composed of MOAT-D, MOAT-E, MRP and cMOAT. These four transporters are highly related, sharing ~39-45% amino acid identity. MOAT-D is more closely related to MRP (57% identity) than is cMOAT (48% identity), and is therefore the closest known relative of MRP. In addition to a high degree of amino acid identity, the similarity between MOAT-D, MRP and cMOAT, also extends to overall topology. Like MRP and cMOAT, MOAT-D and MOAT-E have three membrane spanning domains, including an N-terminal hydrophobic extension that is predicted to harbor ~5 transmembrane helices, and which is absent in transporters such as CFTR and MDR1. This N-terminal extension is also present in YCF1, a related yeast transporter that transports glutathione S-conjugates, and SUR, a more distantly related transporter involved in the regulation of potassium channels. The second group of MRP/cMOAT-related transporters is composed of MOAT-B and MOAT-C. These two transporters are distinguished from the first group by their lower level of amino acid similarity and distinct topology. Like MOAT-D and MOAT-E, MOAT-B and MOAT-C are more closely related to MRP (39% and 36%, respectively) and cMOAT (37% and 36%, respectively) than to other eukaryotic transporters. However, they share considerably less similarity with MRP, cMOAT, MOAT-D and MOAT-E than the latter four transporters share with each other (~39-45% identity). In addition, in contrast to MRP, cMOAT, MOAT-D and MOAT-E, MOAT-B and MOAT-C do not have an N-terminal membrane spanning domain, and their topology is therefore more similar to many other eukaryotic ABC transporters that also have only two membrane spanning domains.

Defining the contributions of MOAT-B, MOAT-C, MOAT-D and MOAT-E to cytotoxic drug resistance will facilitate the design of novel chemotherapeutic agents. The multidrug resistance activity of MRP is well described. While the drug sensitivity pattern of cMOAT-transfected cells has not yet been reported, the possibility that it may also confer resistance to cytotoxic drugs is suggested by a recent report in which transfection of a cMOAT antisense vector was found to enhance the sensitivity of a human liver cancer cell line to both natural product drugs and cisplatin. Since MOAT-D and MOAT-E are more closely related to MRP than is cMOAT, the possibility that they will also confer resistance is particularly intriguing. The availability of the MOAT-B, MOAT-C, MOAT-D and MOAT-E cDNAs will facilitate the analysis of their possible contributions to cytotoxic resistance.

REFERENCES

1. Gottesman, M. M. and Pastan, I. Biochemistry of multidrug resistance mediated by the multidrug transporter. Annu. Rev. Biochem., 62: 385-427, 1993
2. Kruh, G. D., Chan, A., Myers, K., Gaughan, K., Miki, T., and Aaronson, S. A. Expression complementary DNA library transfer establishes mrp as a multidrug resistance gene. Cancer Res., 54: 1649-52, 1994.
3. Zaman, G. J., Flens, M. J., van Leusden, M. R., de Haas, M., Mulder, H. S., Lankelma, J., Pinedo, H. M., Scheper, R. J., Baas, F., Broxterman, H. J., and Borst, P. The human multidrug resistance-associated protein MRP is a plasma membrane drug-efflux pump. Proc. Natl. Acad. Sci. U S A, 91: 8822-6, 1994.
4. Grant, C. E., Valdimarsson, G., Hipfner, D. R., Almquist, K. C., Cole, S. P., and Deeley, R. G. Overexpression of multidrug resistance-associated protein (MRP) increases resistance to natural product drugs. Cancer Res., 54:357-61, 1994.
5. Breuninger, L. M., Paul, S., Gaughan, K., Miki, T., Chan, A., Aaronson, S. A., and Kruh, G. D. Expression of Multidrug Resistance-associated Protein in NIH/3T3 Cells Confers Multidrug Resistance Associated with Increased Drug Efflux and Altered Intracellular Drug Distribution. Cancer Res., 55: 5342-5347, 1995.
6. Cole, S. P., Sparks, K. E., Fraser, K., Loe, D. W., Grant, C. E., Wilson, G. M., and Deeley, R. G. Pharmacological characterization of multidrug resistant MRP-transfected human tumor cells. Cancer Res., 54: 5902-10, 1994.
7. Keppler, D., Leier, I., and Jedlitschky, G. Transport of glutathione conjugates and glucuronides by the multidrug resistance proteins MRP1 and MRP2. Biol. Chem., 378: 787-91, 1997.
8. Lee, J. S., Scala, S., Matsumoto, Y., Dickstein, B., Robey, R., Zhan, Z., Altenberg, G., and Bates, S. E. Reduced drug accumulation and multidrug resistance in human breast cancer cells without associated P-glycoprotein or MRP overexpression. J. Cell. Biochem., 65: 513-26, 1997.
9. Gately, D. P. and Howell, S. B. Cellular accumulation of the anticancer agent cisplatin: a review. Br. J. Cancer, 67: 1171-6, 1993.
10. Ishikawa, T. and Ali-Osman, F. Glutathione-associated cis-diamminedichloroplatinum(II) metabolism and ATP-dependent efflux from leukemia cells. Molecular characterization of glutathione-platinum complex and its biological significance. J. Biol. Chem., 268: 20116-25, 1993.
11. Ishikawa, T., Wright, C. D., and Ishizuka, H. GS-X pump is functionally overexpressed in cis-diamminedichloroplatinum (II)-resistant human leukemia HL-60 cells and down-regulated by cell differentiation. J. Biol. Chem., 269: 29085-93, 1994.
12. Fujii, R., Mutoh, M., Sumizawa, T., Chen, Z. S., Yoshimura, A., and Akiyama, S. Adenosine triphosphate-dependent transport of leukotriene C4 by membrane vesicles prepared from cisplatin-resistant human epidermoid carcinoma tumor cells [see comments]. J. Natl. Cancer Inst., 86: 1781-4, 1994.
13. Ishikawa, T., Bao, J. J., Yamane, Y., Akimaru, K., Frindrich, K., Wright, C. D., and Kuo, M. T. Coordinated induction of MRP/GS-X pump and gamma-glutamylcysteine synthetase by heavy metals in human leukemia cells. J. Biol. Chem., 271: 14981-8, 1996.
14. Taniguchi, K., Wada, M., Kohno, K., Nakamura, T., Kawabe, T., Kawakami, M., Kagotani, K., Okumura, K., Akiyama, S., and Kuwano, M. A human canalicular multispecific organic anion transporter (cMOAT) gene is overexpressed in cisplatin-resistant human cancer cell lines with decreased drug accumulation. Cancer Res., 56: 4124-9, 1996.
15. Kool, M., de Haas, M., Scheffer, G. L., Scheper, R. J., van Eijk, M. J., Juijn, J. A., Baas, F., and Borst, P. Analysis of expression of cMOAT (MRP2), MRP3, MRP4, and MRP5, homologues of the multidrug resistance-associated protein gene (MRP1), in human cancer cell lines. Cancer Res., 57: 3537-47, 1997.
16. Koike, K., Kawabe, T., Tanaka, T., Toh, S., Uchiumi, T., Wada, M., Akiyama, S., Ono, M., and Kuwano, M. A canalicular multispecific organic anion transporter (cMOAT) antisense cDNA enhances drug sensitivity in human hepatic cancer cells. Cancer Res., 57: 5475-9, 1997.
17. Miki, T., Fleming, T. P., Crescenzi, M., Molloy, C. J., Blam, S. B., Reynolds, S. H., and Aaronson, S. A. Development of a highly efficient expression cDNA cloning system: application to oncogene isolation. Proc. Natl. Acad. Sci. U S A, 88: 5167-71, 1991.
18. Bell, D. W., Taguchi, T., Jenkins, N. A., Gilbert, D. J., Copeland, N. G., Gilks, C. B., Zweidler-McKay, P., Grimes, H. L., Tsichlis, P. N., and Testa, J. R. Chromosomal localization of a gene, GF1, encoding a novel zinc finger protein reveals a new syntenic region between man and rodents. Cytogenet. Cell. Genet., 70: 263-7, 1995.
19. Persson, B. and Argos, P. Prediction of transmembrane segments in proteins utilising multiple sequence alignments. J. Mol. Biol., 237: 182-92, 1994.
20. Bakos, E., Hegedus, T., Hollo, Z., Welker, E., Tusnady, G. E., Zaman, G. J., Flens, M. J., Varadi, A., and Sarkadi, B. Membrane topology and glycosylation of the human multidrug resistance-associated protein. J. Biol. Chem., 271: 12322-6, 1996.
21. Loo, T. W. and Clarke, D. M. Membrane topology of a cysteine-less mutant of human P-glycoprotein. J. Biol. Chem., 270: 843-8, 1995.
22. Tusnady, G. E., Bakos, E., Varadi, A., and Sarkadi, B. Membrane topology distinguishes a subfamily of the ATP-binding cassette (ABC) transporters. FEBS Lett., 402: 1-3, 1997.
23. Paulusma, C. C., Bosma, P. J., Zaman, G. J., Bakker, C. T., Otter, M., Scheffer, G. L., Scheper, R. J., Borst, P., and Oude Elferink, R. P. Congenital jaundice in rats with a mutation in a multidrug resistance-associated protein gene. Science, 271: 1126-82, 1996.
24. Buchler, M., Konig, J., Brom, M., Kartenbeck, J., Spring, H.,Horie, T., and Keppler, D. cDNA cloning of the hepatocyte canalicular isoform of the multidrug resistance protein, cMrp, reveals a novel conjugate export pump deficient in hyperbilirubinemic mutant rats. J. Biol. Chem., 271: 15091-8, 1996.
25. Kartenbeck, J., Leuschner, U., Mayer, R., and Keppler, D. Absence of the canalicular isoform of the MRP gene-encoded conjugate export pump from the hepatocytes in Dubin-Johnson syndrome. Hepatology, 23: 1061-6, 1996.
26. Li, Z. S., Szczypka, M., Lu, Y. P., Thiele, D. J., and Rea, P. A. The yeast cadmium factor protein (YCF1) is a vacuolar glutathione S-conjugate pump. J. Biol. Chem., 271: 6509-17, 1996.
27. Wemmie, J. A. and Moye-Rowley, W. S. Mutational analysis of the Saccharomyces cerevisiae ATP-binding cassette transporter protein Ycflp. Mol. Microbiol., 25: 683-94, 1997.
28. Kruh, G. D., Gaughan, K. T., Godwin, A. K., and Chan, A. Expression Pattern of MRP in Human Tissues and Adult Solid Tumor Cell Lines. J. Natl. Cancer Inst., 87: 1256-58, 1995.
29. Longhurst, T. J., O'Neill, G. M., Harvie, R. M., and Davey, R. A. The anthracycline resistance-associated (ara) gene, a novel gene associated with multidrug resistance in a human leukaemia cell line. Br. J. Cancer, 74: 1331-5, 1996.
30. Allikmets, R., Gerrard, B., Hutchinson, A., and Dean, M. Characterization of the human ABC superfamily: isolation and mapping of 21 new genes using the expressed sequence tags database. Hum. Mol. Genet., 5: 1649-55, 1996.
31. Shen, D.-w., Pastan, I., and Gottesman, M. M. Cross-Resistance to Methotrexate and Metals in Human Cisplatin-resistant Cell Lines Results from a Pleiotroic Defect n Accumulation of These Compounds Associated with Reduced Plasma Membrane Binding Proteins. Cancer Res., 58: 268-275, 1998.
32. Naredi, P., Heath, D. D., Enns, R. E., and Howell, S. B. Cross-resistance between cisplatin and antimony in a human ovarian carcinoma cell line. Cancer Res., 54: 6464-8, 1994.
33. Naredi, P., Heath, D. D., Enns, R. E., and Howell, S. B. Cross-resistance between cisplatin, antimony potassium tartrate, and arsenite in human tumor cells. J. Clin. Invest., 95: 1193-8, 1995.
34. Wemmie, J. A., Szczypka, M. S., Thiele, D. J., and Moye-Rowley, W. S. Cadmium tolerance mediated by the yeast AP-1 protein requires the presence of an ATP-binding cassette transporter-encoding gene, YCF1. J. Biol. Chem., 269: 32592-7, 1994.
35. O'Dwyer, P. J., Johnson, S. W., and Hamilton, T. C. Cisplatin and its Analogues. In: V. T. J. DeVita, S. Hellman, and S. A. Rosenberg (eds.), Cancer Principles and Practice of Oncology, pp. 418-432. Philadelphia: Lippincott-Raven, 1997.
36. Altschul, S. F., Gish, W., Miller, W., Myers, E. W., and Lipman, D. J. Basic Local Alignment Search Tool. J. Mol. Biol. 215:403-10, 1990.
37. Kozak, M. Compilation and analysis of sequences upstream from the translational start site in eukaryotic mRNAs. Nuc. Acids. Res. 12:857-72.
38. Tusnady, G.E., Bakos, E., Varadi, A., Sarkadi, B. Membrane topology distinguishes a subfamily of the ATP-binding cassette (ABC) transporters. FEBS Lett. 402:1-3, 1997.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

SEQUENCE LISTING

<160> NUMBER OF SEQ ID NOS: 33

<210> SEQ ID NO 1
<211> LENGTH: 4231
<212> TYPE: DNA
<213> ORGANISM: Homo sapiens -continued

<400> SEQUENCE: 1

| | | | | | |
|---|---|---|---|---|---|
| ggacaggcgt | ggcggccgga | gccccagcat | ccctgcttga | ggtccaggag | cggagcccgc | 60 |
| ggccaccgcc | gcctgatcag | cgcgacccg | gcccgcgccc | gccccgcccg | gcaagatgct | 120 |
| gcccgtgtac | caggaggtga | agcccaaccc | gctgcaggac | gcgaacatct | gctcacgcgt | 180 |
| gttcttctgg | tggctcaatc | ccttgtttaa | aattggccat | aaacggagat | tagaggaaga | 240 |
| tgatatgtat | tcagtgctgc | cagaagaccg | ctcacacac | cttggagagg | agttgcaagg | 300 |
| gttctgggat | aaagaagttt | taagagctga | gaatgacgca | cagaagcctt | ctttaacaag | 360 |
| agcaatcata | aagtgttact | ggaaatctta | tttagttttg | ggaattttta | cgttaattga | 420 |
| ggaaagtgcc | aaagtaatcc | agcccatatt | tttgggaaaa | attattaatt | attttgaaaa | 480 |
| ttatgatccc | atggattctg | tggctttgaa | cacagcgtac | gcctatgcca | cggtgctgac | 540 |
| ttttttgcacg | ctcattttgg | ctatactgca | tcacttatat | ttttatcacg | ttcagtgtgc | 600 |
| tgggatgagg | ttacgagtag | ccatgtgcca | tatgatttat | cggaaggcac | ttcgtcttag | 660 |
| taacatggcc | atgggaaga | caaccacagg | ccagatagtc | aatctgctgt | ccaatgatgt | 720 |
| gaacaagttt | gatcaggtga | cagtgttctt | acacttcctg | tgggcaggac | cactgcaggc | 780 |
| gatcgcagtg | actgccctac | tctggatgga | gataggaata | tcgtgccttg | ctgggatggc | 840 |
| agttctaatc | attctcctgc | ccttgcaaag | ctgttttggg | aagttgttct | catcactgag | 900 |
| gagtaaaaact | gcaactttca | cggatgccag | gatcaggacc | atgaatgaag | ttataactgg | 960 |
| tataaggata | ataaaaatgt | acgcctggga | aaagtcattt | tcaaatctta | ttaccaattt | 1020 |
| gagaaagaag | gagatttcca | agattctgag | aagttcctgc | ctcaggggga | tgaatttggc | 1080 |
| ttcgttttc | agtgcaagca | aaatcatcgt | gtttgtgacc | ttcaccaccct | acgtgctcct | 1140 |
| cggcagtgtg | atcacagcca | gccgcgtgtt | cgtggcagtg | acgctgtatg | gggctgtgcg | 1200 |
| gctgacggtt | accctcttct | tcccctcagc | cattgagagg | gtgtcagagg | caatcgtcag | 1260 |
| catccgaaga | atccagacct | ttttgctact | tgatgagata | tcacagcgca | accgtcagct | 1320 |
| gccgtcagat | ggtaaaaaga | tggtgcatgt | gcaggatttt | actgcttttt | gggataaggc | 1380 |
| atcagagacc | ccaactctac | aaggccttc | ctttactgtc | agacctggcg | aattgttagc | 1440 |
| tgtggtcggc | cccgtgggag | cagggaagtc | atcactgtta | agtgccgtgc | tcggggaatt | 1500 |
| ggccccaagt | cacgggctgg | tcagcgtgca | tggaagaatt | gcctatgtgt | ctcagcagcc | 1560 |
| ctgggtgttc | tcgggaactc | tgaggagtaa | tattttattt | gggaagaaat | atgaaaagga | 1620 |
| acgatatgaa | aaagtcataa | aggcttgtgc | tctgaaaaag | gatttacagc | tgttggagga | 1680 |
| tggtgatctg | actgtgatag | gagatcgggg | aaccacgctg | agtggagggc | agaaagcacg | 1740 |
| ggtaaaccctt | gcaagagcag | tgtatcaaga | tgctgacatc | tatctcctgg | acgatcctct | 1800 |
| cagtgcagta | gatgcggaag | ttagcagaca | cttgttcgaa | ctgtgtattt | gtcaaatttt | 1860 |
| gcatgagaag | atcacaattt | tagtgactca | tcagttgcag | tacctcaaag | ctgcaagtca | 1920 |
| gattctgata | ttgaaagatg | gtaaaatggt | gcagaagggg | acttacactg | agttcctaaa | 1980 |
| atctggtata | gattttggct | ccctttaaa | gaaggataat | gaggaaagtg | aacaacctcc | 2040 |
| agttccagga | actcccacac | taaggaatcg | taccttctca | gagtcttcgg | tttggtctca | 2100 |
| acaatcttct | agaccctcct | tgaaagatgg | tgctctggag | agccaagata | cagagaatgt | 2160 |
| cccagttaca | ctatcagagg | agaaccgttc | tgaaggaaaa | gttggttttc | aggcctataa | 2220 |
| gaattacttc | agagctggtg | ctcactggat | tgtcttcatt | ttccttattc | tcctaaacac | 2280 |
| tgcagctcag | gttgcctatg | tgcttcaaga | ttggtggctt | tcatactggg | caaacaaaca | 2340 |

-continued

```
aagtatgcta aatgtcactg taaatggagg aggaaatgta accgagaagc tagatcttaa    2400
ctggtactta ggaatttatt caggtttaac tgtagctacc gttcttttttg gcatagcaag   2460 atctctattg gtattctacg tccttgttaa ctcttcacaa actttgcaca acaaaatgtt    2520
tgagtcaatt ctgaaagctc cggtattatt ctttgataga aatccaatag aagaatttt    2580 aaatcgtttc tccaaagaca ttggacactt ggatgatttg ctgccgctga cgttttttaga  2640 tttcatccag acattgctac aagtggttgg tgtggtctct gtggctgtgg ccgtgattcc    2700
ttggatcgca ataccttgg ttcccccttgg aatcattttc attttctttc ggcgatatttt 2760 tttggaaacg tcaagagatg tgaagcgcct ggaatctaca actcggagtc cagtgttttc    2820
ccacttgtca tcttctctcc aggggctctg gaccatccgg gcatacaaag cagaagagag    2880
gtgtcaggaa ctgtttgatg cacaccagga tttacattca gaggcttggt tcttgttttt    2940
gacaacgtcc cgctggttcg ccgtccgtct ggatgccatc tgtgccatgt ttgtcatcat    3000
cgttgccttt gggtccctga ttctggcaaa actctggat gccgggcagg ttggtttggc    3060
actgtcctat gccctcacgc tcatggggat gtttcagtgg tgtgttcgac aaagtgctga    3120
agttgagaat atgatgatct cagtagaaag ggtcattgaa tacacagacc ttgaaaaga    3180 agcaccttgg gaatatcaga aacgcccacc accagcctgg ccccatgaag gagtgataat    3240
ctttgacaat gtgaacttca tgtacagtcc aggtgggcct ctggtactga agcatctgac    3300
agcactcatt aaatcacaag aaaaggttgg cattgtggga agaaccggag ctggaaaaag    3360
ttccctcatc tcagcccttt ttagattgtc agaacccgaa ggtaaaattt ggattgataa    3420
gatcttgaca actgaaattg gacttcacga tttaaggaag aaaatgtcaa tcatacctca    3480
ggaacctgtt ttgttcactg gaacaatgag gaaaaacctg gatccctta aggagcacac    3540 ggatgaggaa ctgtggaatg ccttacaaga ggtacaactt aaagaaacca ttgaagatct    3600
tcctggtaaa atggatactg aattagcaga atcaggatcc aatttttagtg ttggacaaag   3660 acaactggtg tgccttgcca gggcaattct caggaaaaat cagatattga ttattgatga    3720
agcgacggca aatgtggatc caagaactga tgagttaata caaaaaaaaa tccgggagaa    3780
atttgcccac tgcaccgtgc taaccattgc acacagattg aacaccatta ttgacagcga    3840
caagataatg gttttagatt caggaagact gaaagaatat gatgagccgt atgttttgct    3900
gcaaaataaa gagagcctat tttacaagat ggtgcaacaa ctgggcaagg cagaagccgc    3960
tgccctcact gaaacagcaa aacaggtata cttcaaaaga aattatccac atattggtca    4020
cactgaccac atggttacaa acacttccaa tggacagccc tcgaccttaa ctattttcga    4080
gacagcactg tgaatccaac caaaatgtca agtccgttcc gaaggcattt tccactagtt    4140
tttggactat gtaaaccaca ttgtactttt ttttactttg gcaacaaata tttatacata    4200
caagatgcta gttcatttga atatttctcc c                                  4231
```

<210> SEQ ID NO 2
<211> LENGTH: 1325
<212> TYPE: PRT
<213> ORGANISM: Homo sapiens

<400> SEQUENCE: 2

```
Met Leu Pro Val Tyr Gln Glu Val Lys Pro Asn Pro Leu Gln Asp Ala
 1               5                  10                  15

Asn Ile Cys Ser Arg Val Phe Phe Trp Trp Leu Asn Pro Leu Phe Lys
            20                  25                  30
```

```
Ile Gly His Lys Arg Arg Leu Glu Glu Asp Asp Met Tyr Ser Val Leu
         35                  40                  45
Pro Glu Asp Arg Ser Gln His Leu Gly Glu Glu Leu Gln Gly Phe Trp
 50                  55                  60
Asp Lys Glu Val Leu Arg Ala Glu Asn Asp Ala Gln Lys Pro Ser Leu
 65                  70                  75                  80
Thr Arg Ala Ile Ile Lys Cys Tyr Trp Lys Ser Tyr Leu Val Leu Gly
                 85                  90                  95
Ile Phe Thr Leu Ile Glu Ser Ala Lys Val Ile Gln Pro Ile Phe
             100                 105                 110
Leu Gly Lys Ile Ile Asn Tyr Phe Glu Asn Tyr Asp Pro Met Asp Ser
             115                 120                 125
Val Ala Leu Asn Thr Ala Tyr Ala Tyr Ala Thr Val Leu Thr Phe Cys
 130                 135                 140
Thr Leu Ile Leu Ala Ile Leu His His Leu Tyr Phe Tyr His Val Gln
145                 150                 155                 160
Cys Ala Gly Met Arg Leu Arg Val Ala Met Cys His Met Ile Tyr Arg
                 165                 170                 175
Lys Ala Leu Arg Leu Ser Asn Met Ala Met Gly Lys Thr Thr Thr Gly
             180                 185                 190
Gln Ile Val Asn Leu Leu Ser Asn Asp Val Asn Lys Phe Asp Gln Val
             195                 200                 205
Thr Val Phe Leu His Phe Leu Trp Ala Gly Pro Leu Gln Ala Ile Ala
 210                 215                 220
Val Thr Ala Leu Leu Trp Met Glu Ile Gly Ile Ser Cys Leu Ala Gly
225                 230                 235                 240
Met Ala Val Leu Ile Ile Leu Leu Pro Leu Gln Ser Cys Phe Gly Lys
                 245                 250                 255
Leu Phe Ser Ser Leu Arg Ser Lys Thr Ala Thr Phe Thr Asp Ala Arg
             260                 265                 270
Ile Arg Thr Met Asn Glu Val Ile Thr Gly Ile Arg Ile Ile Lys Met
             275                 280                 285
Tyr Ala Trp Glu Lys Ser Phe Ser Asn Leu Ile Thr Asn Leu Arg Lys
 290                 295                 300
Lys Glu Ile Ser Lys Ile Leu Arg Ser Ser Cys Leu Arg Gly Met Asn
305                 310                 315                 320
Leu Ala Ser Phe Phe Ser Ala Ser Lys Ile Ile Val Phe Val Thr Phe
                 325                 330                 335
Thr Thr Tyr Val Leu Leu Gly Ser Val Ile Thr Ala Ser Arg Val Phe
             340                 345                 350
Val Ala Val Thr Leu Tyr Gly Ala Val Arg Leu Thr Val Thr Leu Phe
             355                 360                 365
Phe Pro Ser Ala Ile Glu Arg Val Ser Glu Ala Ile Val Ser Ile Arg
 370                 375                 380
Arg Ile Gln Thr Phe Leu Leu Asp Glu Ile Ser Gln Arg Asn Arg
385                 390                 395                 400
Gln Leu Pro Ser Asp Gly Lys Lys Met Val His Val Gln Asp Phe Thr
                 405                 410                 415
Ala Phe Trp Asp Lys Ala Ser Glu Thr Pro Thr Leu Gln Gly Leu Ser
             420                 425                 430
Phe Thr Val Arg Pro Gly Glu Leu Leu Ala Val Val Gly Pro Val Gly
             435                 440                 445
Ala Gly Lys Ser Ser Leu Leu Ser Ala Val Leu Gly Glu Leu Ala Pro
```

-continued

```
            450                 455                 460
Ser His Gly Leu Val Ser Val His Gly Arg Ile Ala Tyr Val Ser Gln
465                 470                 475                 480

Gln Pro Trp Val Phe Ser Gly Thr Leu Arg Ser Asn Ile Leu Phe Gly
                485                 490                 495

Lys Lys Tyr Glu Lys Glu Arg Tyr Glu Lys Val Ile Lys Ala Cys Ala
            500                 505                 510

Leu Lys Lys Asp Leu Gln Leu Leu Glu Asp Gly Asp Leu Thr Val Ile
        515                 520                 525

Gly Asp Arg Gly Thr Pro Leu Ser Gly Gly Gln Lys Ala Arg Val Asn
530                 535                 540

Leu Ala Arg Ala Val Tyr Gln Asp Ala Asp Ile Tyr Leu Leu Asp Asp
545                 550                 555                 560

Pro Leu Ser Ala Val Asp Ala Glu Val Ser Arg His Leu Phe Glu Leu
                565                 570                 575

Cys Ile Cys Gln Ile Leu His Glu Lys Ile Thr Ile Leu Val Thr His
            580                 585                 590

Gln Leu Gln Tyr Leu Lys Ala Ala Ser Gln Ile Leu Ile Leu Lys Asp
        595                 600                 605

Gly Lys Met Val Gln Lys Gly Thr Tyr Thr Glu Phe Leu Lys Ser Gly
610                 615                 620

Ile Asp Phe Gly Ser Leu Leu Lys Lys Asp Asn Glu Glu Ser Glu Gln
625                 630                 635                 640

Pro Pro Val Pro Gly Thr Pro Thr Leu Arg Asn Arg Thr Phe Ser Glu
                645                 650                 655

Ser Ser Val Trp Ser Gln Gln Ser Ser Arg Pro Ser Leu Lys Asp Gly
            660                 665                 670

Ala Leu Glu Ser Gln Asp Thr Glu Asn Val Pro Val Thr Leu Ser Glu
        675                 680                 685

Glu Asn Arg Ser Glu Gly Lys Val Gly Phe Gln Ala Tyr Lys Asn Tyr
        690                 695                 700

Phe Arg Ala Gly Ala His Trp Ile Val Phe Ile Phe Leu Ile Leu Leu
705                 710                 715                 720

Asn Thr Ala Ala Gln Val Ala Tyr Val Leu Gln Asp Trp Trp Leu Ser
                725                 730                 735

Tyr Trp Ala Asn Lys Gln Ser Met Leu Asn Val Thr Val Asn Gly Gly
            740                 745                 750

Gly Asn Val Thr Glu Lys Leu Asp Leu Asn Trp Tyr Leu Gly Ile Tyr
        755                 760                 765

Ser Gly Leu Thr Val Ala Thr Val Leu Phe Gly Ile Ala Arg Ser Leu
770                 775                 780

Leu Val Phe Tyr Val Leu Val Asn Ser Ser Gln Thr Leu His Asn Lys
785                 790                 795                 800

Met Phe Glu Ser Ile Leu Lys Ala Pro Val Leu Phe Asp Arg Asn
                805                 810                 815

Pro Ile Gly Arg Ile Leu Asn Arg Phe Ser Lys Asp Ile Gly His Leu
            820                 825                 830

Asp Asp Leu Leu Pro Leu Thr Phe Leu Asp Phe Ile Gln Thr Leu Leu
        835                 840                 845

Gln Val Val Gly Val Val Ser Val Ala Val Ala Val Ile Pro Trp Ile
        850                 855                 860

Ala Ile Pro Leu Val Pro Leu Gly Ile Ile Phe Ile Phe Leu Arg Arg
865                 870                 875                 880
```

```
Tyr Phe Leu Glu Thr Ser Arg Asp Val Lys Arg Leu Glu Ser Thr Thr
                885                 890                 895

Arg Ser Pro Val Phe Ser His Leu Ser Ser Leu Gln Gly Leu Trp
            900                 905                 910

Thr Ile Arg Ala Tyr Lys Ala Glu Glu Arg Cys Gln Glu Leu Phe Asp
            915                 920                 925

Ala His Gln Asp Leu His Ser Glu Ala Trp Phe Leu Phe Leu Thr Thr
            930                 935                 940

Ser Arg Trp Phe Ala Val Arg Leu Asp Ala Ile Cys Ala Met Phe Val
945                 950                 955                 960

Ile Ile Val Ala Phe Gly Ser Leu Ile Leu Ala Lys Thr Leu Asp Ala
            965                 970                 975

Gly Gln Val Gly Leu Ala Leu Ser Tyr Ala Leu Thr Leu Met Gly Met
            980                 985                 990

Phe Gln Trp Cys Val Arg Gln Ser Ala Glu Val Glu Asn Met Met Ile
            995                 1000                1005

Ser Val Glu Arg Val Ile Glu Tyr Thr Asp Leu Glu Lys Glu Ala Pro
            1010                1015                1020

Trp Glu Tyr Gln Lys Arg Pro Pro Ala Trp Pro His Glu Gly Val
1025                1030                1035                1040

Ile Ile Phe Asp Asn Val Asn Phe Met Tyr Ser Pro Gly Gly Pro Leu
            1045                1050                1055

Val Leu Lys His Leu Thr Ala Leu Ile Lys Ser Gln Glu Lys Val Gly
            1060                1065                1070

Ile Val Gly Arg Thr Gly Ala Gly Lys Ser Ser Leu Ile Ser Ala Leu
            1075                1080                1085

Phe Arg Leu Ser Glu Pro Glu Gly Lys Ile Trp Ile Asp Lys Ile Leu
            1090                1095                1100

Thr Thr Glu Ile Gly Leu His Asp Leu Arg Lys Lys Met Ser Ile Ile
1105                1110                1115                1120

Pro Gln Glu Pro Val Leu Phe Thr Gly Thr Met Arg Lys Asn Leu Asp
            1125                1130                1135

Pro Phe Lys Glu His Thr Asp Glu Glu Leu Trp Asn Ala Leu Arg Glu
            1140                1145                1150

Val Gln Leu Lys Glu Thr Ile Glu Asp Leu Pro Gly Lys Met Asp Thr
            1155                1160                1165

Glu Leu Ala Glu Ser Gly Ser Asn Phe Ser Val Gly Gln Arg Gln Leu
            1170                1175                1180

Val Cys Leu Ala Arg Ala Ile Leu Arg Lys Asn Gln Ile Leu Ile Ile
1185                1190                1195                1200

Asp Glu Ala Thr Ala Asn Val Asp Pro Arg Thr Asp Glu Leu Ile Gln
            1205                1210                1215

Lys Lys Ile Arg Glu Lys Phe Ala His Cys Thr Val Leu Thr Ile Ala
            1220                1225                1230

His Arg Leu Asn Thr Ile Ile Asp Ser Asp Lys Ile Met Val Leu Asp
            1235                1240                1245

Ser Gly Arg Leu Lys Glu Tyr Asp Glu Pro Tyr Val Leu Leu Gln Asn
            1250                1255                1260

Lys Glu Ser Leu Phe Tyr Lys Met Val Gln Gln Leu Gly Lys Ala Glu
1265                1270                1275                1280

Ala Ala Ala Leu Thr Glu Thr Ala Lys Gln Val Tyr Phe Lys Arg Asn
            1285                1290                1295
```

```
Tyr Pro His Ile Gly His Thr Asp His Met Val Thr Asn Thr Ser Asn
            1300                1305                1310
Gly Gln Pro Ser Thr Leu Thr Ile Phe Glu Thr Ala Leu
        1315                1320                1325

<210> SEQ ID NO 3
<211> LENGTH: 5838
<212> TYPE: DNA
<213> ORGANISM: Homo sapiens

<400> SEQUENCE: 3
ccgggcaggt ggctcatgct cgggagcgtg gttgagcggc tggcgcggtt gtcctggagc      60
aggggcgcag gaattctgat gtgaaactaa cagtctgtga gccctggaac ctccgctcag     120
agaagatgaa ggtatcgac ataggaaaag agtatatcat ccccagtcct gggtatagaa      180
gtgtgaggga gagaaccagc acttctggga cgcacagaga ccgtgaagat tccaagttca     240
ggagaactcg accgttggaa tgccaagatg ccttggaaac agcagcccga ccgagggcc     300 tctctcttga tgcctccatg cattctcagc tcagaatcct ggatgaggag catcccaagg     360
gaaagtacca tcatggcttg agtgctctga agcccatccg gactacttcc aaacaccagc     420
acccagtgga caatgctggg cttttttcct gtatgacttt ttcgtggctt tcttctctgg     480
cccgtgtggc ccacaagaag ggggagctct caatggaaga cgtgtggtct ctgtccaagc     540
acgagtcttc tgacgtgaac tgcagaagac tagagagact gtggcaagaa gagctgaatg     600
aagttgggcc agacgctgct tccctgcgaa gggttgtgtg gatcttctgc cgcaccaggc     660
tcatcctgtc catcgtgtgc ctgatgatca cgcagctggc tggcttcagt ggaccagcct     720
tcatggtgaa acacctcttg gagtataccc aggcaacaga gtctaacctg cagtacagct     780
tgttgttagt gctgggcctc ctcctgacgg aaatcgtgcg gtcttggtcg cttgcactga     840
cttgggcatt gaattaccga accggtgtcc gcttgcgggg ggccatccta accatggcat     900
ttaagaagat ccttaagtta aagaacatta agagaaatc cctgggtgag ctcatcaaca     960
tttgctccaa cgatgggcag agaatgtttg aggcagcagc cgttggcagc ctgctggctg    1020
gaggacccgt tgttgccatc ttaggcatga tttataatgt aattattctg ggaccaacag    1080
gcttcctggg atcagctgtt tttatcctct tttacccagc aatgatgttt gcatcacggc    1140
tcacagcata tttcaggaga aaatgcgtgg ccgccacgga tgaacgtgtc cagaagatga    1200
atgaagttct tacttacatt aaatttatca aaatgtatgc ctgggtcaaa gcattttctc    1260
agagtgttca aaaaatccgc gaggaggagc gtcggatatt ggaaaaagcc gggtacttcc    1320
agggtatcac tgtgggtgtg gctcccattg tggtggtgat tgccagcgtg gtgaccttct    1380
ctgttcatat gaccctgggc ttcgatctga cagcagcaca ggctttcaca gtggtgacag    1440
tcttcaattc catgacttt gctttgaaag taacaccgtt ttcagtaaag tccctctcag    1500
aagcctcagt ggctgttgac agatttaaga gtttgttct aatggaagag gttcacatga    1560
taaagaacaa accagccagt cctcacatca agatagagat gaaaaatgcc accttggcat    1620
gggactcctc ccactccagt atccagaact cgcccaagct gacccccaaa atgaaaaaag    1680
acaagagggc ttccaggggc aagaaagaga aggtgaggca gctgcagcgc actgagcatc    1740
aggcggtgct ggcagagcag aaaggccacc tcctcctgga cagtgacgag cggcccagtc    1800
ccgaagagga agaaggcaag cacatccacc tgggccacct gcgcttacag aggacactgc    1860
acagcatcga tctggagatc caagagggta aactggttgg aatctgcggc agtgtgggaa    1920
gtggaaaaac ctctctcatt tcagccattt taggccagat gacgcttcta gagggcagca    1980
```

-continued

```
ttgcaatcag tggaaccttc gcttatgtgg cccagcaggc ctggatcctc aatgctactc    2040
tgagagacaa catcctgttt gggaaggaat atgatgaaga agatacaac tctgtgctga     2100 acagctgctg cctgaggcct gacctggcca ttcttcccag cagcgacctg acggagattg    2160
gagagcgagg agccaacctg agcggtgggc agcgccagag gatcagcctt gcccgggcct    2220
tgtatagtga caggagcatc tacatcctgg acgacccct cagtgcctta gatgcccatg     2280
tgggcaacca catcttcaat agtgctatcc ggaaacatct caagtccaag acagttctgt    2340
ttgttaccca ccagttacag tacctggttg actgtgatga agtgatcttc atgaaagagg    2400
gctgtattac ggaaagaggc acccatgagg aactgatgaa tttaaatggt gactatgcta    2460
ccatttttaa taacctgttg ctgggagaga caccgccagt tgagatcaat tcaaaaaagg    2520
aaaccagtgg ttcacagaag aagtcacaag acaagggtcc taaaacagga tcagtaaaga    2580
aggaaaaagc agtaaagcca gaggaagggc agcttgtgca gctggaagag aaagggcagg    2640
gttcagtgcc ctggtcagta tatggtgtct acatccaggc tgctgggggc cccttggcat    2700
tcctggttat tatggccctt ttcatgctga atgtaggcag caccgccttc agcacctggt    2760
ggttgagtta ctggatcaag caaggaagcg ggaacaccac tgtgactcga gggaacgaga    2820
cctcggtgag tgacagcatg aaggacaatc ctcatatgca gtactatgcc agcatctacg    2880
ccctctccat ggcagtcatg ctgatcctga aagccattcg aggagttgtc tttgtcaagg    2940
gcacgctgcg agcttcctcc cggctgcatg acgagctttt ccgaaggatc cttcgaagcc    3000
ctatgaagtt ttttgacacg acccccacag ggaggattct caacaggttt tccaaagaca    3060
tggatgaagt tgacgtgcgg ctgccgttcc aggccgagat tgttcatccag aacgttatcc    3120 tggtgttctt ctgtgtggga atgatcgcag gagtcttccc gtggttcctt gtggcagtgg    3180
ggccccttgt catcctcttt tcagtcctgc acattgtctc cagggtcctg attcgggagc    3240
tgaagcgtct ggacaatatc acgcagtcac ctttcctctc ccacatcacg tccagcatac    3300
agggccttgc caccatccac gcctacaata aagggcagga gtttctgcac agataccagg    3360
agctgctgga tgacaaccaa gctccttttt ttttgtttac gtgtgcgatg cggtggctgg    3420
ctgtgcggct ggacctcatc agcatcgccc tcatcaccac cacgggctg atgatcgttc     3480 ttatgcacgg gcagattccc ccagcctatg cgggtctcgc catctcttat gctgtccagt    3540
taacggggct gttccagttt acggtcagac tggcatctga gacagaagct cgattcacct    3600
cggtggagag gatcaatcac tacattaaga ctctgtcctt ggaagcacct gccagaatta    3660
agaacaaggc tccctcccct gactggcccc aggagggaga ggtgaccttt gagaacgcag    3720
agatgaggta ccgagaaaac ctccctcttg tcctaaagaa agtatccttc acgatcaaac    3780
ctaaagagaa gattggcatt gtgggcgga caggatcagg gaagtcctcg ctgggatgg      3840 ccctcttccg tctggtggag ttatctggag gctgcatcaa gattgatgga gtgagaatca    3900
gtgatattgg ccttgccgac ctccgaagca aactctctat cattcctcaa gagccggtgc    3960
tgttcagtgg cactgtcaga tcaaatttgg accccttcaa ccagtacact gaagaccaga    4020
tttgggatgc cctggagagg acacacatga agaatgtat tgctcagcta cctctgaaac      4080
ttgaatctga agtgatggag aatgggggata acttctcagt gggggaacgg cagctccttgt   4140 gcatagctag agccctgctc cgccactgta agattctgat tttagatgaa gccacagctg    4200
ccatggacac agagacagac ttattgatc aagagaccat ccgagaagca tttgcagact     4260
gtaccatgct gaccattgcc catcgcctgc acacggttct aggctccgat aggattatgg    4320
```

-continued

```
tgctggccca gggacaggtg gtggagtttg acaccccatc ggtccttctg tccaacgaca    4380
gttcccgatt ctatgccatg tttgctgctg cagagaacaa ggtcgctgtc aagggctgac    4440
tcctccctgt tgacgaagtc tcttttcttt agagcattgc cattccctgc ctggggcggg    4500
cccctcatcg cgtcctccta ccgaaacctt gcctttctcg attttatctt tcgcacagca    4560
gttccggatt ggcttgtgtg tttcactttt agggagagtc atattttgat tattgtattt    4620
attccatatt catgtaaaca aaatttagtt tttgttctta attgcactct aaaaggttca    4680
gggaaccgtt attataattg tatcagaggc ctataatgaa gctttatacg tgtagctata    4740
tctatatata attctgtaca tagcctatat ttacagtgaa aatgtaagct gtttatttta    4800
tattaaaata agcactgtgc taataacagt gcatattcct ttctatcatt tttgtacagt    4860
ttgctgtact agagatctgg ttttgctatt agactgtagg aagagtagca tttcattctt    4920
ctctagctgg tggtttcacg gtgccaggtt ttctgggtgt ccaaaggaag acgtgtggca    4980
atagtgggcc ctccgacagc cccctctgcc gcctccccac agccgctcca ggggtggctg    5040
gagacgggtg ggcggctgga gaccatgcag agcgccgtga gttctcaggg ctcctgcctt    5100
ctgtcctggt gtcacttact gtttctgtca ggagagcagc ggggcgaagc ccaggcccct    5160
tttcactccc tccatcaaga atggggatca cagagacatt cctccgagcc ggggagtttc    5220
tttcctgcct tcttcttttt gctgttgttt ctaaacaaga atcagtctat ccacagagag    5280
tcccactgcc tcaggttcct atggctggcc actgcacaga gctctccagc tccaagacct    5340
gttggttcca agccctggag ccaactgctg cttttttgagg tggcactttt tcatttgcct    5400
attcccacac ctccacagtt cagtggcagg gctcaggatt tcgtgggtct gttttccttt    5460
ctcaccgcag tcgtcgcaca gtctctctct ctctctcccc tcaaagtctg caactttaag    5520
cagctcttgc taatcagtgt ctcacactgg cgtagaagtt tttgtactgt aaagagacct    5580
acctcaggtt gctggttgct gtgtggtttg gtgtgttccc gcaaaccccc tttgctctgt    5640
ggggctggta gctcaggtgg gcgtggtcac tgctgtcatc agttgaatgg tcagcgttgc    5700
atgtcgtgac caactagaca ttctgtcgcc ttagcatgtt tgctgaacac cttgtggaag    5760
caaaaatctg aaaatgtgaa taaaattatt ttggattttg taaaaaaaaa aaaaaaaaa    5820 aaaaaaaaaa aaaaaaa                                                   5838
```

<210> SEQ ID NO 4
<211> LENGTH: 1437
<212> TYPE: PRT
<213> ORGANISM: Homo sapiens

<400> SEQUENCE: 4

```
Met Lys Asp Ile Asp Ile Gly Lys Glu Tyr Ile Ile Pro Ser Pro Gly
 1               5                  10                  15

Tyr Arg Ser Val Arg Glu Arg Thr Ser Thr Ser Gly Thr His Arg Asp
            20                  25                  30

Arg Glu Asp Ser Lys Phe Arg Arg Thr Arg Pro Leu Glu Cys Gln Asp
        35                  40                  45

Ala Leu Glu Thr Ala Ala Arg Ala Glu Gly Leu Ser Leu Asp Ala Ser
    50                  55                  60

Met His Ser Gln Leu Arg Ile Leu Asp Glu Glu His Pro Lys Gly Lys
65                  70                  75                  80

Tyr His His Gly Leu Ser Ala Leu Lys Pro Ile Arg Thr Thr Ser Lys
                85                  90                  95

His Gln His Pro Val Asp Asn Ala Gly Leu Phe Ser Cys Met Thr Phe
```

-continued

```
                100                 105                 110
Ser Trp Leu Ser Ser Leu Ala Arg Val Ala His Lys Lys Gly Glu Leu
            115                 120                 125
Ser Met Glu Asp Val Trp Ser Leu Ser Lys His Glu Ser Ser Asp Val
130                 135                 140
Asn Cys Arg Arg Leu Glu Arg Leu Trp Gln Glu Leu Asn Glu Val
145                 150                 155                 160
Gly Pro Asp Ala Ala Ser Leu Arg Arg Val Val Trp Ile Phe Cys Arg
                165                 170                 175
Thr Arg Leu Ile Leu Ser Ile Val Cys Leu Met Ile Thr Gln Leu Ala
                180                 185                 190
Gly Phe Ser Gly Pro Ala Phe Met Val Lys His Leu Leu Glu Tyr Thr
            195                 200                 205
Gln Ala Thr Glu Ser Asn Leu Gln Tyr Ser Leu Leu Val Leu Gly
    210                 215                 220
Leu Leu Leu Thr Glu Ile Val Arg Ser Trp Ser Leu Ala Leu Thr Trp
225                 230                 235                 240
Ala Leu Asn Tyr Arg Thr Gly Val Arg Leu Arg Gly Ala Ile Leu Thr
                245                 250                 255
Met Ala Phe Lys Lys Ile Leu Lys Leu Lys Asn Ile Lys Glu Lys Ser
            260                 265                 270
Leu Gly Glu Leu Ile Asn Ile Cys Ser Asn Asp Gly Gln Arg Met Phe
            275                 280                 285
Glu Ala Ala Val Gly Ser Leu Leu Ala Gly Gly Pro Val Val Ala
    290                 295                 300
Ile Leu Gly Met Ile Tyr Asn Val Ile Ile Leu Gly Pro Thr Gly Phe
305                 310                 315                 320
Leu Gly Ser Ala Val Phe Ile Leu Phe Tyr Pro Ala Met Met Phe Ala
                325                 330                 335
Ser Arg Leu Thr Ala Tyr Phe Arg Arg Lys Cys Val Ala Ala Thr Asp
                340                 345                 350
Glu Arg Val Gln Lys Met Asn Glu Val Leu Thr Tyr Ile Lys Phe Ile
            355                 360                 365
Lys Met Tyr Ala Trp Val Lys Ala Phe Ser Gln Ser Val Gln Lys Ile
    370                 375                 380
Arg Glu Glu Glu Arg Arg Ile Leu Glu Lys Ala Gly Tyr Phe Gln Gly
385                 390                 395                 400
Ile Thr Val Gly Val Ala Pro Ile Val Val Ile Ala Ser Val Val
                405                 410                 415
Thr Phe Ser Val His Met Thr Leu Gly Phe Asp Leu Thr Ala Ala Gln
                420                 425                 430
Ala Phe Thr Val Val Thr Val Phe Asn Ser Met Thr Phe Ala Leu Lys
            435                 440                 445
Val Thr Pro Phe Ser Val Lys Ser Leu Ser Glu Ala Ser Val Ala Val
    450                 455                 460
Asp Arg Phe Lys Ser Leu Phe Leu Met Glu Glu Val His Met Ile Lys
465                 470                 475                 480
Asn Lys Pro Ala Ser Pro His Ile Lys Ile Glu Met Lys Asn Ala Thr
                485                 490                 495
Leu Ala Trp Asp Ser Ser His Ser Ser Ile Gln Asn Ser Pro Lys Leu
                500                 505                 510
Thr Pro Lys Met Lys Lys Asp Lys Arg Ala Ser Arg Gly Lys Lys Glu
            515                 520                 525
```

-continued

```
Lys Val Arg Gln Leu Gln Arg Thr Glu His Gln Ala Val Leu Ala Glu
        530                 535                 540
Gln Lys Gly His Leu Leu Asp Ser Asp Glu Arg Pro Ser Pro Glu
545                 550                 555                 560
Glu Glu Glu Gly Lys His Ile His Leu Gly His Leu Arg Leu Gln Arg
                    565                 570                 575
Thr Leu His Ser Ile Asp Leu Glu Ile Gln Glu Gly Lys Leu Val Gly
                580                 585                 590
Ile Cys Gly Ser Val Gly Ser Gly Lys Thr Ser Leu Ile Ser Ala Ile
            595                 600                 605
Leu Gly Gln Met Thr Leu Leu Glu Gly Ser Ile Ala Ile Ser Gly Thr
        610                 615                 620
Phe Ala Tyr Val Ala Gln Gln Ala Trp Ile Leu Asn Ala Thr Leu Arg
625                 630                 635                 640
Asp Asn Ile Leu Phe Gly Lys Glu Tyr Asp Glu Glu Arg Tyr Asn Ser
                    645                 650                 655
Val Leu Asn Ser Cys Cys Leu Arg Pro Asp Leu Ala Ile Leu Pro Ser
                660                 665                 670
Ser Asp Leu Thr Glu Ile Gly Glu Arg Gly Ala Asn Leu Ser Gly Gly
            675                 680                 685
Gln Arg Gln Arg Ile Ser Leu Ala Arg Ala Leu Tyr Ser Asp Arg Ser
        690                 695                 700
Ile Tyr Ile Leu Asp Asp Pro Leu Ser Ala Leu Asp Ala His Val Gly
705                 710                 715                 720
Asn His Ile Phe Asn Ser Ala Ile Arg Lys His Leu Lys Ser Lys Thr
                    725                 730                 735
Val Leu Phe Val Thr His Gln Leu Gln Tyr Leu Val Asp Cys Asp Glu
                740                 745                 750
Val Ile Phe Met Lys Glu Gly Cys Ile Thr Glu Arg Gly Thr His Glu
            755                 760                 765
Glu Leu Met Asn Leu Asn Gly Asp Tyr Ala Thr Ile Phe Asn Asn Leu
        770                 775                 780
Leu Leu Gly Glu Thr Pro Pro Val Glu Ile Asn Ser Lys Lys Glu Thr
785                 790                 795                 800
Ser Gly Ser Gln Lys Lys Ser Gln Asp Lys Gly Pro Lys Thr Gly Ser
                    805                 810                 815
Val Lys Lys Glu Lys Ala Val Lys Pro Glu Glu Gly Gln Leu Val Gln
                820                 825                 830
Leu Glu Glu Lys Gly Gln Gly Ser Val Pro Trp Ser Val Tyr Gly Val
            835                 840                 845
Tyr Ile Gln Ala Ala Gly Gly Pro Leu Ala Phe Leu Val Ile Met Ala
        850                 855                 860
Leu Phe Met Leu Asn Val Gly Ser Thr Ala Phe Ser Thr Trp Trp Leu
865                 870                 875                 880
Ser Tyr Trp Ile Lys Gln Gly Ser Gly Asn Thr Thr Val Thr Arg Gly
                    885                 890                 895
Asn Glu Thr Ser Val Ser Asp Ser Met Lys Asp Asn Pro His Met Gln
                900                 905                 910
Tyr Tyr Ala Ser Ile Tyr Ala Leu Ser Met Ala Val Met Leu Ile Leu
            915                 920                 925
Lys Ala Ile Arg Gly Val Val Phe Val Lys Gly Thr Leu Arg Ala Ser
        930                 935                 940
```

-continued

```
Ser Arg Leu His Asp Glu Leu Phe Arg Arg Ile Leu Arg Ser Pro Met
945                 950                 955                 960

Lys Phe Phe Asp Thr Thr Pro Thr Gly Arg Ile Leu Asn Arg Phe Ser
                965                 970                 975

Lys Asp Met Asp Glu Val Asp Val Arg Leu Pro Phe Gln Ala Glu Met
            980                 985                 990

Phe Ile Gln Asn Val Ile Leu Val Phe Phe Cys Val Gly Met Ile Ala
        995                 1000                1005

Gly Val Phe Pro Trp Phe Leu Ala Val Gly Pro Leu Val Ile Leu
    1010                1015                1020

Phe Ser Val Leu His Ile Val Ser Arg Val Leu Ile Arg Glu Leu Lys
1025                1030                1035                1040

Arg Leu Asp Asn Ile Thr Gln Ser Pro Phe Leu Ser His Ile Thr Ser
                1045                1050                1055

Ser Ile Gln Gly Leu Ala Thr Ile His Ala Tyr Asn Lys Gly Gln Glu
            1060                1065                1070

Phe Leu His Arg Tyr Gln Glu Leu Leu Asp Asp Asn Gln Ala Pro Phe
        1075                1080                1085

Phe Leu Phe Thr Cys Ala Met Arg Trp Leu Ala Val Arg Leu Asp Leu
    1090                1095                1100

Ile Ser Ile Ala Leu Ile Thr Thr Thr Gly Leu Met Ile Val Leu Met
1105                1110                1115                1120

His Gly Gln Ile Pro Pro Ala Tyr Ala Gly Leu Ala Ile Ser Tyr Ala
                1125                1130                1135

Val Gln Leu Thr Gly Leu Phe Gln Phe Thr Val Arg Leu Ala Ser Glu
            1140                1145                1150

Thr Glu Ala Arg Phe Thr Ser Val Glu Arg Ile Asn His Tyr Ile Lys
        1155                1160                1165

Thr Leu Ser Leu Glu Ala Pro Ala Arg Ile Lys Asn Lys Ala Pro Ser
    1170                1175                1180

Pro Asp Trp Pro Gln Glu Gly Glu Val Thr Phe Glu Asn Ala Glu Met
1185                1190                1195                1200

Arg Tyr Arg Glu Asn Leu Pro Leu Val Leu Lys Lys Val Ser Phe Thr
                1205                1210                1215

Ile Lys Pro Lys Glu Lys Ile Gly Ile Val Gly Arg Thr Gly Ser Gly
            1220                1225                1230

Lys Ser Ser Leu Gly Met Ala Leu Phe Arg Leu Val Glu Leu Ser Gly
        1235                1240                1245

Gly Cys Ile Lys Ile Asp Gly Val Arg Ile Ser Asp Ile Gly Leu Ala
    1250                1255                1260

Asp Leu Arg Ser Lys Leu Ser Ile Ile Pro Gln Glu Pro Val Leu Phe
1265                1270                1275                1280

Ser Gly Thr Val Arg Ser Asn Leu Asp Pro Phe Asn Gln Tyr Thr Glu
                1285                1290                1295

Asp Gln Ile Trp Asp Ala Leu Glu Arg Thr His Met Lys Glu Cys Ile
            1300                1305                1310

Ala Gln Leu Pro Leu Lys Leu Glu Ser Glu Val Met Glu Asn Gly Asp
        1315                1320                1325

Asn Phe Ser Val Gly Glu Arg Gln Leu Leu Cys Ile Ala Arg Ala Leu
    1330                1335                1340

Leu Arg His Cys Lys Ile Leu Ile Leu Asp Glu Ala Thr Ala Ala Met
1345                1350                1355                1360

Asp Thr Glu Thr Asp Leu Leu Ile Gln Glu Thr Ile Arg Glu Ala Phe
```

```
                    1365              1370              1375
Ala Asp Cys Thr Met Leu Thr Ile Ala His Arg Leu His Thr Val Leu
            1380              1385              1390

Gly Ser Asp Arg Ile Met Val Leu Ala Gln Gly Gln Val Val Glu Phe
            1395              1400              1405

Asp Thr Pro Ser Val Leu Leu Ser Asn Asp Ser Arg Phe Tyr Ala
        1410              1415              1420

Met Phe Ala Ala Ala Glu Asn Lys Val Ala Val Lys Gly
1425              1430              1435

<210> SEQ ID NO 5
<211> LENGTH: 5079
<212> TYPE: DNA
<213> ORGANISM: Homo sapiens

<400> SEQUENCE: 5
```

| | | | | | |
|---|---|---|---|---|---|
| ccccatggac | gccctgtgcg | gttccgggga | gctcggctcc | aagttctggg | actccaacct | 60 |
| gtctgtgcac | acagaaaacc | cggacctcac | tccctgcttc | cagaactccc | tgctggcctg | 120 |
| ggtgccctgc | atctacctgt | gggtcgccct | gccctgctac | ttgctctacc | tgcggcacca | 180 |
| ttgtcgtggc | tacatcatcc | tctcccacct | gtccaagctc | aagatggtcc | tgggtgtcct | 240 |
| gctgtggtgt | gtcctctggg | cggacctttt | ttactcctc | catggcctgg | tccatggccg | 300 |
| ggcccctgcc | cctgttttct | tgtcaccccc | cttggtggtg | ggggtcacca | tgctgctggc | 360 |
| caccctgctg | atacagtatg | agcggctgca | gggcgtacag | tcttcggggg | tcctcattat | 420 |
| cttctggttc | ctgtgtgtgg | tctgcgccat | cgtcccattc | cgctccaaga | tccttttagc | 480 |
| caaggcagag | ggtgagatct | cagacccctt | ccgcttcacc | accttctaca | tccactttgc | 540 |
| cctggtactc | tctgccctca | tcttggcctg | cttcaggag | aaacctccat | ttttctccgc | 600 |
| aaagaatgtc | gaccctaacc | cctaccctga | gaccagcgct | ggctttctct | cccgcctgtt | 660 |
| tttctggtgg | ttcacaaaga | tggccatcta | tggctaccgg | catcccctgg | aggagaagga | 720 |
| cctctggtcc | ctaaaggaag | aggacagatc | ccagatggtg | gtgcagcagc | tgctggaggc | 780 |
| atggaggaag | caggaaaagc | agacggcacg | acacaaggct | tcagcagcac | ctgggaaaaa | 840 |
| tgcctccggc | gaggacgagg | tgctgctggg | tgcccggccc | aggccccgga | agccctcctt | 900 |
| cctgaaggcc | ctgctggcca | ccttcggctc | cagcttcctc | atcagtgcct | gcttcaagct | 960 |
| tatccaggac | ctgctctcct | tcatcaatcc | acagctgctc | agcatcctga | tcaggtttat | 1020 |
| ctccaacccc | atgccccct | cctggtgggg | cttcctggtg | gctgggctga | tgttcctgtg | 1080 |
| ctccatgatg | cagtcgctga | tcttacaaca | ctattaccac | tacatctttg | tgactgggt | 1140 |
| gaagtttcgt | actgggatca | tgggtgtcat | ctacaggaag | gctctggtta | tcaccaactc | 1200 |
| agtcaaacgt | gcgtccactg | tgggggaaat | tgtcaacctc | atgtcagtgg | atgcccagcg | 1260 |
| cttcatggac | cttgccccct | tcctcaatct | gctgtggtca | gcaccctgc | agatcatcct | 1320 |
| ggcgatctac | ttcctctggc | agaacctagg | tccctctgtc | ctggctggag | tcgctttcat | 1380 |
| ggtcttgctg | attccactca | acggagctgt | ggccgtgaa | atgcgcgcct | tccaggtaaa | 1440 |
| gcaaatgaaa | ttgaaggact | cgcgcatcaa | gctgatgagt | gagatcctga | acggcatcaa | 1500 |
| ggtgctgaag | ctgtacgcct | gggagcccag | cttcctgaag | caggtggagg | gcatcaggca | 1560 |
| gggtgagctc | cagctgctgc | gcacggcggc | ctacctccac | accacaacca | ccttcacctg | 1620 |
| gatgtgcagc | cccttcctgg | tgaccctgat | caccctctgg | gtgtacgtgt | acgtggaccc | 1680 |
| aaacaatgtg | ctggacgccg | agaaggcctt | tgtgtctgtg | tccttgtta | atatcttaag | 1740 |

```
acttcccctc aacatgctgc cccagttaat cagcaacctg actcaggcca gtgtgtctct    1800
gaaacggatc cagcaattcc tgagccaaga ggaacttgac ccccagagtg tggaaagaaa    1860
gaccatctcc ccaggctatg ccatcaccat acacagtggc accttcacct gggcccagga    1920
cctgcccccc actctgcaca gcctagacat ccaggtcccg aaaggggcac tggtggccgt    1980
ggtggggcct gtgggctgtg ggaagtcctc cctggtgtct gccctgctgg gagagatgga    2040
gaagctagaa ggcaaagtgc acatgaaggg ctccgtggcc tatgtgcccc agcaggcatg    2100
gatccagaac tgcactcttc aggaaaacgt gcttttcggc aaagccctga ccccaagcg     2160 ctaccagcag actctggagg cctgtgcctt gctagctgac ctggagatgc tgcctggtgg    2220
ggatcagaca gagattggag agaagggcat taacctgtct gggggccagc ggcagcgggt    2280
cagtctggct cgagctgttt acagtgatgc cgatattttc ttgctggatg acccactgtc    2340
cgcggtggac tctcatgtgg ccaagcacat ctttgaccac gtcatcgggc agaaggcgt    2400 gctggcaggc aagacgcgag tgctggtgac gcacggcatt agcttcctgc cccagacaga    2460
cttcatcatt gtgctagctg atggacaggt gtctgagatg ggcccgtacc cagccctgct    2520
gcagcgcaac ggctcctttg ccaactttct ctgcaactat gcccccgatg aggaccaagg    2580
gcacctggag gacagctgga ccgcgttgga aggtgcagag gataaggagg cactgctgat    2640
tgaagacaca ctcagcaacc acacggatct gacagacaat gatccagtca cctatgtggt    2700
ccagaagcag tttatgagac agctgagtgc cctgtcctca gatggggagg gacagggtcg    2760
gcctgtaccc cggaggcacc tgggtccatc agagaaggtg caggtgacag aggcgaaggc    2820
agatggggca ctgacccagg aggagaaagc agccattggc actgtggagc tcagtgtgtt    2880
ctgggattat gccaaggccg tggggctctg taccacgctg gccatctgtc tcctgtatgt    2940
gggtcaaagt gcggctgcca ttggagccaa tgtgtggctc agtgcctgga caaatgatgc    3000
catggcagac agtagacaga acaacacttc cctgaggctg gcgtctatg ctgctttagg     3060 aattctgcaa gggttcttgg tgatgctggc agccatggcc atggcagcgg gtggcatcca    3120
ggctgcccgt gtgttgcacc aggcactgct gcacaacaag atacgctcgc acagtccttt    3180
ctttgacacc acaccatcag gccgcatcct gaactgcttc tccaaggaca tctatgtcgt    3240
tgatgaggtt ctggcccctg tcatcctcat gctgctcaat tccttcttca acgccatctc    3300
cactcttgtg gtcatcatgg ccagcacgcc gctcttcact gtggtcatcc tgcccctggc    3360
tgtgctctac accttagtgc agcgcttcta tgcagccaca tcacggcaac tgaagcggct    3420
ggaatcagtc agccgctcac ctatctactc ccacttttcg gagacagtga ctggtgccag    3480
tgtcatccgg gcctacaacc gcagccggga ttttgagatc atcagtgata ctaaggtgga    3540
tgccaaccag agaagctgct acccctacat catctccaac cggtggctga gcatcggagt    3600
ggagttcgtg gggaactgcg tggtgctctt tgctgcacta tttgccgtca tcggaggag    3660 cagcctgaac ccggggctgg tgggcctttc tgtgtcctac tccttgcagg tgacatttgc    3720
tctgaactgg atgatacgaa tgatgtcaga tttggaatct aacatcgtgg ctgtggagag    3780
ggtcaaggag tactccaaga cagagacaga ggcgccctgg gtggtggaag cagccgccc    3840 tcccgaaggt tggcccccac gtggggaggt ggagttccgg aattattctg tgcgctaccg    3900
gccgggccta gacctggtgc tgagagacct gagtctgcat gtgcacggtg gcgagaaggt    3960
ggggatcgtg ggccgcactg ggctggcaa gtcttccatg acccttgcc tgttccgcat     4020 cctggaggcg gcaaagggtg aaatccgcat tgatggcctc aatgtggcag acatcggcct    4080
```

-continued

```
ccatgacctg cgctctcagc tgaccatcat cccgcaggac cccatcctgt tctcggggac    4140
cctgcgcatg aacctggacc ccttcggcag ctactcagag gaggacattt ggtgggcttt    4200
ggagctgtcc cacctgcaca cgtttgtgag ctcccagccg gcaggcctgg acttccagtg    4260
ctcagagggc ggggagaatc tcagcgtggg ccagaggcag ctcgtgtgcc tggcccgagc    4320
cctgctccgc aagagccgca tcctggtttt agacgaggcc acagctgcca tcgacctgga    4380
gactgacaac ctcatccagg ctaccatccg cacccagttt gatacctgca ctgtcctgac    4440
catcgcacac cggcttaaca ctatcatgga ctacaccagg gtcctggtcc tggacaaagg    4500
agtagtagct gaatttgatt ctccagccaa cctcattgca gctagaggca tcttctacgg    4560
gatggccaga gatgctggac ttgcctaaaa tatattcctg agatttcctc ctggcctttc    4620
ctggttttca tcaggaagga aatgacacca aatatgtccg cagaatggac ttgatagcaa    4680
acactggggg caccttaaga ttttgcacct gtaaagtgcc ttacagggta actgtgctga    4740
atgctttaga tgaggaaatg atccccaagt ggtgaatgac acgcctaagg tcacagctag    4800
tttgagccag ttagactagt ccccggtctc ccgattccca actgagtgtt atttgcacac    4860
tgcactgttt tcaaataacg attttatgaa atgacctctg tcctccctct gattttcat     4920 attttctaaa gtttcgtttc tgttttttaa taaaaagctt tttcctcctg gaacagaaga    4980
cagctgctgg gtcaggccac ccctaggaac tcagtcctgt actctggggt gctgcctgaa    5040
tccattaaaa atgggagtac tgatgaaata aaactacag                           5079
```

<210> SEQ ID NO 6
<211> LENGTH: 1527
<212> TYPE: PRT
<213> ORGANISM: Homo sapiens

<400> SEQUENCE: 6

```
Met Asp Ala Leu Cys Gly Ser Gly Glu Leu Gly Ser Lys Phe Trp Asp
 1               5                  10                  15

Ser Asn Leu Ser Val His Thr Glu Asn Pro Asp Leu Thr Pro Cys Phe
            20                  25                  30

Gln Asn Ser Leu Leu Ala Trp Val Pro Cys Ile Tyr Leu Trp Val Ala
        35                  40                  45

Leu Pro Cys Tyr Leu Leu Tyr Leu Arg His His Cys Arg Gly Tyr Ile
    50                  55                  60

Ile Leu Ser His Leu Ser Lys Leu Lys Met Val Leu Gly Val Leu Leu
65                  70                  75                  80

Trp Cys Val Ser Trp Ala Asp Leu Phe Tyr Ser Phe His Gly Leu Val
                85                  90                  95

His Gly Arg Ala Pro Ala Pro Val Phe Phe Val Thr Pro Leu Val Val
            100                 105                 110

Gly Val Thr Met Leu Leu Ala Thr Leu Leu Ile Gln Tyr Glu Arg Leu
        115                 120                 125

Gln Gly Val Gln Ser Ser Gly Val Leu Ile Ile Phe Trp Phe Leu Cys
    130                 135                 140

Val Val Cys Ala Ile Val Pro Phe Arg Ser Lys Ile Leu Leu Ala Lys
145                 150                 155                 160

Ala Glu Gly Glu Ile Ser Asp Pro Phe Arg Phe Thr Thr Phe Tyr Ile
                165                 170                 175

His Phe Ala Leu Val Leu Ser Ala Leu Ile Leu Ala Cys Phe Arg Glu
            180                 185                 190

Lys Pro Pro Phe Phe Ser Ala Lys Asn Val Asp Pro Asn Pro Tyr Pro
```

-continued

```
                195                 200                 205
Glu Thr Ser Val Gly Phe Leu Ser Arg Leu Phe Phe Trp Trp Phe Thr
210                 215                 220
Lys Met Ala Ile Tyr Gly Tyr Arg His Pro Leu Glu Lys Asp Leu
225                 230                 235                 240
Trp Ser Leu Lys Glu Glu Asp Arg Ser Gln Met Val Val Gln Gln Leu
            245                 250                 255
Leu Glu Ala Trp Arg Lys Gln Glu Lys Gln Thr Ala Arg His Lys Ala
            260                 265                 270
Ser Ala Ala Pro Gly Lys Asn Ala Ser Gly Glu Asp Glu Val Leu Leu
            275                 280                 285
Gly Ala Arg Pro Arg Pro Arg Lys Pro Ser Phe Leu Lys Ala Leu Leu
290                 295                 300
Ala Thr Phe Gly Ser Ser Phe Leu Ile Ser Ala Cys Phe Lys Leu Ile
305                 310                 315                 320
Gln Asp Leu Leu Ser Phe Ile Asn Pro Gln Leu Leu Ser Ile Leu Ile
            325                 330                 335
Arg Phe Ile Ser Asn Pro Met Ala Pro Ser Trp Trp Gly Phe Leu Val
            340                 345                 350
Ala Gly Leu Met Phe Leu Cys Ser Met Met Gln Ser Leu Ile Leu Gln
            355                 360                 365
His Tyr Tyr His Tyr Ile Phe Val Thr Gly Val Lys Phe Arg Thr Gly
            370                 375                 380
Ile Met Gly Val Ile Tyr Arg Lys Ala Leu Val Ile Thr Asn Ser Val
385                 390                 395                 400
Lys Arg Ala Ser Thr Val Gly Glu Ile Val Asn Leu Met Ser Val Asp
            405                 410                 415
Ala Gln Arg Phe Met Asp Leu Ala Pro Phe Leu Asn Leu Leu Trp Ser
            420                 425                 430
Ala Pro Leu Gln Ile Ile Leu Ala Ile Tyr Phe Leu Trp Gln Asn Leu
            435                 440                 445
Gly Pro Ser Val Leu Ala Gly Val Ala Phe Met Val Leu Leu Ile Pro
450                 455                 460
Leu Asn Gly Ala Val Ala Val Lys Met Arg Ala Phe Gln Val Lys Gln
465                 470                 475                 480
Met Lys Leu Lys Asp Ser Arg Ile Lys Leu Met Ser Glu Ile Leu Asn
            485                 490                 495
Gly Ile Lys Val Leu Lys Leu Tyr Ala Trp Glu Pro Ser Phe Leu Lys
            500                 505                 510
Gln Val Glu Gly Ile Arg Gln Gly Glu Leu Gln Leu Leu Arg Thr Ala
            515                 520                 525
Ala Tyr Leu His Thr Thr Thr Phe Thr Trp Met Cys Ser Pro Phe
530                 535                 540
Leu Val Thr Leu Ile Thr Leu Trp Val Tyr Val Tyr Val Asp Pro Asn
545                 550                 555                 560
Asn Val Leu Asp Ala Glu Lys Ala Phe Val Ser Val Ser Leu Phe Asn
            565                 570                 575
Ile Leu Arg Leu Pro Leu Asn Met Leu Pro Gln Leu Ile Ser Asn Leu
            580                 585                 590
Thr Gln Ala Ser Val Ser Leu Lys Arg Ile Gln Gln Phe Leu Ser Gln
            595                 600                 605
Glu Glu Leu Asp Pro Gln Ser Val Glu Arg Lys Thr Ile Ser Pro Gly
610                 615                 620
```

```
Tyr Ala Ile Thr Ile His Ser Gly Thr Phe Thr Trp Ala Gln Asp Leu
625                 630                 635                 640

Pro Pro Thr Leu His Ser Leu Asp Ile Gln Val Pro Lys Gly Ala Leu
            645                 650                 655

Val Ala Val Val Gly Pro Val Gly Cys Gly Lys Ser Ser Leu Val Ser
        660                 665                 670

Ala Leu Leu Gly Glu Met Glu Lys Leu Glu Gly Lys Val His Met Lys
    675                 680                 685

Gly Ser Val Ala Tyr Val Pro Gln Gln Ala Trp Ile Gln Asn Cys Thr
690                 695                 700

Leu Gln Glu Asn Val Leu Phe Gly Lys Ala Leu Asn Pro Lys Arg Tyr
705                 710                 715                 720

Gln Gln Thr Leu Glu Ala Cys Ala Leu Leu Ala Asp Leu Glu Met Leu
                725                 730                 735

Pro Gly Gly Asp Gln Thr Glu Ile Gly Glu Lys Gly Ile Asn Leu Ser
            740                 745                 750

Gly Gly Gln Arg Gln Arg Val Ser Leu Ala Arg Ala Val Tyr Ser Asp
        755                 760                 765

Ala Asp Ile Phe Leu Leu Asp Asp Pro Leu Ser Ala Val Asp Ser His
    770                 775                 780

Val Ala Lys His Ile Phe Asp His Val Ile Gly Pro Glu Gly Val Leu
785                 790                 795                 800

Ala Gly Lys Thr Arg Val Leu Val Thr His Gly Ile Ser Phe Leu Pro
                805                 810                 815

Gln Thr Asp Phe Ile Ile Val Leu Ala Asp Gly Gln Val Ser Glu Met
            820                 825                 830

Gly Pro Tyr Pro Ala Leu Leu Gln Arg Asn Gly Ser Phe Ala Asn Phe
        835                 840                 845

Leu Cys Asn Tyr Ala Pro Asp Glu Asp Gln Gly His Leu Glu Asp Ser
    850                 855                 860

Trp Thr Ala Leu Glu Gly Ala Glu Asp Lys Glu Ala Leu Leu Ile Glu
865                 870                 875                 880

Asp Thr Leu Ser Asn His Thr Asp Leu Thr Asp Asn Asp Pro Val Thr
                885                 890                 895

Tyr Val Val Gln Lys Gln Phe Met Arg Gln Leu Ser Ala Leu Ser Ser
            900                 905                 910

Asp Gly Glu Gly Gln Gly Arg Pro Val Pro Arg Arg His Leu Gly Pro
        915                 920                 925

Ser Glu Lys Val Gln Val Thr Glu Ala Lys Ala Asp Gly Ala Leu Thr
    930                 935                 940

Gln Glu Glu Lys Ala Ala Ile Gly Thr Val Glu Leu Ser Val Phe Trp
945                 950                 955                 960

Asp Tyr Ala Lys Ala Val Gly Leu Cys Thr Thr Leu Ala Ile Cys Leu
                965                 970                 975

Leu Tyr Val Gly Gln Ser Ala Ala Ile Gly Ala Asn Val Trp Leu
            980                 985                 990

Ser Ala Trp Thr Asn Asp Ala Met Ala Asp Ser Arg Gln Asn Asn Thr
        995                 1000                1005

Ser Leu Arg Leu Gly Val Tyr Ala Ala Leu Gly Ile Leu Gln Gly Phe
    1010                1015                1020

Leu Val Met Leu Ala Ala Met Ala Met Ala Ala Gly Gly Ile Gln Ala
1025                1030                1035                1040
```

-continued

Ala Arg Val Leu His Gln Ala Leu Leu His Asn Lys Ile Arg Ser Pro
            1045                1050                1055

Gln Ser Phe Phe Asp Thr Thr Pro Ser Gly Arg Ile Leu Asn Cys Phe
            1060                1065                1070

Ser Lys Asp Ile Tyr Val Val Asp Glu Val Leu Ala Pro Val Ile Leu
            1075                1080                1085

Met Leu Leu Asn Ser Phe Phe Asn Ala Ile Ser Thr Leu Val Val Ile
            1090                1095                1100

Met Ala Ser Thr Pro Leu Phe Thr Val Val Ile Leu Pro Leu Ala Val
1105            1110                1115                1120

Leu Tyr Thr Leu Val Gln Arg Phe Tyr Ala Ala Thr Ser Arg Gln Leu
            1125                1130                1135

Lys Arg Leu Glu Ser Val Ser Arg Ser Pro Ile Tyr Ser His Phe Ser
            1140                1145                1150

Glu Thr Val Thr Gly Ala Ser Val Ile Arg Ala Tyr Asn Arg Ser Arg
            1155                1160                1165

Asp Phe Glu Ile Ile Ser Asp Thr Lys Val Asp Ala Asn Gln Arg Ser
            1170                1175                1180

Cys Tyr Pro Tyr Ile Ile Ser Asn Arg Trp Leu Ser Ile Gly Val Glu
1185            1190                1195                1200

Phe Val Gly Asn Cys Val Val Leu Phe Ala Ala Leu Phe Ala Val Ile
            1205                1210                1215

Gly Arg Ser Ser Leu Asn Pro Gly Leu Val Gly Leu Ser Val Ser Tyr
            1220                1225                1230

Ser Leu Gln Val Thr Phe Ala Leu Asn Trp Met Ile Arg Met Met Ser
            1235                1240                1245

Asp Leu Glu Ser Asn Ile Val Ala Val Glu Arg Val Lys Glu Tyr Ser
            1250                1255                1260

Lys Thr Glu Thr Glu Ala Pro Trp Val Glu Gly Ser Arg Pro Pro
1265            1270                1275                1280

Glu Gly Trp Pro Pro Arg Gly Glu Val Glu Phe Arg Asn Tyr Ser Val
            1285                1290                1295

Arg Tyr Arg Pro Gly Leu Asp Leu Val Leu Arg Asp Leu Ser Leu His
            1300                1305                1310

Val His Gly Gly Glu Lys Val Gly Ile Val Gly Arg Thr Gly Ala Gly
            1315                1320                1325

Lys Ser Ser Met Thr Leu Cys Leu Phe Arg Ile Leu Glu Ala Ala Lys
            1330                1335                1340

Gly Glu Ile Arg Ile Asp Gly Leu Asn Val Ala Asp Ile Gly Leu His
1345            1350                1355                1360

Asp Leu Arg Ser Gln Leu Thr Ile Ile Pro Gln Asp Pro Ile Leu Phe
            1365                1370                1375

Ser Gly Thr Leu Arg Met Asn Leu Asp Pro Phe Gly Ser Tyr Ser Glu
            1380                1385                1390

Glu Asp Ile Trp Trp Ala Leu Glu Leu Ser His Leu His Thr Phe Val
            1395                1400                1405

Ser Ser Gln Pro Ala Gly Leu Asp Phe Gln Cys Ser Glu Gly Gly Glu
            1410                1415                1420

Asn Leu Ser Val Gly Gln Arg Gln Leu Val Cys Leu Ala Arg Ala Leu
1425            1430                1435                1440

Leu Arg Lys Ser Arg Ile Leu Val Leu Asp Glu Ala Thr Ala Ala Ile
            1445                1450                1455

Asp Leu Glu Thr Asp Asn Leu Ile Gln Ala Thr Ile Arg Thr Gln Phe

-continued

```
            1460              1465              1470
Asp Thr Cys Thr Val Leu Thr Ile Ala His Arg Leu Asn Thr Ile Met
        1475              1480              1485
Asp Tyr Thr Arg Val Leu Val Leu Asp Lys Gly Val Val Ala Glu Phe
    1490              1495              1500
Asp Ser Pro Ala Asn Leu Ile Ala Ala Arg Gly Ile Phe Tyr Gly Met
1505              1510              1515              1520
Ala Arg Asp Ala Gly Leu Ala
            1525

<210> SEQ ID NO 7
<211> LENGTH: 4509
<212> TYPE: DNA
<213> ORGANISM: Homo sapiens

<400> SEQUENCE: 7
atggccgcgc tgctgagcc ctgcgcgggg caggggtct ggaaccagac agagcctgaa      60
cctgccgcca ccagcctgct gagcctgtgc ttcctgagaa cagcaggggt ctgggtaccc     120
cccatgtacc tctgggtcct tggtcccatc tacctcctct tcatccacca ccatggccgg     180
ggctacctcc ggatgtcccc actcttcaaa gccaagatgg tgcttggatt cgccctcata     240
gtcctgtgta cctccagcgt ggctgtcgct ctttggaaaa tccaacaggg aacgcctgag     300
gccccagaat tcctcattca tcctactgtg tggctcacca cgatgagctt cgcagtgttc     360
ctgattcaca ccgagaggaa aaagggagtc cagtcatctg gagtgctgtt tggttactgg     420
cttctctgct ttgtcttgcc agctaccaac gctgcccagc aggcctccgg agcgggcttc     480
cagagcgacc ctgtccgcca cctgtccacc tacctatgcc tgtctctggt ggtggcacag     540
tttgtgctgt cctgcctggc ggatcaaccc cccttcttcc ctgaagaccc ccagcagtct     600 aaccctgtc agagactgg ggcagccttc ccctccaaag ccacgttctg gtgggttttct     660 ggcctggtct ggagggata caggaggcca ctgagaccaa aagacctctg gtcgcttggg     720
agagaaaact cctcagaaga acttgtttcc cggcttgaaa aggagtggat gaggaaccgc     780
agtgcagccc ggaggcacaa caaggcaata gcatttaaaa ggaaaggcgg cagtggcatg     840
aaggctccag agaccgagcc cttcctacgg caagaaggga gccagtggcg cccactgctg     900
aaggccatct ggcaggtgtt ccattctacc ttcctcctgg ggaccctcag cctcatcatc     960
agtgatgtct tcaggttcac tgtccccaag ctgctcagcc tttcctgga gtttattggt    1020 gatcccaagc tccagcctg aagggctac ctcctcgccg tgctgatgtt cctctcagcc    1080
tgcctgcaaa cgctgtttga gcagcagaac atgtacaggc tcaaggtgcc gcagatgagg    1140
ttgcggtcgg ccatcactgg cctggtgtac agaaaggtcc tggctctgtc cagcggctcc    1200
agaaaggcca gtgcggtggg tgatgtggtc aatctggtgt ccgtggacgt gcagcggctg    1260
accgagagcg tcctctacct caacgggctg tggctgcctc tcgtctggat cgtggtctgc    1320
ttcgtctatc tctggcagct cctggggccc tccgccctca ctgccatcgc tgtcttcctg    1380
agcctcctcc ctctgaattt cttcatctcc aagaaaagga ccaccatca ggaggagcaa    1440 atgaggcaga aggactcacg ggcacggctc accagctcta tcctcaggaa ctcgaagacc    1500
atcaagttcc atggctggga gggagccttt ctggacagag tcctgggcat ccgaggccag    1560
gagctgggcg ccttgcggac ctccggcctc tcttctctg tgtcgctggt gtccttccaa    1620
gtgtctacat ttctggtcgc actggtggtg tttgctgtcc acactctggt ggccgagaat    1680
gctatgaatg cagagaaagc ctttgtgact ctcacagttc tcaacatcct caacaaggcc    1740
```

```
caggctttcc tgcccttctc catccactcc ctcgtccagg cccgggtgtc ctttgaccgt    1800
ctggtcacct tcctctgcct ggaagaagtt gaccctggtg tcgtagactc aagttcctct    1860
ggaagcgctg ccgggaagga ttgcatcacc atacacagtg ccaccttcgc ctggtcccag    1920
gaaagccctc cctgcctcca cagaataaac ctcacggtgc cccagggctg tctgctggct    1980
gttgtcggtc cagtgggggc agggaagtcc tccctgctgt ccgccctcct tggggagctg    2040
tcaaaggtgg aggggttcgt gagcatcgag ggtgctgtgg cctacgtgcc ccaggaggcc    2100
tgggtgcaga acacctctgt ggtagagaat gtgtgcttcg ggcaggagct ggacccaccc    2160
tggctggaga gagtactaga agcctgtgcc ctgcagccag atgtggacag cttccctgag    2220
ggaatccaca cttcaattgg ggagcagggc atgaatctct ccggaggcca gaagcagcgg    2280
ctgagcctgg cccggctgt atacagaaag gcagctgtgt acctgctgga tgaccccctg    2340
gcggccctgg atgcccacgt tggccagcat gtcttcaacc aggtcattgg gcctggtggg    2400
ctactccagg gaacaacacg gattctcgtg acgcacgcac tccacatcct gccccaggct    2460
gattggatca tagtgctggc aaatgggggc atcgcagaga tgggttccta ccaggagctt    2520
ctgcagagga agggggccct cgtgtgtctt ctggatcaag ccagacagcc aggagataga    2580
ggagaaggag aaacagaacc tgggaccagc accaaggacc ccagaggcac ctctgcaggc    2640
aggaggcccg agcttagacg cgagaggtcc atcaagtcag tccctgagaa ggaccgtacc    2700
acttcagaag cccagacaga ggttcctctg gatgaccctg acagggcagg atggccagca    2760
ggaaaggaca gcatccaata cggcagggtg aaggccacag tgcacctggc ctacctgcgt    2820
gccgtgggca ccccctctg cctctacgca ctcttcctct tcctctgcca gcaagtggcc    2880
tccttctgcc ggggctactg gctgagcctg tgggcggacg accctgcagt aggtgggcag    2940
cagacgcagg cagccctgcg tggcgggatc ttcgggctcc tcggctgtct ccaagccatt    3000
gggctgtttg cctccatggc tgcggtgctc ctaggtgggg cccgggcatc caggttgctc    3060
ttccagaggc tcctgtggga tgtggtgcga tctcccatca gcttctttga gcggacaccc    3120
attggtcacc tgctaaaccg cttctccaag gagacagaca cggttgacgt ggacattcca    3180
gacaaactcc ggtccctgct gatgtacgcc tttggactcc tggaggtcag cctggtggtg    3240
gcagtggcta ccccactggc cactgtggcc atcctgccac tgtttctcct ctacgctggg    3300
tttcagagcc tgtatgtggt tagctcatgc cagctgagac gcttggagtc agccagctac    3360
tcgtctgtct gctcccacat ggctgagacg ttccagggca gcacagtggt ccgggcattc    3420
cgaacccagg cccccttgt ggctcagaac aatgctcgcg tagatgaaag ccagaggatc    3480
agtttcccgc gactggtggc tgacaggtgg cttgcggcca atgtggagct cctggggaat    3540
ggcctggtgt ttgcagccgc cacgtgtgct gtgctgagca aagcccacct cagtgctggc    3600
ctcgtgggct tctctgtctc tgctgccctc caggtgaccc agacactgca gtgggttgtt    3660
cgcaactgga cagacctaga aacagcatc gtgtcagtgg agcggatgca ggactatgcc    3720
tggacgccca aggaggctcc ctggaggctg cccacatgtg cagctcagcc ccctggcct    3780 cagggcgggc agatcgagtt ccgggacttt gggctaagat gccgacctga gctccgctg    3840 gctgtgcagg gcgtgtcctt caagatccac gcaggagaga aggtgggcat cgttggcagg    3900
accggggcag ggaagtcctc cctggccagt gggctgctgc ggctccagga ggcagctgag    3960
ggtgggatct ggatcgacgg ggtccccatt gcccacgtgg ggctgcacac actgcgctcc    4020
aggatcagca tcatccccca ggaccccatc ctgttccctg gctctctgcg gatgaacctc    4080
```

```
gacctgctgc aggagcactc ggacgaggct atctgggcag ccctggagac ggtgcagctc    4140
aaagccttgg tggccagcct gcccggccag ctgcagtaca agtgtgctga ccgaggcgag    4200
gacctgagcg tgggccagaa acagctcctg tgtctggcac gtgcccttct ccggaagacc    4260
cagatcctca tcctggacga ggctactgct gccgtggacc ctggcacgga gctgcagatg    4320
caggccatgc tcgggagctg gtttgcacag tgcactgtgc tgcccattgc ccaccgcctg    4380
cgctccgtga tggactgtgc ccgggttctg gtcatggaca aggggcaggt ggcagagagc    4440
ggcagcccgg cccagctgct ggcccagaag ggcctgtttt acagactggc ccaggagtca    4500
ggcctggtc                                                            4509

<210> SEQ ID NO 8
<211> LENGTH: 1503
<212> TYPE: PRT
<213> ORGANISM: Homo sapiens

<400> SEQUENCE: 8
```

Met Ala Ala Pro Ala Glu Pro Cys Ala Gly Gln Gly Val Trp Asn Gln
1               5                   10                  15

Thr Glu Pro Glu Pro Ala Ala Thr Ser Leu Leu Ser Leu Cys Phe Leu
            20                  25                  30

Arg Thr Ala Gly Val Trp Val Pro Pro Met Tyr Leu Trp Val Leu Gly
        35                  40                  45

Pro Ile Tyr Leu Leu Phe Ile His His Gly Arg Gly Tyr Leu Arg
    50                  55                  60

Met Ser Pro Leu Phe Lys Ala Lys Met Val Leu Gly Phe Ala Leu Ile
65                  70                  75                  80

Val Leu Cys Thr Ser Ser Val Ala Val Ala Leu Trp Lys Ile Gln Gln
                85                  90                  95

Gly Thr Pro Glu Ala Pro Glu Phe Leu Ile His Pro Thr Val Trp Leu
            100                 105                 110

Thr Thr Met Ser Phe Ala Val Phe Leu Ile His Thr Glu Arg Lys Lys
        115                 120                 125

Gly Val Gln Ser Ser Gly Val Leu Phe Gly Tyr Trp Leu Leu Cys Phe
    130                 135                 140

Val Leu Pro Ala Thr Asn Ala Ala Gln Gln Ala Ser Gly Ala Gly Phe
145                 150                 155                 160

Gln Ser Asp Pro Val Arg His Leu Ser Thr Tyr Leu Cys Leu Ser Leu
                165                 170                 175

Val Val Ala Gln Phe Val Leu Ser Cys Leu Ala Asp Gln Pro Pro Phe
            180                 185                 190

Phe Pro Glu Asp Pro Gln Gln Ser Asn Pro Cys Pro Glu Thr Gly Ala
        195                 200                 205

Ala Phe Pro Ser Lys Ala Thr Phe Trp Trp Val Ser Gly Leu Val Trp
    210                 215                 220

Arg Gly Tyr Arg Arg Pro Leu Arg Pro Lys Asp Leu Trp Ser Leu Gly
225                 230                 235                 240

Arg Glu Asn Ser Ser Glu Glu Leu Val Ser Arg Leu Glu Lys Glu Trp
                245                 250                 255

Met Arg Asn Arg Ser Ala Ala Arg His Asn Lys Ala Ile Ala Phe
            260                 265                 270

Lys Arg Lys Gly Gly Ser Gly Met Lys Ala Pro Glu Thr Glu Pro Phe
        275                 280                 285

Leu Arg Gln Glu Gly Ser Gln Trp Arg Pro Leu Leu Lys Ala Ile Trp

-continued

```
                290                 295                 300
Gln Val Phe His Ser Thr Phe Leu Leu Gly Thr Leu Ser Leu Ile Ile
305                 310                 315                 320

Ser Asp Val Phe Arg Phe Thr Val Pro Lys Leu Leu Ser Leu Phe Leu
                325                 330                 335

Glu Phe Ile Gly Asp Pro Lys Pro Pro Ala Trp Lys Gly Tyr Leu Leu
                340                 345                 350

Ala Val Leu Met Phe Leu Ser Ala Cys Leu Gln Thr Leu Phe Glu Gln
                355                 360                 365

Gln Asn Met Tyr Arg Leu Lys Val Pro Gln Met Arg Leu Arg Ser Ala
370                 375                 380

Ile Thr Gly Leu Val Tyr Arg Lys Val Leu Ala Leu Ser Ser Gly Ser
385                 390                 395                 400

Arg Lys Ala Ser Ala Val Gly Asp Val Asn Leu Val Ser Val Asp
                405                 410                 415

Val Gln Arg Leu Thr Glu Ser Val Leu Tyr Leu Asn Gly Leu Trp Leu
                420                 425                 430

Pro Leu Val Trp Ile Val Cys Phe Val Tyr Leu Trp Gln Leu Leu
                435                 440                 445

Gly Pro Ser Ala Leu Thr Ala Ile Ala Val Phe Leu Ser Leu Leu Pro
450                 455                 460

Leu Asn Phe Phe Ile Ser Lys Lys Arg Asn His His Gln Glu Glu Gln
465                 470                 475                 480

Met Arg Gln Lys Asp Ser Arg Ala Arg Leu Thr Ser Ser Ile Leu Arg
                485                 490                 495

Asn Ser Lys Thr Ile Lys Phe His Gly Trp Glu Gly Ala Phe Leu Asp
                500                 505                 510

Arg Val Leu Gly Ile Arg Gly Gln Glu Leu Gly Ala Leu Arg Thr Ser
                515                 520                 525

Gly Leu Leu Phe Ser Val Ser Leu Val Ser Phe Gln Val Ser Thr Phe
530                 535                 540

Leu Val Ala Leu Val Val Phe Ala Val His Thr Leu Val Ala Glu Asn
545                 550                 555                 560

Ala Met Asn Ala Glu Lys Ala Phe Val Thr Leu Thr Val Leu Asn Ile
                565                 570                 575

Leu Asn Lys Ala Gln Ala Phe Leu Pro Phe Ser Ile His Ser Leu Val
                580                 585                 590

Gln Ala Arg Val Ser Phe Asp Arg Leu Val Thr Phe Leu Cys Leu Glu
                595                 600                 605

Glu Val Asp Pro Gly Val Asp Ser Ser Ser Gly Ser Ala Ala
                610                 615                 620

Gly Lys Asp Cys Ile Thr Ile His Ser Ala Thr Phe Ala Trp Ser Gln
625                 630                 635                 640

Glu Ser Pro Pro Cys Leu His Arg Ile Asn Leu Thr Val Pro Gln Gly
                645                 650                 655

Cys Leu Leu Ala Val Val Gly Pro Val Gly Ala Gly Lys Ser Ser Leu
                660                 665                 670

Leu Ser Ala Leu Leu Gly Glu Leu Ser Lys Val Glu Gly Phe Val Ser
                675                 680                 685

Ile Glu Gly Ala Val Ala Tyr Val Pro Gln Glu Ala Trp Val Gln Asn
                690                 695                 700

Thr Ser Val Val Glu Asn Val Cys Phe Gly Gln Glu Leu Asp Pro Pro
705                 710                 715                 720
```

```
Trp Leu Glu Arg Val Leu Glu Ala Cys Ala Leu Gln Pro Asp Val Asp
            725                 730                 735

Ser Phe Pro Glu Gly Ile His Thr Ser Ile Gly Glu Gln Gly Met Asn
            740                 745                 750

Leu Ser Gly Gly Gln Lys Gln Arg Leu Ser Leu Ala Arg Ala Val Tyr
            755                 760                 765

Arg Lys Ala Ala Val Tyr Leu Leu Asp Asp Pro Leu Ala Ala Leu Asp
770                 775                 780

Ala His Val Gly Gln His Val Phe Asn Gln Val Ile Gly Pro Gly Gly
785                 790                 795                 800

Leu Leu Gln Gly Thr Thr Arg Ile Leu Val Thr His Ala Leu His Ile
                805                 810                 815

Leu Pro Gln Ala Asp Trp Ile Ile Val Leu Ala Asn Gly Ala Ile Ala
                820                 825                 830

Glu Met Gly Ser Tyr Gln Glu Leu Leu Gln Arg Lys Gly Ala Leu Val
                835                 840                 845

Cys Leu Leu Asp Gln Ala Arg Gln Pro Gly Asp Arg Gly Glu Gly Glu
850                 855                 860

Thr Glu Pro Gly Thr Ser Thr Lys Asp Pro Arg Gly Thr Ser Ala Gly
865                 870                 875                 880

Arg Arg Pro Glu Leu Arg Arg Glu Arg Ser Ile Lys Ser Val Pro Glu
                885                 890                 895

Lys Asp Arg Thr Thr Ser Glu Ala Gln Thr Glu Val Pro Leu Asp Asp
                900                 905                 910

Pro Asp Arg Ala Gly Trp Pro Ala Gly Lys Asp Ser Ile Gln Tyr Gly
                915                 920                 925

Arg Val Lys Ala Thr Val His Leu Ala Tyr Leu Arg Ala Val Gly Thr
            930                 935                 940

Pro Leu Cys Leu Tyr Ala Leu Phe Leu Phe Leu Cys Gln Gln Val Ala
945                 950                 955                 960

Ser Phe Cys Arg Gly Tyr Trp Leu Ser Leu Trp Ala Asp Asp Pro Ala
                965                 970                 975

Val Gly Gly Gln Gln Thr Gln Ala Ala Leu Arg Gly Gly Ile Phe Gly
            980                 985                 990

Leu Leu Gly Cys Leu Gln Ala Ile Gly Leu Phe Ala Ser Met Ala Ala
            995                 1000                1005

Val Leu Leu Gly Gly Ala Arg Ala Ser Arg Leu Leu Phe Gln Arg Leu
        1010                1015                1020

Leu Trp Asp Val Val Arg Ser Pro Ile Ser Phe Phe Glu Arg Thr Pro
1025                1030                1035                1040

Ile Gly His Leu Leu Asn Arg Phe Ser Lys Glu Thr Asp Thr Val Asp
                1045                1050                1055

Val Asp Ile Pro Asp Lys Leu Arg Ser Leu Leu Met Tyr Ala Phe Gly
                1060                1065                1070

Leu Leu Glu Val Ser Leu Val Val Ala Val Ala Thr Pro Leu Ala Thr
            1075                1080                1085

Val Ala Ile Leu Pro Leu Phe Leu Leu Tyr Ala Gly Phe Gln Ser Leu
        1090                1095                1100

Tyr Val Val Ser Ser Cys Gln Leu Arg Arg Leu Glu Ser Ala Ser Tyr
1105                1110                1115                1120

Ser Ser Val Cys Ser His Met Ala Glu Thr Phe Gln Gly Ser Thr Val
                1125                1130                1135
```

-continued

```
Val Arg Ala Phe Arg Thr Gln Ala Pro Phe Val Ala Gln Asn Asn Ala
        1140                1145                1150
Arg Val Asp Glu Ser Gln Arg Ile Ser Phe Pro Arg Leu Val Ala Asp
    1155                1160                1165
Arg Trp Leu Ala Ala Asn Val Glu Leu Leu Gly Asn Gly Leu Val Phe
1170                1175                1180
Ala Ala Ala Thr Cys Ala Val Leu Ser Lys Ala His Leu Ser Ala Gly
1185                1190                1195                1200
Leu Val Gly Phe Ser Val Ser Ala Ala Leu Gln Val Thr Gln Ala Leu
            1205                1210                1215
Gln Trp Val Val Arg Asn Trp Thr Asp Leu Glu Asn Ser Ile Val Ser
                1220                1225                1230
Val Glu Arg Met Gln Asp Tyr Ala Trp Thr Pro Lys Glu Ala Pro Trp
            1235                1240                1245
Arg Leu Pro Thr Cys Ala Ala Gln Pro Pro Trp Pro Gln Gly Gly Gln
    1250                1255                1260
Ile Glu Phe Arg Asp Phe Gly Leu Arg Tyr Arg Pro Glu Leu Pro Leu
1265                1270                1275                1280
Ala Val Gln Gly Val Ser Leu Lys Ile His Ala Gly Glu Lys Val Gly
            1285                1290                1295
Ile Val Gly Arg Thr Gly Ala Gly Lys Ser Ser Leu Ala Ser Gly Leu
        1300                1305                1310
Leu Arg Leu Gln Glu Ala Ala Glu Gly Gly Ile Trp Ile Asp Gly Val
    1315                1320                1325
Pro Ile Ala His Val Gly Leu His Thr Leu Arg Ser Arg Ile Ser Ile
    1330                1335                1340
Ile Pro Gln Asp Pro Ile Leu Phe Pro Gly Ser Leu Arg Met Asn Leu
1345                1350                1355                1360
Asp Leu Leu Gln Glu His Ser Asp Glu Ala Ile Trp Ala Ala Leu Glu
            1365                1370                1375
Thr Val Gln Leu Lys Ala Leu Val Ala Ser Leu Pro Gly Gln Leu Gln
        1380                1385                1390
Tyr Lys Cys Ala Asp Arg Gly Glu Asp Leu Ser Val Gly Gln Lys Gln
    1395                1400                1405
Leu Leu Cys Leu Ala Arg Ala Leu Leu Arg Lys Thr Gln Ile Leu Ile
1410                1415                1420
Leu Asp Glu Ala Thr Ala Ala Val Asp Pro Gly Thr Glu Leu Gln Met
1425                1430                1435                1440
Gln Ala Met Leu Gly Ser Trp Phe Ala Gln Cys Thr Val Leu Leu Ile
            1445                1450                1455
Ala His Arg Leu Arg Ser Val Met Asp Cys Ala Arg Val Leu Val Met
        1460                1465                1470
Asp Lys Gly Gln Val Ala Glu Ser Gly Ser Pro Ala Gln Leu Leu Ala
    1475                1480                1485
Gln Lys Gly Leu Phe Tyr Arg Leu Ala Gln Glu Ser Gly Leu Val
    1490                1495                1500
```

<210> SEQ ID NO 9
<211> LENGTH: 18
<212> TYPE: DNA
<213> ORGANISM: Artificial Sequence
<220> FEATURE:
<223> OTHER INFORMATION: Sequence source:/note="synthetic construct"
<220> FEATURE:
<221> NAME/KEY: misc_feature
<222> LOCATION: (3)...(15)

```
<223> OTHER INFORMATION: d = a, g or t
<220> FEATURE:
<221> NAME/KEY: misc_feature
<222> LOCATION: (18)...(18)
<223> OTHER INFORMATION: n = a, c, g or t

<400> SEQUENCE: 9
ctdgtdgcdg tdgtdggn                                              18

<210> SEQ ID NO 10
<211> LENGTH: 19
<212> TYPE: DNA
<213> ORGANISM: Artificial Sequence
<220> FEATURE:
<223> OTHER INFORMATION: Sequence source:/note="synthetic construct"

<400> SEQUENCE: 10
atggccgcgc ctgctgagc                                             19

<210> SEQ ID NO 11
<211> LENGTH: 20
<212> TYPE: DNA
<213> ORGANISM: Artificial Sequence
<220> FEATURE:
<223> OTHER INFORMATION: Sequence source:/note="synthetic construct"

<400> SEQUENCE: 11
gtctacgaca ccagggtcaa                                            20

<210> SEQ ID NO 12
<211> LENGTH: 20
<212> TYPE: DNA
<213> ORGANISM: Artificial Sequence
<220> FEATURE:
<223> OTHER INFORMATION: Sequence source:/note="synthetic construct"

<400> SEQUENCE: 12
ctgcctggaa gaagttgacc                                            20

<210> SEQ ID NO 13
<211> LENGTH: 20
<212> TYPE: DNA
<213> ORGANISM: Artificial Sequence
<220> FEATURE:
<223> OTHER INFORMATION: Sequence source:/note="synthetic construct"

<400> SEQUENCE: 13
ctggaatgtc cacgtcaacc                                            20

<210> SEQ ID NO 14
<211> LENGTH: 20
<212> TYPE: DNA
<213> ORGANISM: Artificial Sequence
<220> FEATURE:
<223> OTHER INFORMATION: Sequence source:/note="synthetic construct"

<400> SEQUENCE: 14
ggagacagac acggttgacg                                            20

<210> SEQ ID NO 15
<211> LENGTH: 19
<212> TYPE: DNA
<213> ORGANISM: Artificial Sequence
<220> FEATURE:
<223> OTHER INFORMATION: Sequence source:/note="synthetic construct"

<400> SEQUENCE: 15
```
gcagaccagg cctgactcc                                              19

<210> SEQ ID NO 16
<211> LENGTH: 24
<212> TYPE: DNA
<213> ORGANISM: Artificial Sequence
<220> FEATURE:
<223> OTHER INFORMATION: Sequence source:/note="synthetic construct"
<220> FEATURE:
<221> NAME/KEY: misc_feature
<222> LOCATION: (1)...(22)
<223> OTHER INFORMATION: r = a or g
<220> FEATURE:
<221> NAME/KEY: misc_feature
<222> LOCATION: (4)...(19)
<223> OTHER INFORMATION: n = a, c, g or t
<220> FEATURE:
<221> NAME/KEY: misc_feature
<222> LOCATION: (6)...(6)
<223> OTHER INFORMATION: v = a, c or g
<220> FEATURE:
<221> NAME/KEY: misc_feature
<222> LOCATION: (11)...(11)
<223> OTHER INFORMATION: s = c or g
<220> FEATURE:
<221> NAME/KEY: misc_feature
<222> LOCATION: (12)...(12)
<223> OTHER INFORMATION: w = a or t

<400> SEQUENCE: 16
rctnavngcn swnarnggnt crtc                                        24

<210> SEQ ID NO 17
<211> LENGTH: 29
<212> TYPE: DNA
<213> ORGANISM: Artificial Sequence
<220> FEATURE:
<223> OTHER INFORMATION: Sequence source:/note="synthetic construct"
<220> FEATURE:
<221> NAME/KEY: misc_feature
<222> LOCATION: (11)...(14)
<223> OTHER INFORMATION: r = a or g
<220> FEATURE:
<221> NAME/KEY: misc_feature
<222> LOCATION: (17)...(17)
<223> OTHER INFORMATION: y = c or t
<220> FEATURE:
<221> NAME/KEY: misc_feature
<222> LOCATION: (20)...(20)
<223> OTHER INFORMATION: h = a, c or t
<220> FEATURE:
<221> NAME/KEY: misc_feature
<222> LOCATION: (23)...(29)
<223> OTHER INFORMATION: n = a, c, g or t

<400> SEQUENCE: 17
cgggatccag rgaraayath ctntttggn                                   29

<210> SEQ ID NO 18
<211> LENGTH: 29
<212> TYPE: DNA
<213> ORGANISM: Artificial Sequence
<220> FEATURE:
<223> OTHER INFORMATION: Sequence source:/note="synthetic construct"
<220> FEATURE:
<221> NAME/KEY: misc_feature
<222> LOCATION: (9)...(18)
<223> OTHER INFORMATION: n = a, c, g or t
<220> FEATURE:
<221> NAME/KEY: misc_feature
<222> LOCATION: (12)...(27)
<223> OTHER INFORMATION: r = a or g
<220> FEATURE:

```
<221> NAME/KEY: misc_feature
<222> LOCATION: (15)...(15)
<223> OTHER INFORMATION: h = a, c or t
<220> FEATURE:
<221> NAME/KEY: misc_feature
<222> LOCATION: (24)...(24)
<223> OTHER INFORMATION: d = a, g or t

<400> SEQUENCE: 18
cggaattcnt crtchagnag rtadatrtc                                     29

<210> SEQ ID NO 19
<211> LENGTH: 1531
<212> TYPE: PRT
<213> ORGANISM: Homo Sapiens

<400> SEQUENCE: 19
```

| | | | | | | | | | | | | | | |
|---|---|---|---|---|---|---|---|---|---|---|---|---|---|---|
| Met | Ala | Leu | Arg | Gly | Phe | Cys | Ser | Ala | Asp | Gly | Ser | Asp | Pro | Leu | Trp |
| 1 | | | | 5 | | | | | 10 | | | | | 15 | |
| Asp | Trp | Asn | Val | Thr | Trp | Asn | Thr | Ser | Asn | Pro | Asp | Phe | Thr | Lys | Cys |
| | | | 20 | | | | | 25 | | | | | 30 | | |
| Phe | Gln | Asn | Thr | Val | Leu | Val | Trp | Val | Pro | Cys | Phe | Tyr | Leu | Trp | Ala |
| | | | 35 | | | | | 40 | | | | | 45 | | |
| Cys | Phe | Pro | Phe | Tyr | Phe | Leu | Tyr | Leu | Ser | Arg | His | Asp | Arg | Gly | Tyr |
| | 50 | | | | | 55 | | | | | 60 | | | | |
| Ile | Gln | Met | Thr | Pro | Leu | Asn | Lys | Thr | Lys | Thr | Ala | Leu | Gly | Phe | Leu |
| 65 | | | | | 70 | | | | | 75 | | | | | 80 |
| Leu | Trp | Ile | Val | Cys | Trp | Ala | Asp | Leu | Phe | Tyr | Ser | Phe | Trp | Glu | Arg |
| | | | | 85 | | | | | 90 | | | | | 95 | |
| Ser | Arg | Gly | Ile | Phe | Leu | Ala | Pro | Val | Phe | Leu | Val | Ser | Pro | Thr | Leu |
| | | | 100 | | | | | 105 | | | | | 110 | | |
| Leu | Gly | Ile | Thr | Thr | Leu | Leu | Ala | Thr | Phe | Leu | Ile | Gln | Leu | Glu | Arg |
| | | | 115 | | | | | 120 | | | | | 125 | | |
| Arg | Lys | Gly | Val | Gln | Ser | Ser | Gly | Ile | Met | Leu | Thr | Phe | Trp | Leu | Val |
| | 130 | | | | | 135 | | | | | 140 | | | | |
| Ala | Leu | Val | Cys | Ala | Leu | Ala | Ile | Leu | Arg | Ser | Lys | Ile | Met | Thr | Ala |
| 145 | | | | | 150 | | | | | 155 | | | | | 160 |
| Leu | Lys | Glu | Asp | Ala | Gln | Val | Asp | Leu | Phe | Arg | Asp | Ile | Thr | Phe | Tyr |
| | | | | 165 | | | | | 170 | | | | | 175 | |
| Val | Tyr | Phe | Ser | Leu | Leu | Leu | Ile | Gln | Leu | Val | Leu | Ser | Cys | Phe | Ser |
| | | | 180 | | | | | 185 | | | | | 190 | | |
| Asp | Arg | Ser | Pro | Leu | Phe | Ser | Glu | Thr | Ile | His | Asp | Pro | Asn | Pro | Cys |
| | | | 195 | | | | | 200 | | | | | 205 | | |
| Pro | Glu | Ser | Ser | Ala | Ser | Phe | Leu | Ser | Arg | Ile | Thr | Phe | Trp | Trp | Ile |
| | 210 | | | | | 215 | | | | | 220 | | | | |
| Thr | Gly | Leu | Ile | Val | Arg | Gly | Tyr | Arg | Gln | Pro | Leu | Glu | Gly | Ser | Asp |
| 225 | | | | | 230 | | | | | 235 | | | | | 240 |
| Leu | Trp | Ser | Leu | Asn | Lys | Glu | Asp | Thr | Ser | Glu | Gln | Val | Val | Pro | Val |
| | | | | 245 | | | | | 250 | | | | | 255 | |
| Leu | Val | Lys | Asn | Trp | Lys | Lys | Glu | Cys | Ala | Lys | Thr | Arg | Lys | Gln | Pro |
| | | | 260 | | | | | 265 | | | | | 270 | | |
| Val | Lys | Val | Tyr | Ser | Ser | Lys | Asp | Pro | Ala | Gln | Pro | Lys | Glu | Ser | |
| | | | 275 | | | | | 280 | | | | | 285 | | |
| Ser | Lys | Val | Asp | Ala | Asn | Glu | Glu | Val | Glu | Ala | Leu | Ile | Val | Lys | Ser |
| | 290 | | | | | 295 | | | | | 300 | | | | |
| Pro | Gln | Lys | Glu | Trp | Asn | Pro | Ser | Leu | Phe | Lys | Val | Leu | Tyr | Lys | Thr |
| 305 | | | | | 310 | | | | | 315 | | | | | 320 |

```
Phe Gly Pro Tyr Phe Leu Met Ser Phe Phe Lys Ala Ile His Asp
            325                 330                 335

Leu Met Met Phe Ser Gly Pro Gln Ile Leu Lys Leu Leu Ile Lys Phe
        340                 345                 350

Val Asn Asp Thr Lys Ala Pro Asp Trp Gln Gly Tyr Phe Tyr Thr Val
        355                 360                 365

Leu Leu Phe Val Thr Ala Cys Leu Gln Thr Leu Val Leu His Gln Tyr
    370                 375                 380

Phe His Ile Cys Phe Val Ser Gly Met Arg Ile Lys Thr Ala Val Ile
385                 390                 395                 400

Gly Ala Val Tyr Arg Lys Ala Leu Val Ile Thr Asn Ser Ala Arg Lys
                405                 410                 415

Ser Ser Thr Val Gly Glu Ile Val Asn Leu Met Ser Val Asp Ala Gln
                420                 425                 430

Arg Phe Met Asp Leu Ala Thr Tyr Ile Asn Met Ile Trp Ser Ala Pro
            435                 440                 445

Leu Gln Val Ile Leu Ala Leu Tyr Leu Leu Trp Leu Asn Leu Gly Pro
        450                 455                 460

Ser Val Leu Ala Gly Val Ala Val Met Val Leu Met Val Pro Val Asn
465                 470                 475                 480

Ala Val Met Ala Met Lys Thr Lys Thr Tyr Gln Val Ala His Met Lys
                485                 490                 495

Ser Lys Asp Asn Arg Ile Lys Leu Met Asn Glu Ile Leu Asn Gly Ile
                500                 505                 510

Lys Val Leu Lys Leu Tyr Ala Trp Glu Leu Ala Phe Lys Asp Lys Val
            515                 520                 525

Leu Ala Ile Arg Gln Glu Glu Leu Lys Val Leu Lys Lys Ser Ala Tyr
        530                 535                 540

Leu Ser Ala Val Gly Thr Phe Thr Trp Val Cys Thr Pro Phe Leu Val
545                 550                 555                 560

Ala Leu Cys Thr Phe Ala Val Tyr Val Thr Ile Asp Glu Asn Asn Ile
                565                 570                 575

Leu Asp Ala Gln Thr Ala Phe Val Ser Leu Ala Leu Phe Asn Ile Leu
            580                 585                 590

Arg Phe Pro Leu Asn Ile Leu Pro Met Val Ile Ser Ser Ile Val Gln
        595                 600                 605

Ala Ser Val Ser Leu Lys Arg Leu Arg Ile Phe Leu Ser His Glu Glu
    610                 615                 620

Leu Glu Pro Asp Ser Ile Glu Arg Arg Pro Val Lys Asp Gly Gly Gly
625                 630                 635                 640

Thr Asn Ser Ile Thr Val Arg Asn Ala Thr Phe Thr Trp Ala Arg Ser
                645                 650                 655

Asp Pro Pro Thr Leu Asn Gly Ile Thr Phe Ser Ile Pro Glu Gly Ala
            660                 665                 670

Leu Val Ala Val Val Gly Gln Val Gly Cys Gly Lys Ser Ser Leu Leu
        675                 680                 685

Ser Ala Leu Leu Ala Glu Met Asp Lys Val Glu Gly His Val Ala Ile
    690                 695                 700

Lys Gly Ser Val Ala Tyr Val Pro Gln Gln Ala Trp Ile Gln Asn Asp
705                 710                 715                 720

Ser Leu Arg Glu Asn Ile Leu Phe Gly Cys Gln Leu Glu Glu Pro Tyr
                725                 730                 735
```

-continued

```
Tyr Arg Ser Val Ile Gln Ala Cys Ala Leu Leu Pro Asp Leu Glu Ile
                740                 745                 750

Leu Pro Ser Gly Asp Arg Thr Glu Ile Gly Glu Lys Gly Val Asn Leu
            755                 760                 765

Ser Gly Gly Gln Lys Gln Arg Val Ser Leu Ala Arg Ala Val Tyr Ser
770                 775                 780

Asn Ala Asp Ile Tyr Leu Phe Asp Asp Pro Leu Ser Ala Val Asp Ala
785                 790                 795                 800

His Val Gly Lys His Ile Phe Glu Asn Val Ile Gly Pro Lys Gly Met
                805                 810                 815

Leu Lys Asn Lys Thr Arg Ile Leu Val Thr His Ser Met Ser Tyr Leu
                820                 825                 830

Pro Gln Val Asp Val Ile Ile Val Met Ser Gly Gly Lys Ile Ser Glu
            835                 840                 845

Met Gly Ser Tyr Gln Glu Leu Leu Ala Arg Asp Gly Ala Phe Ala Glu
850                 855                 860

Phe Leu Arg Thr Tyr Ala Ser Thr Glu Gln Glu Gln Asp Ala Glu Glu
865                 870                 875                 880

Asn Gly Val Thr Gly Val Ser Gly Pro Gly Lys Glu Ala Lys Gln Met
                885                 890                 895

Glu Asn Gly Met Leu Val Thr Asp Ser Ala Gly Lys Gln Leu Gln Arg
                900                 905                 910

Gln Leu Ser Ser Ser Ser Ser Tyr Ser Gly Asp Ile Ser Arg His His
            915                 920                 925

Asn Ser Thr Ala Glu Leu Gln Lys Ala Glu Ala Lys Lys Glu Glu Thr
            930                 935                 940

Trp Lys Leu Met Glu Ala Asp Lys Ala Gln Thr Gly Gln Val Lys Leu
945                 950                 955                 960

Ser Val Tyr Trp Asp Tyr Met Lys Ala Ile Gly Leu Phe Ile Ser Phe
                965                 970                 975

Leu Ser Ile Phe Leu Phe Met Cys Asn His Val Ser Ala Leu Ala Ser
            980                 985                 990

Asn Tyr Trp Leu Ser Leu Trp Thr Asp Asp Pro Ile Val Asn Gly Thr
            995                 1000                1005

Gln Glu His Thr Lys Val Arg Leu Ser Val Tyr Gly Ala Leu Gly Ile
    1010                1015                1020

Ser Gln Gly Ile Ala Val Phe Gly Tyr Ser Met Ala Val Ser Ile Gly
1025                1030                1035                1040

Gly Ile Leu Ala Ser Arg Cys Leu His Val Asp Leu Leu His Ser Ile
                1045                1050                1055

Leu Arg Ser Pro Met Ser Phe Phe Glu Arg Thr Pro Ser Gly Asn Leu
                1060                1065                1070

Val Asn Arg Phe Ser Lys Glu Leu Asp Thr Val Asp Ser Met Ile Pro
                1075                1080                1085

Glu Val Ile Lys Met Phe Met Gly Ser Leu Phe Asn Val Ile Gly Ala
                1090                1095                1100

Cys Ile Val Ile Leu Ala Thr Pro Ile Ala Ile Ile Ile Pro
1105                1110                1115                1120

Pro Leu Gly Leu Ile Tyr Phe Phe Val Gln Arg Phe Tyr Val Ala Ser
                1125                1130                1135

Ser Arg Gln Leu Lys Arg Leu Glu Ser Val Ser Arg Ser Pro Val Tyr
                1140                1145                1150

Ser His Phe Asn Glu Thr Leu Leu Gly Val Ser Val Ile Arg Ala Phe
```

```
                   1155                1160                1165
Glu Glu Gln Glu Arg Phe Ile His Gln Ser Asp Leu Lys Val Asp Glu
    1170                1175                1180

Asn Gln Lys Ala Tyr Tyr Pro Ser Ile Val Ala Asn Arg Trp Leu Ala
1185                1190                1195                1200

Val Arg Leu Glu Cys Val Gly Asn Cys Ile Val Leu Phe Ala Ala Leu
            1205                1210                1215

Phe Ala Val Ile Ser Arg His Ser Leu Ser Ala Gly Leu Val Gly Leu
            1220                1225                1230

Ser Val Ser Tyr Ser Leu Gln Val Thr Thr Tyr Leu Asn Trp Leu Val
            1235                1240                1245

Arg Met Ser Ser Glu Met Glu Thr Asn Ile Val Ala Val Glu Arg Leu
            1250                1255                1260

Lys Glu Tyr Ser Glu Thr Glu Lys Glu Ala Pro Trp Gln Ile Gln Glu
1265                1270                1275                1280

Thr Ala Pro Pro Ser Ser Trp Pro Gln Val Gly Arg Val Glu Phe Arg
            1285                1290                1295

Asn Tyr Cys Leu Arg Tyr Arg Glu Asp Leu Asp Phe Val Leu Arg His
            1300                1305                1310

Ile Asn Val Thr Ile Asn Gly Gly Glu Lys Val Gly Ile Val Gly Arg
            1315                1320                1325

Thr Gly Ala Gly Lys Ser Ser Leu Thr Leu Gly Leu Phe Arg Ile Asn
            1330                1335                1340

Glu Ser Ala Glu Gly Glu Ile Ile Ile Asp Gly Ile Asn Ile Ala Lys
1345                1350                1355                1360

Ile Gly Leu His Asp Leu Arg Phe Lys Ile Thr Ile Ile Pro Gln Asp
            1365                1370                1375

Pro Val Leu Phe Ser Gly Ser Leu Arg Met Asn Leu Asp Pro Phe Ser
            1380                1385                1390

Gln Tyr Ser Asp Glu Glu Val Trp Thr Ser Leu Glu Leu Ala His Leu
            1395                1400                1405

Lys Asp Phe Val Ser Ala Leu Pro Asp Lys Leu Asp His Glu Cys Ala
    1410                1415                1420

Glu Gly Gly Glu Asn Leu Ser Val Gly Gln Arg Gln Leu Val Cys Leu
1425                1430                1435                1440

Ala Arg Ala Leu Leu Arg Lys Thr Lys Ile Leu Val Leu Asp Glu Ala
            1445                1450                1455

Thr Ala Ala Val Asp Leu Glu Thr Asp Asp Leu Ile Gln Ser Thr Ile
            1460                1465                1470

Arg Thr Gln Phe Glu Asp Cys Thr Val Leu Thr Ile Ala His Arg Leu
            1475                1480                1485

Asn Thr Ile Met Asp Tyr Thr Arg Val Ile Val Leu Asp Lys Gly Glu
            1490                1495                1500

Ile Gln Glu Tyr Gly Ala Pro Ser Asp Leu Leu Gln Gln Arg Gly Leu
1505                1510                1515                1520

Phe Tyr Ser Met Ala Lys Asp Ala Gly Leu Val
            1525                1530

<210> SEQ ID NO 20
<211> LENGTH: 12
<212> TYPE: PRT
<213> ORGANISM: Artificial Sequence
<220> FEATURE:
<223> OTHER INFORMATION: Synthetic Sequence
```

<400> SEQUENCE: 20

Ile Leu Gln Lys Lys Leu Ser Thr Tyr Trp Ser His
1               5                   10

<210> SEQ ID NO 21
<211> LENGTH: 150
<212> TYPE: PRT
<213> ORGANISM: Saccharomyces cerevisiae

<400> SEQUENCE: 21

Leu Lys Asn Ile Asn Phe Gln Ala Lys Lys Gly Asn Leu Thr Cys Ile
1               5                   10                  15

Val Gly Lys Val Gly Ser Gly Lys Thr Ala Leu Leu Ser Cys Met Leu
            20                  25                  30

Gly Asp Leu Phe Arg Val Lys Gly Phe Ala Thr Val His Gly Ser Val
        35                  40                  45

Ala Tyr Val Ser Gln Val Pro Trp Ile Met Asn Gly Thr Val Lys Glu
    50                  55                  60

Asn Ile Leu Phe Gly His Arg Tyr Asp Ala Glu Phe Tyr Glu Lys Thr
65                  70                  75                  80

Ile Lys Ala Cys Ala Leu Thr Ile Asp Leu Ala Ile Leu Met Asp Gly
                85                  90                  95

Asp Lys Thr Leu Val Gly Glu Lys Gly Ile Ser Leu Ser Gly Gly Gln
            100                 105                 110

Lys Ala Arg Leu Ser Leu Ala Arg Ala Val Tyr Ala Arg Ala Asp Thr
        115                 120                 125

Tyr Leu Leu Asp Asp Pro Leu Ala Ala Val Asp Glu His Val Ala Arg
    130                 135                 140

His Leu Ile Glu His Val
145                 150

<210> SEQ ID NO 22
<211> LENGTH: 161
<212> TYPE: PRT
<213> ORGANISM: Saccharomyces cerevisiae

<400> SEQUENCE: 22

Leu Lys His Ile Asn Ile His Ile Lys Pro Asn Glu Lys Val Gly Ile
1               5                   10                  15

Val Gly Arg Thr Gly Ala Gly Lys Ser Ser Leu Thr Leu Ala Leu Phe
            20                  25                  30

Arg Met Ile Glu Ala Ser Glu Gly Asn Ile Val Ile Asp Asn Ile Ala
        35                  40                  45

Ile Asn Glu Ile Gly Leu Tyr Asp Leu Arg His Lys Leu Ser Ile Ile
    50                  55                  60

Pro Gln Asp Ser Gln Val Phe Glu Gly Thr Val Arg Glu Asn Ile Asp
65                  70                  75                  80

Pro Ile Asn Gln Tyr Thr Asp Glu Ala Ile Trp Arg Ala Leu Glu Leu
                85                  90                  95

Ser His Leu Lys Glu His Val Leu Ser Met Ser Asn Asp Gly Leu Asp
            100                 105                 110

Ala Gln Leu Thr Glu Gly Gly Gly Asn Leu Ser Val Gly Gln Arg Gln
        115                 120                 125

Leu Leu Cys Leu Ala Arg Ala Met Leu Val Pro Ser Lys Ile Leu Val
    130                 135                 140

Leu Asp Glu Ala Thr Ala Ala Val Asp Val Glu Thr Asp Lys Val Val 145                 150                 155                 160

Gln

<210> SEQ ID NO 23
<211> LENGTH: 150
<212> TYPE: PRT
<213> ORGANISM: Homo Sapiens

<400> SEQUENCE: 23

Val Arg Asp Val Asn Leu Asp Ile Met Ala Gly Gln Leu Val Ala Val
1               5                   10                  15

Ile Gly Pro Val Gly Ser Gly Lys Ser Ser Leu Ile Ser Ala Met Leu
            20                  25                  30

Gly Glu Met Glu Asn Val His Gly His Ile Thr Ile Lys Gly Thr Thr
        35                  40                  45

Ala Tyr Val Pro Gln Gln Ser Trp Ile Gln Asn Gly Thr Ile Lys Asp
    50                  55                  60

Asn Ile Leu Phe Gly Thr Glu Phe Asn Glu Lys Arg Tyr Gln Gln Val
65                  70                  75                  80

Leu Glu Ala Cys Ala Leu Leu Pro Asp Leu Glu Met Leu Pro Gly Gly
                85                  90                  95

Asp Leu Ala Glu Ile Gly Glu Lys Gly Ile Asn Leu Ser Gly Gly Gln
            100                 105                 110

Lys Gln Arg Ile Ser Leu Ala Arg Ala Thr Tyr Gln Asn Leu Asp Ile
        115                 120                 125

Tyr Leu Leu Asp Asp Pro Leu Ser Ala Val Asp Ala His Val Gly Lys
    130                 135                 140

His Ile Phe Asn Lys Val
145                 150

<210> SEQ ID NO 24
<211> LENGTH: 160
<212> TYPE: PRT
<213> ORGANISM: Homo Sapiens

<400> SEQUENCE: 24

Leu Arg Gly Ile Thr Cys Asp Ile Gly Ser Met Glu Lys Ile Gly Val
1               5                   10                  15

Val Gly Arg Thr Gly Ala Gly Lys Ser Ser Leu Thr Asn Cys Leu Phe
            20                  25                  30

Arg Ile Leu Glu Ala Ala Gly Gly Gln Ile Ile Ile Asp Gly Val Asp
        35                  40                  45

Ile Ala Ser Ile Gly Leu His Asp Leu Arg Glu Lys Leu Thr Ile Ile
    50                  55                  60

Pro Gln Asp Pro Ile Leu Phe Ser Gly Ser Leu Arg Met Asn Leu Asp
65                  70                  75                  80

Pro Phe Asn Asn Tyr Ser Asp Glu Glu Ile Trp Lys Ala Leu Glu Leu
                85                  90                  95

Ala His Leu Lys Ser Phe Val Ala Ser Leu Gln Leu Gly Leu Ser His
            100                 105                 110

Glu Val Thr Glu Ala Gly Gly Asn Leu Ser Ile Gly Gln Arg Gln Leu
        115                 120                 125

Leu Cys Leu Gly Arg Ala Leu Leu Arg Lys Ser Lys Ile Leu Val Leu
    130                 135                 140

Asp Glu Ala Thr Ala Ala Val Asp Leu Glu Thr Asp Asn Leu Ile Gln
145                 150                 155                 160

```
<210> SEQ ID NO 25
<211> LENGTH: 150
<212> TYPE: PRT
<213> ORGANISM: Homo Sapiens

<400> SEQUENCE: 25

Leu Lys Asp Ile Asn Phe Lys Ile Glu Arg Gly Gln Leu Leu Ala Val
 1               5                  10                  15

Ala Gly Ser Thr Gly Ala Gly Lys Thr Ser Leu Leu Met Met Ile Met
            20                  25                  30

Gly Glu Leu Glu Pro Ser Glu Gly Lys Ile Lys His Ser Gly Arg Ile
        35                  40                  45

Ser Phe Cys Ser Gln Phe Ser Trp Ile Met Pro Gly Thr Ile Lys Glu
    50                  55                  60

Asn Ile Ile Phe Gly Val Ser Tyr Asp Glu Tyr Arg Tyr Arg Ser Val
65                  70                  75                  80

Ile Lys Ala Cys Gln Leu Glu Asp Ile Ser Lys Phe Ala Glu Lys
                85                  90                  95

Asp Asn Ile Val Leu Gly Glu Gly Ile Thr Leu Ser Gly Gly Gln
                100                 105                 110

Arg Ala Arg Ile Ser Leu Ala Arg Ala Val Tyr Lys Asp Ala Asp Leu
                115                 120                 125

Tyr Leu Leu Asp Ser Pro Phe Gly Tyr Leu Asp Val Leu Thr Glu Lys
    130                 135                 140

Glu Ile Phe Glu Ser Cys
145                 150

<210> SEQ ID NO 26
<211> LENGTH: 159
<212> TYPE: PRT
<213> ORGANISM: Homo Sapiens

<400> SEQUENCE: 26

Leu Glu Asn Ile Ser Phe Ser Ile Ser Pro Gly Gln Arg Val Gly Leu
 1               5                  10                  15

Leu Gly Arg Thr Gly Ser Gly Lys Ser Thr Leu Leu Ser Ala Phe Leu
            20                  25                  30

Arg Leu Leu Asn Thr Glu Gly Glu Ile Gln Ile Asp Gly Val Ser Trp
        35                  40                  45

Asp Ser Ile Thr Leu Gln Gln Trp Arg Lys Ala Phe Gly Val Ile Pro
    50                  55                  60

Gln Lys Val Phe Ile Phe Ser Gly Thr Phe Arg Lys Asn Leu Asp Pro
65                  70                  75                  80

Tyr Glu Gln Trp Ser Asp Gln Glu Ile Trp Lys Val Ala Asp Glu Val
                85                  90                  95

Gly Leu Arg Ser Val Ile Glu Gln Phe Pro Gly Lys Leu Asp Phe Val
                100                 105                 110

Leu Val Asp Gly Gly Cys Val Leu Ser His Gly His Lys Gln Leu Met
                115                 120                 125

Cys Leu Ala Arg Ser Val Leu Ser Lys Ala Lys Ile Leu Leu Leu Asp
                130                 135                 140

Glu Pro Ser Ala His Leu Asp Pro Val Thr Tyr Gln Ile Ile Arg
145                 150                 155

<210> SEQ ID NO 27
```

```
<211> LENGTH: 150
<212> TYPE: PRT
<213> ORGANISM: Leishmania tarentolae

<400> SEQUENCE: 27

Leu Arg Asn Val Ser Leu Thr Ile Pro Lys Gly Lys Leu Thr Met Val
 1               5                  10                  15

Ile Gly Ser Thr Gly Ser Gly Lys Ser Thr Leu Leu Gly Ala Leu Met
             20                  25                  30

Gly Glu Tyr Ser Val Glu Ser Gly Glu Leu Trp Ala Glu Arg Ser Ile
         35                  40                  45

Ala Tyr Val Pro Gln Gln Ala Trp Ile Met Asn Ala Thr Leu Arg Gly
 50                  55                  60

Asn Ile Leu Phe Phe Asp Glu Glu Arg Ala Glu Asp Leu Gln Asp Val
 65                  70                  75                  80

Ile Arg Cys Cys Gln Leu Glu Ala Asp Leu Ala Gln Phe Cys Gly Gly
                 85                  90                  95

Leu Asp Thr Glu Ile Gly Glu Met Gly Val Asn Leu Ser Gly Gly Gln
            100                 105                 110

Lys Ala Arg Val Ser Leu Ala Arg Ala Val Tyr Ala Asn Arg Asp Val
        115                 120                 125

Tyr Leu Leu Asp Asp Pro Leu Ser Ala Leu Asp Ala His Val Gly Gln
130                 135                 140

Arg Ile Val Gln Asp Val
145                 150

<210> SEQ ID NO 28
<211> LENGTH: 161
<212> TYPE: PRT
<213> ORGANISM: Leishmania tarentolae

<400> SEQUENCE: 28

Leu Arg Gly Val Ser Phe Gln Ile Ala Pro Arg Glu Lys Val Gly Ile
 1               5                  10                  15

Val Gly Arg Thr Gly Ser Gly Lys Ser Thr Leu Leu Leu Thr Phe Met
             20                  25                  30

Arg Met Val Glu Val Cys Gly Gly Val Ile His Val Asn Gly Arg Glu
         35                  40                  45

Met Ser Ala Tyr Gly Leu Arg Asp Val Arg Arg His Phe Ser Met Ile
 50                  55                  60

Pro Gln Asp Pro Val Leu Phe Asp Gly Thr Val Arg Gln Asn Val Asp
 65                  70                  75                  80

Pro Phe Leu Glu Ala Ser Ser Ala Glu Val Trp Ala Ala Leu Glu Leu
                 85                  90                  95

Val Gly Leu Arg Glu Arg Val Ala Ser Glu Ser Gly Ile Asp Ser
            100                 105                 110

Arg Val Leu Glu Gly Gly Ser Asn Tyr Ser Val Gly Gln Arg Gln Leu
        115                 120                 125

Met Cys Met Ala Arg Ala Leu Leu Lys Arg Gly Ser Gly Phe Ile Leu
130                 135                 140

Met Asp Glu Ala Thr Ala Asn Ile Asp Pro Ala Leu Asp Arg Gln Ile
145                 150                 155                 160

Gln

<210> SEQ ID NO 29
<211> LENGTH: 176
```

```
<212> TYPE: PRT
<213> ORGANISM: Homo Sapiens

<400> SEQUENCE: 29

Leu Ser Asn Ile Thr Ile Arg Ile Pro Arg Gly Gln Leu Thr Met Ile
1               5                   10                  15

Val Gly Gln Val Gly Cys Gly Lys Ser Ser Leu Leu Ala Ala Leu
            20                  25                  30

Gly Glu Met Gln Lys Val Ser Gly Ala Val Phe Trp Ser Ser Leu Pro
            35                  40                  45

Asp Ser Glu Ile Gly Glu Asp Pro Ser Pro Arg Glu Thr Ala Thr
        50                  55                  60

Asp Leu Asp Ile Arg Lys Arg Gly Pro Val Ala Tyr Ala Ser Gln Lys
65                  70                  75                  80

Pro Trp Leu Leu Asn Ala Thr Val Glu Glu Asn Ile Thr Phe Glu Ser
                85                  90                  95

Pro Phe Asn Lys Gln Arg Tyr Lys Met Val Ile Glu Ala Cys Ser Leu
                100                 105                 110

Gln Pro Asp Ile Asp Ile Leu Pro His Gly Asp Gln Thr Gln Ile Gly
            115                 120                 125

Glu Arg Gly Ile Asn Leu Ser Gly Gly Gln Arg Gln Arg Ile Ser Val
    130                 135                 140

Ala Arg Arg Leu Tyr Gln His Ala Asn Val Val Phe Leu Asp Asp Pro
145                 150                 155                 160

Phe Ser Ala Asp Val His Leu Ser Asp His Leu Met Gln Ala Gly
                165                 170                 175

<210> SEQ ID NO 30
<211> LENGTH: 160
<212> TYPE: PRT
<213> ORGANISM: Homo Sapiens

<400> SEQUENCE: 30

Leu Lys His Val Asn Ala Leu Ile Ser Pro Gly Gln Lys Ile Gly Ile
1               5                   10                  15

Cys Gly Arg Thr Gly Ser Gly Lys Ser Ser Phe Ser Leu Ala Phe Phe
            20                  25                  30

Arg Met Val Asp Thr Phe Glu Gly His Ile Ile Ile Asp Gly Ile Asp
            35                  40                  45

Ile Arg Lys Leu Pro Leu His Thr Leu Pro Ser Arg Leu Ser Ile Ile
    50                  55                  60

Leu Gln Asp Pro Val Leu Phe Ser Gly Thr Ile Arg Phe Asn Leu Asp
65                  70                  75                  80

Pro Glu Lys Lys Cys Ser Asp Ser Thr Leu Trp Glu Ala Leu Glu Ile
                85                  90                  95

Ala Gln Leu Lys Leu Val Val Lys Ala Leu Pro Gly Gly Leu Asp Ala
                100                 105                 110

Ile Ile Thr Glu Gly Gly Glu Asn Phe Ser Gln Gly Gln Arg Gln Leu
            115                 120                 125

Phe Cys Leu Ala Arg Ala Phe Val Arg Lys Thr Ser Ile Phe Ile Met
    130                 135                 140

Asp Glu Ala Thr Ala Ser Ile Asp Met Ala Thr Glu Asn Ile Leu Gln
145                 150                 155                 160

<210> SEQ ID NO 31
<211> LENGTH: 164
```

<212> TYPE: PRT
<213> ORGANISM: Homo Sapiens

<400> SEQUENCE: 31

```
Ile Lys Gly Leu Asn Leu Lys Val Gln Ser Gly Gln Thr Val Ala Leu
 1               5                  10                  15

Val Gly Asn Ser Gly Cys Gly Lys Ser Thr Thr Val Gln Leu Met Gln
            20                  25                  30

Arg Leu Tyr Asp Pro Thr Glu Gly Met Val Ser Val Asp Gly Gln Asp
        35                  40                  45

Ile Arg Thr Ile Asn Val Arg Phe Leu Arg Glu Ile Ile Gly Val Val
    50                  55                  60

Ser Gln Glu Pro Val Leu Phe Ala Thr Thr Ile Ala Glu Asn Ile Arg
65                  70                  75                  80

Tyr Gly Arg Glu Asn Val Thr Met Asp Glu Ile Glu Lys Ala Val Lys
                85                  90                  95

Glu Ala Asn Ala Tyr Asp Phe Ile Met Lys Leu Pro His Lys Phe Asp
            100                 105                 110

Thr Leu Val Gly Glu Arg Gly Ala Gln Leu Ser Gly Gly Gln Lys Gln
        115                 120                 125

Arg Ile Ala Ile Ala Arg Ala Leu Val Arg Asn Pro Lys Ile Leu Leu
    130                 135                 140

Leu Asp Glu Ala Thr Ser Ala Leu Asp Thr Glu Ser Glu Ala Val Val
145                 150                 155                 160

Gln Val Ala Leu
```

<210> SEQ ID NO 32
<211> LENGTH: 163
<212> TYPE: PRT
<213> ORGANISM: Homo Sapiens

<400> SEQUENCE: 32

```
Leu Gln Gly Leu Ser Leu Glu Val Lys Lys Gly Gln Thr Leu Ala Leu
 1               5                  10                  15

Val Gly Ser Ser Gly Cys Gly Lys Ser Thr Val Val Gln Leu Leu Glu
            20                  25                  30

Arg Phe Tyr Asp Pro Leu Ala Gly Lys Val Leu Leu Asp Gly Lys Glu
        35                  40                  45

Ile Lys Arg Leu Asn Val Gln Trp Leu Arg Ala His Leu Gly Ile Val
    50                  55                  60

Ser Gln Glu Pro Ile Leu Phe Asp Cys Ser Ile Ala Glu Asn Ile Ala
65                  70                  75                  80

Tyr Gly Asp Asn Ser Arg Val Val Ser Gln Glu Glu Ile Val Arg Ala
                85                  90                  95

Ala Lys Glu Ala Asn Ile His Ala Phe Ile Glu Ser Leu Pro Asn Lys
            100                 105                 110

Tyr Ser Thr Lys Val Gly Asp Lys Gly Thr Gln Leu Ser Gly Gly Gln
        115                 120                 125

Lys Gln Arg Ile Ala Ile Ala Arg Ala Leu Val Arg Gln Pro His Ile
    130                 135                 140

Leu Leu Leu Asp Glu Ala Thr Ser Ala Leu Asp Thr Glu Ser Glu Lys
145                 150                 155                 160

Val Val Gln
```

<210> SEQ ID NO 33

<211> LENGTH: 1530
<212> TYPE: PRT
<213> ORGANISM: Homo sapiens

<400> SEQUENCE: 33

```
Met Gly Pro Met Asp Ala Leu Cys Gly Ser Gly Glu Leu Gly Ser Lys
 1               5                  10                  15

Phe Trp Asp Ser Asn Leu Ser Val His Thr Glu Asn Pro Asp Leu Thr
             20                  25                  30

Pro Cys Phe Gln Asn Ser Leu Leu Ala Trp Val Pro Cys Ile Tyr Leu
         35                  40                  45

Trp Val Ala Leu Pro Cys Tyr Leu Leu Tyr Leu Arg His His Cys Arg
     50                  55                  60

Gly Tyr Ile Ile Leu Ser His Leu Ser Lys Leu Lys Met Val Leu Gly
 65                  70                  75                  80

Val Leu Leu Trp Cys Val Ser Trp Ala Asp Leu Phe Tyr Ser Phe His
                 85                  90                  95

Gly Leu Val His Gly Arg Ala Pro Ala Pro Val Phe Phe Val Thr Pro
            100                 105                 110

Leu Val Val Gly Val Thr Met Leu Leu Ala Thr Leu Leu Ile Gln Tyr
        115                 120                 125

Glu Arg Leu Gln Gly Val Gln Ser Ser Gly Val Leu Ile Ile Phe Trp
    130                 135                 140

Phe Leu Cys Val Val Cys Ala Ile Val Pro Phe Arg Ser Lys Ile Leu
145                 150                 155                 160

Leu Ala Lys Ala Glu Gly Glu Ile Ser Asp Pro Phe Arg Phe Thr Thr
                165                 170                 175

Phe Tyr Ile His Phe Ala Leu Val Leu Ser Ala Leu Ile Leu Ala Cys
            180                 185                 190

Phe Arg Glu Lys Pro Pro Phe Phe Ser Ala Lys Asn Val Asp Pro Asn
        195                 200                 205

Pro Tyr Pro Glu Thr Ser Val Gly Phe Leu Ser Arg Leu Phe Phe Trp
    210                 215                 220

Trp Phe Thr Lys Met Ala Ile Tyr Gly Tyr Arg His Pro Leu Glu Glu
225                 230                 235                 240

Lys Asp Leu Trp Ser Leu Lys Glu Glu Asp Arg Ser Gln Met Val Val
                245                 250                 255

Gln Gln Leu Leu Glu Ala Trp Arg Lys Gln Glu Lys Gln Thr Ala Arg
            260                 265                 270

His Lys Ala Ser Ala Ala Pro Gly Lys Asn Ala Ser Gly Glu Asp Glu
        275                 280                 285

Val Leu Leu Gly Ala Arg Pro Arg Pro Arg Lys Pro Ser Phe Leu Lys
    290                 295                 300

Ala Leu Leu Ala Thr Phe Gly Ser Ser Phe Leu Ile Ser Ala Cys Phe
305                 310                 315                 320

Lys Leu Ile Gln Asp Leu Leu Ser Phe Ile Asn Pro Gln Leu Leu Ser
                325                 330                 335

Ile Leu Ile Arg Phe Ile Ser Asn Pro Met Ala Pro Ser Trp Trp Gly
            340                 345                 350

Phe Leu Val Ala Gly Leu Met Phe Leu Cys Ser Met Met Gln Ser Leu
        355                 360                 365

Ile Leu Gln His Tyr Tyr His Tyr Ile Phe Val Thr Gly Val Lys Phe
    370                 375                 380

Arg Thr Gly Ile Met Gly Val Ile Tyr Arg Lys Ala Leu Val Ile Thr
```

```
                385                 390                 395                 400
            Asn Ser Val Lys Arg Ala Ser Thr Val Gly Glu Ile Val Asn Leu Met
                            405                 410                 415
            Ser Val Asp Ala Gln Arg Phe Met Asp Leu Ala Pro Phe Leu Asn Leu
                            420                 425                 430
            Leu Trp Ser Ala Pro Leu Gln Ile Ile Leu Ala Ile Tyr Phe Leu Trp
                            435                 440                 445
            Gln Asn Leu Gly Pro Ser Val Leu Ala Gly Val Ala Phe Met Val Leu
                450                 455                 460
            Leu Ile Pro Leu Asn Gly Ala Val Ala Val Lys Met Arg Ala Phe Gln
            465                 470                 475                 480
            Val Lys Gln Met Lys Leu Lys Asp Ser Arg Ile Lys Leu Met Ser Glu
                            485                 490                 495
            Ile Leu Asn Gly Ile Lys Val Leu Lys Leu Tyr Ala Trp Glu Pro Ser
                            500                 505                 510
            Phe Leu Lys Gln Val Glu Gly Ile Arg Gln Gly Glu Leu Gln Leu Leu
                            515                 520                 525
            Arg Thr Ala Ala Tyr Leu His Thr Thr Thr Thr Phe Thr Trp Met Cys
            530                 535                 540
            Ser Pro Phe Leu Val Thr Leu Ile Thr Leu Trp Val Tyr Val Tyr Val
            545                 550                 555                 560
            Asp Pro Asn Asn Val Leu Asp Ala Glu Lys Ala Phe Val Ser Val Ser
                            565                 570                 575
            Leu Phe Asn Ile Leu Arg Leu Pro Leu Asn Met Leu Pro Gln Leu Ile
                            580                 585                 590
            Ser Asn Leu Thr Gln Ala Ser Val Ser Leu Lys Arg Ile Gln Gln Phe
                            595                 600                 605
            Leu Ser Gln Glu Glu Leu Asp Pro Gln Ser Val Glu Arg Lys Thr Ile
                        610                 615                 620
            Ser Pro Gly Tyr Ala Ile Thr Ile His Ser Gly Thr Phe Thr Trp Ala
            625                 630                 635                 640
            Gln Asp Leu Pro Pro Thr Leu His Ser Leu Asp Ile Gln Val Pro Lys
                            645                 650                 655
            Gly Ala Leu Val Ala Val Val Gly Pro Val Gly Cys Gly Lys Ser Ser
                            660                 665                 670
            Leu Val Ser Ala Leu Leu Gly Glu Met Glu Lys Leu Glu Gly Lys Val
                        675                 680                 685
            His Met Lys Gly Ser Val Ala Tyr Val Pro Gln Gln Ala Trp Ile Gln
                        690                 695                 700
            Asn Cys Thr Leu Gln Glu Asn Val Leu Phe Gly Lys Ala Leu Asn Pro
            705                 710                 715                 720
            Lys Arg Tyr Gln Gln Thr Leu Glu Ala Cys Ala Leu Leu Ala Asp Leu
                            725                 730                 735
            Glu Met Leu Pro Gly Gly Asp Gln Thr Glu Ile Gly Glu Lys Gly Ile
                        740                 745                 750
            Asn Leu Ser Gly Gly Gln Arg Gln Arg Val Ser Leu Ala Arg Ala Val
                        755                 760                 765
            Tyr Ser Asp Ala Asp Ile Phe Leu Leu Asp Asp Pro Leu Ser Ala Val
                770                 775                 780
            Asp Ser His Val Ala Lys His Ile Phe Asp His Val Ile Gly Pro Glu
            785                 790                 795                 800
            Gly Val Leu Ala Gly Lys Thr Arg Val Leu Val Thr His Gly Ile Ser
                            805                 810                 815
```

```
Phe Leu Pro Gln Thr Asp Phe Ile Ile Val Leu Ala Asp Gly Gln Val
            820                 825                 830

Ser Glu Met Gly Pro Tyr Pro Ala Leu Leu Gln Arg Asn Gly Ser Phe
            835                 840                 845

Ala Asn Phe Leu Cys Asn Tyr Ala Pro Asp Glu Asp Gln Gly His Leu
            850                 855                 860

Glu Asp Ser Trp Thr Ala Leu Glu Gly Ala Glu Asp Lys Glu Ala Leu
865                 870                 875                 880

Leu Ile Glu Asp Thr Leu Ser Asn His Thr Asp Leu Thr Asp Asn Asp
                885                 890                 895

Pro Val Thr Tyr Val Val Gln Lys Gln Phe Met Arg Gln Leu Ser Ala
            900                 905                 910

Leu Ser Ser Asp Gly Glu Gly Gln Gly Arg Pro Val Pro Arg Arg His
            915                 920                 925

Leu Gly Pro Ser Glu Lys Val Gln Val Thr Glu Ala Lys Ala Asp Gly
            930                 935                 940

Ala Leu Thr Gln Glu Glu Lys Ala Ala Ile Gly Thr Val Glu Leu Ser
945                 950                 955                 960

Val Phe Trp Asp Tyr Ala Lys Ala Val Gly Leu Cys Thr Thr Leu Ala
                965                 970                 975

Ile Cys Leu Leu Tyr Val Gly Gln Ser Ala Ala Ile Gly Ala Asn
            980                 985                 990

Val Trp Leu Ser Ala Trp Thr Asn Asp Ala Met Ala Asp Ser Arg Gln
            995                 1000                1005

Asn Asn Thr Ser Leu Arg Leu Gly Val Tyr Ala Ala Leu Gly Ile Leu
            1010                1015                1020

Gln Gly Phe Leu Val Met Leu Ala Ala Met Ala Met Ala Ala Gly Gly
1025                1030                1035                1040

Ile Gln Ala Ala Arg Val Leu His Gln Ala Leu Leu His Asn Lys Ile
            1045                1050                1055

Arg Ser Pro Gln Ser Phe Phe Asp Thr Thr Pro Ser Gly Arg Ile Leu
            1060                1065                1070

Asn Cys Phe Ser Lys Asp Ile Tyr Val Val Asp Glu Val Leu Ala Pro
            1075                1080                1085

Val Ile Leu Met Leu Leu Asn Ser Phe Phe Asn Ala Ile Ser Thr Leu
            1090                1095                1100

Val Val Ile Met Ala Ser Thr Pro Leu Phe Thr Val Ile Leu Pro
1105                1110                1115                1120

Leu Ala Val Leu Tyr Thr Leu Val Gln Arg Phe Tyr Ala Ala Thr Ser
            1125                1130                1135

Arg Gln Leu Lys Arg Leu Glu Ser Val Ser Arg Ser Pro Ile Tyr Ser
            1140                1145                1150

His Phe Ser Glu Thr Val Thr Gly Ala Ser Val Ile Arg Ala Tyr Asn
            1155                1160                1165

Arg Ser Arg Asp Phe Glu Ile Ile Ser Asp Thr Lys Val Asp Ala Asn
            1170                1175                1180

Gln Arg Ser Cys Tyr Pro Tyr Ile Ile Ser Asn Arg Trp Leu Ser Ile
1185                1190                1195                1200

Gly Val Glu Phe Val Gly Asn Cys Val Val Leu Phe Ala Ala Leu Phe
                1205                1210                1215

Ala Val Ile Gly Arg Ser Ser Leu Asn Pro Gly Leu Val Gly Leu Ser
            1220                1225                1230
```

-continued

```
Val Ser Tyr Ser Leu Gln Val Thr Phe Ala Leu Asn Trp Met Ile Arg
        1235                1240                1245
Met Met Ser Asp Leu Glu Ser Asn Ile Val Ala Val Glu Arg Val Lys
    1250                1255                1260
Glu Tyr Ser Lys Thr Glu Thr Glu Ala Pro Trp Val Glu Gly Ser
1265                1270                1275                1280
Arg Pro Pro Glu Gly Trp Pro Pro Arg Gly Glu Val Glu Phe Arg Asn
                1285                1290                1295
Tyr Ser Val Arg Tyr Arg Pro Gly Leu Asp Leu Val Leu Arg Asp Leu
                1300                1305                1310
Ser Leu His Val His Gly Gly Glu Lys Val Gly Ile Val Gly Arg Thr
        1315                1320                1325
Gly Ala Gly Lys Ser Ser Met Thr Leu Cys Leu Phe Arg Ile Leu Glu
    1330                1335                1340
Ala Ala Lys Gly Glu Ile Arg Ile Asp Gly Leu Asn Val Ala Asp Ile
1345                1350                1355                1360
Gly Leu His Asp Leu Arg Ser Gln Leu Thr Ile Ile Pro Gln Asp Pro
                1365                1370                1375
Ile Leu Phe Ser Gly Thr Leu Arg Met Asn Leu Asp Pro Phe Gly Ser
                1380                1385                1390
Tyr Ser Glu Glu Asp Ile Trp Trp Ala Leu Glu Leu Ser His Leu His
        1395                1400                1405
Thr Phe Val Ser Ser Gln Pro Ala Gly Leu Asp Phe Gln Cys Ser Glu
        1410                1415                1420
Gly Gly Glu Asn Leu Ser Val Gly Gln Arg Gln Leu Val Cys Leu Ala
1425                1430                1435                1440
Arg Ala Leu Leu Arg Lys Ser Arg Ile Leu Val Leu Asp Glu Ala Thr
                1445                1450                1455
Ala Ala Ile Asp Leu Glu Thr Asp Asn Leu Ile Gln Ala Thr Ile Arg
                1460                1465                1470
Thr Gln Phe Asp Thr Cys Thr Val Leu Thr Ile Ala His Arg Leu Asn
        1475                1480                1485
Thr Ile Met Asp Tyr Thr Arg Val Leu Val Leu Asp Lys Gly Val Val
        1490                1495                1500
Ala Glu Phe Asp Ser Pro Ala Asn Leu Ile Ala Ala Arg Gly Ile Phe
1505                1510                1515                1520
Tyr Gly Met Ala Arg Asp Ala Gly Leu Ala
                1525                1530
```

What is claimed is:

1. An isolated nucleic acid molecule encoding a multi-specific organic anion transporter E (MOAT-E) transporter protein having the amino acid sequence of SEQ ID NO: 8.

2. The nucleic acid molecule of claim 1, which is DNA.

3. An isolated RNA molecule transcribed from the nucleic acid of claim 1.

4. The RNA molecule of claim 3, which is approximately 6 kilobase in length.

5. The nucleic acid molecule of claim 1, which comprises SEQ ID NO: 7.

6. A plasmid comprising the nucleic acid molecule of claim 1.

7. A vector comprising the nucleic acid molecule of claim 1.

8. A retroviral vector comprising the nucleic acid molecule of claim 1.

9. An isolated host cell comprising the nucleic acid molecule of claim 1.

10. The host cell as claimed in claim 9, wherein said host cell is selected from the group consisting of bacterial, fungal, mammalian, insect and plant cells.

11. The host cell as claimed in claim 9, wherein said nucleic acid is provided in a plasmid and is operably linked to mammalian regulatory elements which confer high expression and stability of mRNA transcribed from said nucleic acid.

12. The host cell as claimed in claim 9, wherein said nucleic acid is provided in a plasmid and is operably linked to mammalian regulatory control elements in reverse antisense orientation.

13. A method for screening in vitro a test compound for inhibition of multispecific organic anion transporter E (MOAT-E) mediated transport, comprising:
  a) providing a host cell comprising a MOAT-E-encoding nucleic acid, wherein said MOAT-E is SEQ ID NO: 8;
  b) contacting said host cell with a compound suspected of inhibiting MOAT-E-mediated transporter activity; and
  c) assessing inhibition of transport mediated by said compound;
  wherein an inhibition of transport indicates that the compound is an inhibitor of MOAT-E.

14. The method as claimed in claim 13, wherein inhibition of MOAT-E mediated transport is indicated by restoration of anticancer drug sensitivity.

15. The method as claimed in claim 14, wherein said inhibition of MOAT-E mediated transport is indicated by a reduction of transporter mediated cellular efflux of anticancer agents.

* * * * *